(12) United States Patent
Allan et al.

(10) Patent No.: US 7,838,638 B2
(45) Date of Patent: Nov. 23, 2010

(54) ANTI-IL-17 ANTIBODIES

(75) Inventors: Barrett Allan, Encinitas, CA (US); Chi-Kin Chow, Brownsburg, IN (US); Ling Liu, Carmel, IN (US); Jirong Lu, Carmel, IN (US); Jonathan Wendell Tetreault, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/095,398

(22) PCT Filed: Dec. 5, 2006

(86) PCT No.: PCT/US2006/061586

§ 371 (c)(1),
(2), (4) Date: May 29, 2008

(87) PCT Pub. No.: WO2007/070750

PCT Pub. Date: Jun. 21, 2007

(65) Prior Publication Data

US 2008/0269467 A1     Oct. 30, 2008

Related U.S. Application Data

(60) Provisional application No. 60/801,948, filed on May 19, 2006, provisional application No. 60/749,953, filed on Dec. 13, 2005.

(51) Int. Cl.
  *C07K 16/24* (2006.01)
(52) U.S. Cl. .............................. 530/387.3; 530/388.23
(58) Field of Classification Search .............. 530/387.3, 530/388.23, 300, 350
See application file for complete search history.

(56) References Cited

U.S. PATENT DOCUMENTS 6,274,711 B1    8/2001    Golstein et al.

FOREIGN PATENT DOCUMENTS

| EP | 0733069 B | 3/2006 |
|---|---|---|
| WO | WO 2004/106377 A | 12/2004 |
| WO | WO 2005/051422 | 6/2005 |
| WO | WO 2006/013107 A | 2/2006 |
| WO | WO 2006/054059 A | 5/2006 |

OTHER PUBLICATIONS

Giavedoni, L.D., "Simultaneous detection of multiple cytokines and chemokines from nonhuman primates using luminex technology", *Journal of Immunological Methods*, vol. 302, No. 1-2, Jun. 2005, pp. 89-101.

Moseley, T.A., et al., "Interleukin-17 family and Il-17 receptors" *Cytokine and Growth Factor Reviews*, vol. 14, No. 2, Apr. 2003, pp. 155-174.

Lubberts, E., "The role of Il-17 and Family Members in the Pathogenesis of Arthritis", *Current Opinion in Investigational Drugs*, vol. 4, No. 5, May 2003, pp. 572-577.

Hofstetter, et al., "Therapeutic efficacy of Il-17 neutralization in murine experimental autoimmune encephalomyelitis" *Cellular Immunology*, vol. 237, No. 2, Oct. 2005, pp. 123-130.

*Primary Examiner*—Stephen L Rawlings
(74) *Attorney, Agent, or Firm*—Lynn D. Apelgren; MaryAnn Wiskerchen

(57) ABSTRACT

Anti-IL-17 antibodies are identified that are characterized as having a high affinity and slow off rate for human IL-17. The antibodies of the invention may be chimeric, humanized or fully human antibodies, immunoconjugates of the antibodies or antigen-binding fragments thereof. The antibodies of the invention are useful in particular for treating autoimmune, inflammatory, cell proliferative and developmental disorders.

4 Claims, 2 Drawing Sheets

Figure 1    IL-17 Family (Human)

```
           1                                                40
IL-17      MTPGKTSLVS LLLLLSLEAI VKAGITIPR- NPGCPNSEDK
IL-17B     ----MDWPHN LLFLLTISIF LGLG1P4WP- KWKRKGQGRP
IL-17C     ----MTLLPG LLFLTWLHTC LAHHDPSLRG HPHSHGTPHC
IL-17D     -------MLV AGFLLALPPS WAAGAPRAGR RPARPRGCAD
IL-17E     MRERPRLGED SSLISLFLQV VAFLAMVMGT HTYSHWPSCC
IL-17F     --MVKYLLLS ILGLAFLSEA AARKIPKVG- HTFFQKPESC 41                                               80
IL-17      NFPRTVMVNL NIHNRNTNTN P--------- ----------
IL-17B     GPLAPGPHQV PLDLVSRMKP YARMEEYERN IEEMVAQLRN
IL-17C     YSAEELPLQA PPHLIARGAK WGQALPVALV SSLEAASHRG
IL-17D     RPEELLEQLY GRLAAGVLSA FHHTLQLGPR EQARNASCPA
IL-17E     PSKGQDTSEE LLRWSTVPVP PLEPARPNRH PESCRAS---
IL-17F

81                           *    *  **      * 120
IL-17      ---------- --------KR SSDYYNRSTS PWNLHRNEDP
IL-17B     SSELAQRKCE VN------LQ LWMSNKRSLS PWGYSINHDP
IL-17C     RHERPSATTQ CPVLRPEEVL EADTHQRSIS PWRYRVDTDE
IL-17D     GGRPADR--- --------RF RPPTNLRSVS PWAYRISYDP
IL-17E     ---------- ---------E DGPLNSRAIS PWRYELDRDL
IL-17F     ---------- --------SM SRNIESRSTS PWNYTVTWDP

121       *  *                            *
IL-17      ERYPSVIWEA KCRHLGCINA D--GNVDYHM NSVPIQQEIL
IL-17B     SRIPVDLPEA RCLCLGCVNP FT-MWEDRSM VSVPVFSQVP
IL-17C     DRYPQKLAFA ECLCRGCIDA RT-GRETAAL NSVRLLQSLL
IL-17D     ARYPRYLPEA YCLCRGCLTG LF-GEEDVRF RSAPVYMPTV
IL-17E     NRLPQDLYHA RCLCPHCVSL QTGSHMDPRG NSELLYHNQT
IL-17F     NRYPSEVVQA QCRNLGCINA Q--GKEDISM NSVPIQQETL 161                                          200
              *  *                                   *  *
IL-17      VLRREPPHCP NS-------- -FRLEKILVS VGCTCVTPIV
IL-17B     VRRRLCPPPP RTG-----PC RQRAVMETIA VGCTCIF---
IL-17C     VLRRRPCSRD GSGLPTPGAF AFHTEFIHVP VGCTCVLPRS
IL-17D     VLRRTPACAG GRS------- VYTEAYVTIP VGCTCVPEPE
IL-17E     VFYRRPCHGE KGTHKG---Y CLEFFLYRVS LACVCVRPRV
IL-17F     VVRRKHQGCS VS-------- -FQLEKVLVT VGCTCVTPVI 201                 228
IL-17      HHVA------ ---------- --------   (SEQ ID NO: 1)
IL-17B     ---------- ---------- --------   (SEQ ID NO: 2)
IL-17C     V--------- ---------- --------   (SEQ ID NO: 3)
IL-17D     KDADSINSSI DKQGAKLLLG PNDAPAGP    (SEQ ID NO: 4)
IL-17E     MG-------- ---------- --------   (SEQ ID NO: 5)
IL-17F     HHVQ------ ---------- --------   (SEQ ID NO: 6)
```

Figure 2
IL-17

```
                *   *      *  **** * * **      *     *** *   *    * * *    *
mouse           MSPGRASSVSLMLLLLLSLAATVKAAAIIPQSSACPNTEAKDFLQNVKVNLKVFNSLGAK
rat             MSPRRIPSMCLMLLLLLNLEATVKAAVLIPQSSVCPNAEANNFLQNVKVNLKVINSLSSK
rabbit          MSLGRISSVSL--LLLLCLVATVKNGIAMPRNPGCPNAEDKNFPQNVKVSLNILNK---S
human           MTPGKTSLVSL--LLLLSLEAIVKAGITIPRNPGCPNSEDKNFPRTVMVNLNIHNR-NTN
monkey          MTPGKTSLVLL--LLLLSLEAIVKAGIAIPRNSGCPNSEDKNFPRTVMVNLNIHNR-NTS

* ***  ******* * ****   ********* ***   *   *   * ***** ***
mouse           VSSRRPSDYLNRSTSPWTLHRNEDPDRYPSVIWEAQCRHQRCVNAEGKLDHHMNSVLIQQ
rat             ASSRRPSDYLNRSTSPWTLSRNEDPDRYPSVIWEAQCRHQRCVNAEGKLDHHMNSVLIQQ
rabbit          VNSRRPSDYYNRSTSPWTLHRNEDRERYPSVIWEAKCRHLGCVNAEGNEDHHMNSVPIQQ
human           TNPKRSSDYYNRSTSPWNLHRNEDPERYPSVIWEAKCRHLGCINADGNVDYHMNSVPIQQ
monkey          TNPKRSSDYYNRSTSPWNLHRNEDPERYPSVIWEAKCRHLGCVKADGNVDYHMNSVPIQQ

***** **     **    **  ** **   *****   *
mouse           EILVLKREPESCPFTFRVEKMLVGVGCTCVASIVRQAA-   (SEQ ID NO:7)
rat             EILVLKREPEKCPFTFRVEKMLVGVGCTCVSSIVRHAS-   (SEQ ID NO:8)
rabbit          EILVLRRESQHCPHSFRLEKMLVAVGCTCVTPIIHHMAX   (SEQ ID NO:9)
human           EILVLRREPPHCPNSFRLEKILVSVGCTCVTPIVHHVA-   (SEQ ID NO:1)
monkey          EILVLRREPRHCPNSFRLEKILVSVGCTCVTPIVHHVAX   (SEQ ID NO:10)
```

ANTI-IL-17 ANTIBODIES

This U.S. national phase application of PCT/US2006/061586, filed Dec. 5, 2006, which claims priority to U.S. provisional patent applications 60/749,953, filed Dec. 13, 2005 and 60/801,948 filed May 19, 2006.

FIELD OF THE INVENTION

The present invention is in the field of medicine, particularly in the field of monoclonal antibodies against human IL-17. The invention relates to neutralizing anti-IL-17 monoclonal antibodies that bind with high affinity to an IL-17 non-linear or conformational antigenic epitope comprising amino acids DGNVDYH. The antibodies of the invention may be chimeric, humanized or human antibodies, immunoconjugates of the antibodies or antigen-binding fragments thereof and are useful as a medicament for the treatment of autoimmune, inflammatory, cell proliferative and developmental disorders.

BACKGROUND OF THE INVENTION

The IL-17 family of cytokines presently includes IL-17A, IL-17B, IL-17C, IL-17D, IL-17E and IL-17F. All IL-17 family members have four highly conserved cysteine residues that are involved in the formation of intrachain disulfide linkages and have two or more cysteine residues that may be involved in interchain disulfide linkages. Members of the IL-17 family have no sequence similarity to any other known cytokines. However, a viral homologue of IL-17A was found in open reading frame 13 of herpesvirus saimiri (Yao, Z. et al., *Immunity*, 3:811, 1995) and has 72% amino acid residue identity to human IL-17A. Multiple functions have been reported for the IL-17 family members that mainly involve regulation of the immune response.

Interleukin 17 (IL-17, also referred to as IL-17A) is a 20-30 kD homodimeric glycoprotein produced predominantly by activated CD4+ T cells and functions as a proinflammatory cytokine. When a particular IL-17 family member is referred to simply as "IL-17," it is understood that the family member referred to is IL-17A. IL-17 is secreted by activated T cells at sites of inflammation not in the systemic circulation. IL-17 binds to a type I transmembrane receptor termed IL-17R which is a large ubiquitously expressed protein that demonstrates no significant sequence similarity to other known cytokine receptors. IL-17 has multiple biologic properties including upregulating adhesion molecules and inducing the production of multiple inflammatory cytokines and chemokines from various cell types including synoviocytes, chondroctes, fibroblasts, endothelial cells, epithelial cells, keratinocytes, and macrophages. Also, IL-17 induces recruitment of neutrophils to an inflammatory site through induction of chemokine release, stimulates production of prostaglandins and metalloproteinases, and inhibits proteoglycan synthesis. Furthermore, IL-17 plays an important role in the maturation of hematopoietic progenitor cells. It has been demonstrated that IL-17 has signaling roles in different organs and tissues including lung, articular cartilage, bone, brain, hematopoietic cells, kidney, skin and intestine. For a review of IL-17 bioactivity see, e.g., Kolls and Linden, *Immunity* 21:467-476, 2004, or Fossiez, et al. *Int. Rev. Immunol.* 16:541, 1998.

Increased levels of IL-17 (i.e., IL-17A) have been associated with several conditions, diseases or disorders including airway inflammation, rheumatoid arthritis ("RA"), osteoarthritis, bone erosion, intraperitoneal abscesses and adhesions, inflammatory bowel disorder ("IBD"), allograft rejection, psoriasis, certain types of cancer, angiogenesis, atherosclerosis and multiple sclerosis ("MS") (for a review see Witkowski, et al, *Cell. Mol. Life. Sci.* 61:567-579, 2004). Both IL-17 and IL-17R are up-regulated in the synovial tissue of RA patients. Blocking an IL-17 bioactivity by binding an IL-17 specific antibody or soluble receptor to IL-17 reduces inflammation and bone erosion in various animal arthritis models. (See, e.g., Lubberts et al, *Arthritis & Rheumatism*, 50:650-659, 2004). Furthermore, IL-17 has IL-1β independent effects on collagen matrix breakdown and inflammation and joint damage, while IL-17 has synergy with TNF-α to amplify inflammation.

Thus, given its localized distribution at the site of inflammation, IL-17 appears to be a novel target for the treatment of RA and other inflammatory or autoimmune diseases with a potentially greater safety profile than drugs that target the systemic circulation of pro-inflammatory cytokines such as TNF-α. Current FDA approved bioproducts (ENBREL®, REMICADE® and HUMIRA® antibodies) that bind to and neutralize TNF-α have demonstrated efficacy in reducing signs and symptoms of RA and in slowing progression of the disease in a subset of RA patients. However, not all RA patients respond equally to inhibition of a TNF-α bioactivity with these bioproducts. Additionally, IL-17 mRNA is increased in multiple sclerosis lesions and in mononuclear cells in the blood and cerebrospinal fluid of MS patients, particularly during clinical exacerbation. Accordingly, there is a need for compositions that antagonize or neutralize the activity of IL-17 in order to treat disorders, diseases or conditions wherein the presence of IL-17 bioactivity causes or contributes to an undesirable pathological effect or wherein a decrease in IL-17 bioactivity contributes to a desirable therapeutic effect, including inflammatory disorders, cell proliferative and developmental disorders and autoimmune disorders such as RA and MS and IBD.

There is a need for a neutralizing anti-IL-17 antibody that specifically binds IL-17 of human origin as well as IL-17 of a non-human mammal thereby allowing the antibody to be used in preclinical and clinical in vivo studies. Furthermore, there is a need for an IL-17-specific antibody which binds IL-17 with a high affinity and/or has a slow off rate thereby allowing the effective therapeutic dose to be minimized resulting in less frequent dosing with such an antibody than with an antibody that binds IL-17 with a lesser affinity (i.e., a higher $K_D$) and/or has a faster off rate. A high affinity IL-17-specific antibody is also desirable in that it may allow the antibody to be administered to a patient subcutaneously rather than intravenously. There is also a need for an IL-17-specific antibody with a low $IC_{50}$ value in an IL-117 bioactivity assay in order to generate a therapeutic anti-IL-17 antibody with a minimum effective therapeutic dose. It is also desirable to provide an antibody specific to IL-17 where an immune response to the antibody evoked by a patient receiving the antibody is reduced to a minimum. The present invention satisfies these needs and provides related advantages.

SUMMARY OF THE INVENTION

Antibodies of the invention are chimeric, humanized, or fully human anti-IL-17 monoclonal antibodies, and antigen-binding portions thereof, that bind a non-linear epitope comprising IL-17 amino acids DGNVDYH (SEQ ID NO: 276) and antagonize or neutralize at least one in vitro or in vivo biological activity associated with IL-17 or a portion thereof.

In one embodiment, antibodies of the invention have an $IC_{50}$ of less than or equal to about 1 nM, 900 pM, 800 pM, 700 pM, 600 pM, 560 pM or 500 pM in an in vitro IL-8 reporter assay as described, for example, in Example 6A herein or less than or equal to 560 pM in an in vitro GROα Reporter Assay as described, for example, in Example 6B herein.

In another embodiment, antibodies of the invention are characterized by a strong binding affinity ($K_D$) for human IL-17, i.e., less than about 7 pM, 6.5 pM, 6.0 pM 5.5 pM, 5.0 pM, 4.5 pM or 4.0 pM. Alternatively, the antibodies of the invention are characterized by a $K_D$ for human IL-17 of no greater than about 7 pM, 6.5 pM, 6.0 pM, 5.5 pM, 5.0 pM, 4.5 pM or preferably no greater than about 4.0 pM. Preferably the antibodies of the invention are further characterized with a $k_{off}$ rate from human IL-17 of less than $2 \times 10^{-5}$ $s^{-1}$.

In another embodiment, an anti-IL-17 antibody of the invention is characterized by specifically binding human IL-17 as well as cynomolgus monkey IL-17 while not binding mouse or rat IL-17 at levels greater than background. Additionally, an anti-IL-17 antibody of the invention binds human IL-17 (i.e., IL-17A) but does not bind human IL-17B, C, D, E or F.

In one embodiment, an anti-IL-17 monoclonal antibody of the invention comprises a light chain variable region ("LCVR") polypeptide comprising 3 CDR sequences which are present together in a Fab listed in Table 3 hereinbelow and which are present in the antibody of the invention in the same CDR position as in the Fab listed in Table 3. Preferably an anti-IL-17 monoclonal antibody of the invention comprises a LCVR polypeptide with an amino acid sequence selected from the group consisting of SEQ ID NOs: 178-243.

In another embodiment, an anti-IL-17 monoclonal antibody of the invention comprises a heavy chain variable region ("HCVR") polypeptide comprising 3 CDRs which are present together in a Fab listed in Table 2 hereinbelow and which are present in the antibody of the invention in the same CDR position as in the Fab listed in Table 2. Preferably an anti-IL-17 monoclonal antibody of the invention comprises a HCVR polypeptide with an amino acid sequence selected from the group consisting of SEQ ID NOs: 56-121.

In another embodiment, an anti-IL-17 monoclonal antibody of the invention comprises a LCVR polypeptide comprising 3 CDRs which are present together in a Fab listed in Table 3 and which are present in the antibody of the invention in the same CDR position as in the Fab listed in Table 3 and further comprises a HCVR polypeptide comprising 3 CDRs which are present together in a Fab listed in Table 2 and which are present in the antibody of the invention in the same CDR position as in the Fab listed in Table 2. Preferably the 6 CDRs of an antibody of the invention, or functional fragment thereof, exist together in a Fab listed in Table 1 hereinbelow and are present in the antibody of the invention in the same CDR position as in the Fab listed in Table 1.

In a preferred embodiment, an anti-IL-17 monoclonal antibody of the invention comprises (i) a LCVR polypeptide with an amino acid sequence selected from the group consisting of SEQ ID NOs: 178-243 and (ii) a HCVR polypeptide with an amino acid sequence selected from the group consisting of SEQ ID NOs: 56-121. In a more preferred embodiment, an antibody of the invention comprising an LCVR polypeptide with an amino acid sequence selected from the group consisting of SEQ ID NOs: 178-243 further comprises the HCVR polypeptide selected from the group consisting of SEQ ID NOs: 56-121 that is present in a Fab listed in Table 1 that comprises the particular LCVR present in the antibody.

In another embodiment, a monoclonal antibody of the invention is one which can compete for binding to human IL-17, or a portion of human IL-17, with a competing antibody wherein the competing antibody comprises two polypeptides with the amino acid sequences of SEQ ID NOs: 241 and 118.

In another embodiment, a LCVR of an anti-IL-17 monoclonal antibody of the invention comprises 1, 2 or 3 peptides, preferably 3 peptides, selected from the group consisting of peptides with a sequence as shown in (a) SEQ ID NOs: 122-149; (b) SEQ ID NOs: 150-167, and (c) SEQ ID NOs: 168-177 (i.e., one peptide from (a), one peptide from (b) and one peptide from (c) for an antibody comprising 3 said peptides). A peptide with the sequence shown in SEQ ID NOs: 122-149, when present in an antibody of the invention, is at CDRL1. A peptide with the sequence shown in SEQ ID NOs: 150-167, when present in an antibody of the invention, is at CDRL2. A peptide with the sequence shown in SEQ ID NOs: 150-167, when present in an antibody of the invention, is at CDRL3.

In another embodiment, a HCVR of an anti-IL-17 monoclonal antibody of the invention comprises 1, 2 or 3 peptides, preferably 3 peptides, selected from the group consisting of peptides with a sequence as shown in (a) SEQ ID NOs: 11-28; (b) SEQ ID NOs: 29-32, and (c) SEQ ID NOs: 33-55 and 261 (i.e., one peptide from (a), one peptide from (b) and one peptide from (c) for an antibody comprising 3 said peptides). A peptide with the sequence shown in SEQ ID NOs: 11-28, when present in said antibody, is at CDRH1. A peptide with the sequence shown in SEQ ID NOs: 29-32, when present in said antibody, is at CDRH2. A peptide with the sequence shown in SEQ ID NOs: 33-55 and 261, when present in said antibody, is at CDRH3.

The present invention further provides an anti-IL-17 monoclonal antibody comprising six peptides selected from the group consisting of peptides with a sequence as shown in (a) SEQ ID NOs: 122-149; (b) SEQ ID NOs: 150-167, (c) SEQ ID NOs: 168-177, (d) SEQ ID NOs: 11-28; (e) SEQ ID NOs: 29-32, and (f) SEQ ID NOs: 33-55 and 261 (i.e., one peptide from each of (a-f)); preferably the six peptides coexist in a Fab listed in Table 1 herein. A peptide with the sequence shown in SEQ ID NOs: 122-149, when present in an antibody of the invention, is at CDRL1. A peptide with the sequence shown in SEQ ID NOs: 150-167, when present in an antibody of the invention, is at CDRL2. A peptide with the sequence shown in SEQ ID NOs: 150-167, when present in an antibody of the invention, is at CDRL3. A peptide with the sequence shown in SEQ ID NOs: 11-28, when present in said antibody, is at CDRH1. A peptide with the sequence shown in SEQ ID NOs: 29-32, when present in said antibody, is at CDRH2. A peptide with the sequence shown in SEQ ID NOs: 33-55 and 261, when present in said antibody, is at CDRH3.

The present invention further provides an anti-IL-17 monoclonal antibody comprising the six peptides with the sequences as shown in SEQ ID NOs: 247, 248, 249, 244, 245 and 246. The peptide with the sequence shown in SEQ ID NO: 247 is at CDRL1. The peptide with the sequence shown in SEQ ID NO: 248 is at CDRL2. The peptide with the sequence shown in SEQ ID NO: 249 is at CDRL3. The peptide with the sequence shown in SEQ ID NO: 244 is at CDRH1. The peptide with the sequence shown in SEQ ID NO: 245 is at CDRH2. The peptide with the sequence shown in SEQ ID NO: 246 is at CDRH3.

An anti-IL-17 monoclonal antibody of the invention may comprise or consist of an intact antibody (i.e., full length), a substantially intact antibody or an antigen-binding portion thereof, e.g., a Fab fragment, a F(ab')$_2$ fragment or a single chain Fv fragment. Furthermore, an antibody of the invention may be labeled with a detectable label, immobilized on a solid phase and/or conjugated with a heterologous compound, e.g., an enzyme, toxin or polyethylene glycol molecule.

In another embodiment, the invention provides a method of preparing an anti-IL-17 monoclonal antibody of the invention comprising maintaining a host cell of the invention (i.e., host cell that has been transformed, transduced or infected with a vector (or vectors) of the invention expressing an antibody of the invention) under conditions appropriate for expression of a monoclonal antibody of the invention, whereby such antibody is expressed. The method may further comprise the step of isolating the monoclonal antibody of the invention from the cell or preferably from the culture media in which the cell is grown.

Diagnostic uses for monoclonal antibodies of the invention are contemplated. In one diagnostic application, the invention provides a method for determining the level of IL-17 protein in a sample comprising exposing a sample to be tested to an anti-IL-17 antibody of the invention under binding conditions and determining specific binding of the antibody to the sample. An anti-IL-17 antibody of the invention may be used to determine the levels of IL-17 in test samples by comparing test sample values to a standard curve generated by binding said antibody to samples with known amounts of IL-17. The invention further provides a kit comprising an antibody of the invention and, preferably, instructions for using the antibody to detect IL-117 protein in a sample.

The invention provides a composition, preferably a pharmaceutical composition, comprising an anti-IL-17 monoclonal antibody of the invention. The pharmaceutical composition of the invention may further comprise a pharmaceutically acceptable carrier, excipient and/or diluent. In said pharmaceutical composition, the anti-IL-17 monoclonal antibody of the invention is the sole active ingredient. Preferably the pharmaceutical composition comprises a homogeneous or substantially homogeneous population of an anti-IL-17 monoclonal antibody of the invention. The composition for therapeutic use is physiologically compatible, sterile and may be lyophilized and optionally supplied with an appropriate diluent.

The invention provides a method of inhibiting at least one IL-17 bioactivity in an animal, preferably a mammal, more preferably a human, in need thereof comprising administering a therapeutically effective amount, or IL-17 neutralizing amount, of an anti-IL-17 monoclonal antibody of the invention to said animal. The invention further provides a method of treating a disease or disorder ameliorated by neutralizing or antagonizing an IL-17 bioactivity, e.g., inhibition of signal transduction resulting from the binding of IL-17 to its receptor, that comprises administering to a patient (e.g., a human) in need of such treatment or prevention a therapeutically effective amount of IL-17 neutralizing amount, of a monoclonal antibody of the invention.

The invention embodies an anti-IL-17 monoclonal antibody of the invention for use in the manufacture of a medicament for administration to a mammal, preferably a human, for the treatment of, e.g., an autoimmune disorder or inflammation disorder or cell-proliferation disorder.

The invention further embodies an article of manufacture comprising a packaging material and an antibody of the invention contained within said packaging material, wherein the packaging material comprises a package insert which indicates that the antibody specifically neutralizes an IL-17 activity or decreases the level of functional IL-17 present in the system.

The invention further provides isolated nucleic acid molecules encoding an antibody of the invention or light chain or heavy chain thereof; a vector (or vectors) comprising said nucleic acid, optionally operably linked to control sequences recognized by a host cell transformed with the vector; a host cell comprising that vector; a process for producing an antibody of the invention comprising culturing the host cell so that the nucleic acid is expressed and, optionally, recovering the antibody from the host cell culture medium.

The invention further provides isolated nucleic acid molecules encoding cynomolgus monkey IL-17 (SEQ ID NO: 253) or rabbit IL-17 (SEQ ID NO: 251); the IL-17 protein encoded by the monkey or rabbit nucleic acid (SEQ ID NOs: 10 or 9 respectively); vectors comprising said nucleic acid molecule; host cell comprising said vector; and a process for producing cynomolgus monkey IL-17 or rabbit IL-17.

BRIEF DESCRIPTION OF THE DRAWINGS

FIG. 1 shows the amino acid sequence alignment of members of the human IL-17 family of proteins (IL-17, IL-17B, IL-17C, IL-17D, IL-17E and IL-17F).

FIG. 2 shows the amino acid sequence alignment of IL-17 from human, rabbit, rat, cynomolgus monkey and murine species.

DETAILED DESCRIPTION OF THE INVENTION

The invention presents chimeric, humanized or fully human anti-IL-17 monoclonal antibodies, or antigen-binding portions thereof, able to neutralize or antagonize at least one IL-17 activity in vitro and/or in vivo Preferably, such antibodies of the invention are further characterized as having an $IC_{50}$ less than about 600 or 560 pM in e.g., an in vitro IL-8 reporter assay or GROα reporter assay (see, e.g., Example 6) and/or preferably having a strong binding affinity with IL-17 of less than 4 pM. The antibodies of the invention are further characterized in that they specifically bind human and cynomolgus monkey IL-17 (SEQ ID NOs: 1 and 10 respectively) but do not bind murine or rat IL-17 (SEQ ID NOs: 7 and 8 respectively). The antigenic epitope to which monoclonal antibodies of the invention bind is a non-linear epitope of human (and monkey) IL-17 and comprises residues DGN-VDYH (SEQ ID NO: 276) of IL-17. An antibody of the invention makes contact with the peptide DGNVDYH when it is in the context of the full-length IL-17.

Definitions

"Interleukin 17" also referred to as "IL-17" or "IL-17A" is a 20-30 kD glycosylated homodimeric protein. The human IL-17 gene codes for a 155 amino acid protein that has a 19 amino acid signal sequence and a 136 amino acid mature segment. Human IL-17 shows amino acid sequence identity of 62.5% and 58% to the mouse and rat amino acid IL-17 sequences, respectively as shown in FIG. 2. Human IL-17 shows amino acid sequence identity of 97.4% to the cynomolgus monkey IL-17.

A full-length antibody as it exists naturally is an immunoglobulin molecule comprised of four peptide chains, two heavy (H) chains (about 50-70 kDa when full length) and two light (L) chains (about 25 kDa when full length) interconnected by disulfide bonds. The amino terminal portion of each chain includes a variable region of about 100-110 or more amino acids primarily responsible for antigen recognition. The carboxy-terminal portion of each chain defines a constant region primarily responsible for effector function.

Light chains are classified as kappa or lambda and characterized by a particular constant region. Each light chain is comprised of an N-terminal light chain variable region (herein "LCVR") and a light chain constant region comprised of one domain, CL. Heavy chains are classified as gamma, mu, alpha, delta, or epsilon, and define the antibody's isotype as IgG, IgM, IgA, IgD, and IgE, respectively and several of these may be further divided into subclasses (isotypes) e.g., $IgG_1$, $IgG_2$, $IgG_3$, $IgG_4$, $IgA_1$ and $IgA_2$. Each heavy chain type is characterized by a particular constant region. Each heavy chain is comprised of an N-terminal heavy chain variable region (herein "HCVR") and a heavy chain constant region. The heavy chain constant region is comprised of three domains (CH1, CH2, and CH3) for IgG, IgD, and IgA; and 4 domains (CH1, CH2, CH3, and CH4) for IgM and IgE.

The HCVR and LCVR regions can be further subdivided into regions of hypervariability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. For full-length antibodies of the invention the light chains preferably comprise, downstream of FR4, a polypeptide with the sequence shown in SEQ ID NO: 277. For full-length antibodies of the invention the heavy chains preferably comprise, downstream of FR4, a polypeptide with the sequence shown in SEQ ID NO: 278. Herein the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues which form specific interactions with the antigen. The numbering and positioning of CDR amino acid residues within the HCVR and LCVR regions is in accordance with the well-known Kabat numbering convention.

The term "antibody," in reference to an anti-IL-17 monoclonal antibody of the invention (or simply "antibody of the invention"), as used herein, refers to a monoclonal antibody. A "monoclonal antibody" as used herein refers to a rodent, preferably murine antibody, a chimeric antibody, a humanized antibody or a fully human antibody, unless otherwise indicated herein. Monoclonal antibodies of the invention can be produced using e.g., hybridoma techniques well known in the art, as well as recombinant technologies, phage display technologies, synthetic or recombinant technologies or combinations of such technologies readily known in the art. The term "monoclonal antibody" as used herein is not limited to antibodies produced through hybridoma technology. "Monoclonal antibody" refers to an antibody that is derived from a single copy or clone, including e.g., eukaryotic, prokaryotic, or phage clone, and not the method by which it is produced. A "monoclonal antibody" can be an intact antibody (comprising a complete or full-length Fc region), a substantially intact antibody, or a portion or fragment of an antibody comprising an antigen-binding portion, e.g., a Fab fragment, Fab' fragment or $F(ab')_2$ fragment of a murine antibody or of a chimeric, humanized or human antibody. The "Fab" fragment contains a variable and constant domain of the light chain and a variable domain and the first constant domain (CH1) of the heavy chain. "$F(ab')_2$" antibody fragments comprise a pair of Fab fragments which are generally covalently linked near their carboxy termini by hinge cysteines between them. Other chemical couplings of antibody fragments are also known in the art.

The variable region of each light-heavy chain pair forms an antigen-binding site of the antibody. Thus, an intact IgG antibody has two binding sites. Except in bifunctional or bispecific antibodies, the two antigen-binging sites of the antibody are the same. As used herein, the "antigen-binding portion" or "antigen-binding region" or "antigen-binding domain" refers interchangeably to that portion of an antibody molecule which contains the amino acid residues that interact with an antigen and confer on the antibody its specificity and affinity for the antigen. This antibody portion includes the "framework" amino acid residues necessary to maintain the proper conformation of the antigen-binding residues. Preferably, the CDRs of the antigen-binding region of the antibodies of the invention are entirely or substantially of murine origin, optionally with certain amino acid residues altered, e.g., substituted with a different amino acid residue, (see e.g., Tables 2 and 3) to optimize a particular property of the antibody, e.g., $K_D$, $k_{off}$, $IC_{50}$. Preferably the framework regions of antibodies of the invention are of human origin or substantially of human origin (at least 80%, 85%, 90%, 95%, 96%, 97%, 98% or 99% of human origin. Preferred framework regions of antibodies of the invention have the following sequences: SEQ ID NOs: 262 (HCVR FR1), 263 (HCVR F2), 264 (HCVR FR3), 265 (HCVR FR4), 266 (LCVR FR1), 267 (LCVR FR2), 268 (LCVR FR3), 269 (LCVR FR4) and follow Kabat numbering. In other embodiments, the antigen-binding region of an IL-17 antibody of the invention can be derived from other non-human species including, but not limited to, rabbit, rat or hamster. Alternatively, the antigen-binding region can be derived from human sequence.

Furthermore, a "monoclonal antibody" as used herein can be a single chain Fv fragment that may be produced by joining the DNA encoding a LCVR and the DNA encoding a HCVR with a linker sequence. (See, Pluckthun, *The Pharmacology of Monoclonal Antibodies*, vol. 113, Rosenburg and Moore eds., Springer-Verlag, New York, pp 269-315, 1994). It is understood that regardless of whether fragments are specified, the term "antibody" as used herein includes such fragments as well as single chain forms. As long as the protein retains the ability to specifically or preferentially bind its intended target (i.e., epitope or antigen), it is included within the term "antibody." Antibodies may or may not be glycosylated and still fall within the bounds of the invention.

A population of "monoclonal antibodies," refers to a homogeneous or substantially homogeneous antibody population (i.e., at least about 85%, 90%, 91%, 92%, 93%, 94%, 95%, 96%, more preferably at least about 97% or 98% or most preferably at least 99% of the antibodies in the population would compete in an ELISA assay for the same antigen or epitope or more preferably the antibodies are identical in amino acid sequence. Antibodies may or may not be glycosylated and still fall within the bounds of the invention. Monoclonal antibodies may be homogeneous if they have identical amino acid sequence although they may differ in a post-translational modification, e.g., glycosylation pattern.

A "variant" antibody, refers herein to a molecule which differs in amino acid sequence from a "parent" antibody amino acid sequence by virtue of addition, deletion and/or substitution of one or more amino acid residue(s) of the parent antibody sequence. In a preferred embodiment, the variant antibody comprises at least one amino acid (e.g., from one to about ten, and preferably 2, 3, 4, 5, 6, 7 or 8) addition, deletion and/or substitution in the CDR regions of the parent antibody. Identity or homology with respect to the variant antibody sequence is defined herein as the percentage of amino acid residues in the variant antibody sequence that are identical with the parent antibody residues after aligning the sequences and introducing gaps, if necessary, to achieve the maximum percent sequence identity. The variant antibody retains the ability to bind the antigen, or preferably, the epitope, to which the parent antibody binds and preferably has at least one property or bioactivity that is superior to that of the parent antibody. For example, the variant antibody preferably has stronger binding affinity, slower off-rate, lower $IC_{50}$ or enhanced ability to inhibit an antigen bioactivity than does the parent antibody. A variant antibody of particular interest herein is one which displays at least about 2-fold, preferably at least about 5-fold, 10-fold or 20-fold enhancement in a property or bioactivity when compared to the parent antibody.

The "parent" antibody herein is one which is encoded by an amino acid sequence used for the preparation of a variant antibody. The parent antibody may have framework sequence of murine origin, but preferably the framework sequence is entirely or substantially of human origin. The parent antibody may be a murine, chimeric, humanized or human antibody.

The term "specifically binds" as used herein refers to the situation in which one member of a specific binding pair does not significantly bind to molecules other than its specific binding partner(s). The term is also applicable where e.g., an antigen-binding domain of an antibody of the invention is specific for a particular epitope that is carried by a number of antigens, in which case the specific antibody carrying the antigen-binding domain will be able to bind to the various antigens carrying the epitope. Accordingly a monoclonal antibody of the invention specifically binds human IL-17 (i.e., IL-17A) while it does not specifically bind human IL-17B, IL-17C, IL-17D, IL-17E, IL-17F. Further, a monoclonal antibody of the invention specifically binds human IL-17 and cynomolgus monkey IL-17 but does not specifically bind rat IL-17 or murine IL-17. Further a monoclonal antibody of the invention specifically binds a non-linear or conformational human IL-17 epitope comprising amino acids DGNDYH but does not bind a human IL-17 epitope which does not comprise amino acids DGNDYH.

The term "preferentially binds" as used herein, refers to the situation in which an antibody binds a specific antigen at least about 20% greater, preferably at least about 50%, 2-fold, 20-fold, 50-fold or 100-fold greater than it binds a different antigen as measured by a technique available in the art, e.g., competition ELISA or $K_D$ measurement with a BIACORE or KINEXA assay. An antibody may preferentially bind one epitope within an antigen over a different epitope within the same antigen. Accordingly an antibody of the invention preferentially binds human IL-17 over rabbit IL-17.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. By "inhibiting epitope" and/or "neutralizing epitope" is intended an epitope, which when in the context of the intact antigenic molecule and when bound by an antibody specific to the epitope, results in loss or diminution of a biological activity of the molecule in vivo or in vitro or in an organism containing the molecule.

The term "epitope," as used herein, further refers to a portion of a polypeptide having antigenic and/or immunogenic activity in an animal, preferably a mammal, e.g., a mouse or a human. The term "antigenic epitope," as used herein, is defined as a portion of a polypeptide to which an antibody can specifically bind as determined by any method well known in the art, for example, by conventional immunoassays. Antigenic epitopes need not necessarily be immunogenic, buy may be immunogenic. An "immunogenic epitope," as used herein, is defined as a portion of a polypeptide that elicits an antibody response in an animal, as determined by any method known in the art. A "nonlinear epitope" or "conformational epitope" comprises noncontiguous polypeptides (or amino acids) within the antigenic protein to which an antibody specific to the epitope binds.

The phrases "biological property" or "biological characteristic," or the terms "activity" or "bioactivity," in reference to an antibody of the present invention, are used interchangeably herein and include, but are not limited to, epitope/antigen affinity and specificity, ability to neutralize or antagonize an activity of IL-17 in vivo or in vitro, $IC_{50}$, in vivo stability of the antibody and the immunogenic properties of the antibody. Other identifiable biological properties or characteristics of an antibody recognized in the art include, for example, cross-reactivity, (i.e., with non-human homologs of the targeted peptide, or with other proteins or tissues, generally), and ability to preserve high expression levels of protein in mammalian cells. The aforementioned properties or characteristics can be observed, measured or assessed using art-recognized techniques including, but not limited to, ELISA, competitive ELISA, BIACORE or KINEXA surface plasmon resonance analysis, in vitro or in vivo neutralization assays without limit, receptor binding, cytokine or growth factor production and/or secretion, signal transduction and immunohistochemistry with tissue sections from different sources including human, primate, or any other source.

The term "inhibit" or "neutralize" as used herein with respect to an activity of an antibody of the invention means the ability to substantially antagonize, prohibit, prevent, restrain, slow, disrupt, eliminate, stop, or reverse e.g., progression or severity of that which is being inhibited including, but not limited to, a biological activity (e.g., an IL-17 activity) or property, a disease or a condition. The inhibition or neutralization of an IL-17 activity resulting from binding of an antibody of the invention with IL-17 is preferably at least about 20%, 30%, 40%, 50%, 60%, 70%, 80%, 90%, 95% or higher.

The term "isolated" when used in relation to a nucleic acid or protein (e.g., an antibody) refers to a nucleic acid molecule or protein that is identified and separated from at least one contaminant with which it is ordinarily associated in its natural source. Preferably, an "isolated antibody" is an antibody that is substantially free of other antibodies having different antigenic specificities (e.g. pharmaceutical compositions of the invention comprise an isolated antibody that specifically binds IL-17 and is substantially free of antibodies that specifically bind antigens other than IL-17).

The terms "Kabat numbering" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)).

A polynucleotide is "operably linked" to another polynucleotide when it is placed into a functional relationship with the other polynucleotide. For example, a promoter or enhancer is operably linked to a coding sequence if it affects the transcription of the sequence. A peptide is "operably linked" to another peptide when the polynucleotides encoding them are operably linked, preferably they are in the same open reading frame.

The terms "individual," "subject," and "patient," used interchangeably herein, refer to a mammal, including, but not limited to, murines, simians, humans, mammalian farm animals, mammalian sport animals, and mammalian pets; preferably the term refers to humans. In a certain embodiment, the subject, preferably a mammal, preferably a human, is further characterized with a disease or disorder or condition that would benefit from a decreased bioactivity of IL-17.

The term "vector" includes a nucleic acid molecule capable of transporting another nucleic acid to which it has been linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably linked. Such vectors are referred to herein as "recombinant expression vectors" (or simply "expression vectors") and exemplary vectors are well known in the art.

As used herein, the expressions "cell," "host cell," "cell line," and "cell culture" are used interchangeably and include an individual cell or cell culture that is a recipient of any isolated polynucleotide of the invention or any recombinant vector(s) comprising a sequence encoding a HCVR, LCVR or monoclonal antibody of the invention. Host cells include progeny of a single host cell, and the progeny may not necessarily be completely identical (in morphology or in total DNA complement) to the original parent cell due to natural, accidental, or deliberate mutation and/or change. A host cell includes cells transformed, transduced or infected with a recombinant vector or a polynucleotide expressing a monoclonal antibody of the invention or a light chain or heavy chain thereof. A host cell which comprises a recombinant vector of the invention, either stably incorporated into the host chromosome or not, may also be referred to as a "recombinant host cell". Preferred host cells for use in the invention are CHO cells (e.g., ATCC CRL-9096), NS0 cells, SP2/0 cells, COS cells (ATCC e.g., CRL-1650, CRL-1651) and HeLa (ATCC CCL-2). Additional host cells for use in the invention include plant cells, yeast cells, other mammalian cells and prokaryotic cells.

Antibody Characterization

The present invention relates to isolated, monoclonal antibodies that specifically bind human IL-17 (i.e., IL-17A) with high affinity. The antibodies of the invention are preferably chimeric, humanized or human antibodies or antigen-binding portions thereof. Furthermore, antibodies of the invention neutralize or antagonize at least one IL-17 biological activity in vivo and/or in vitro. Specific binding of an anti-IL-17 monoclonal antibody of the invention, (including antigen-binding portions thereof) to IL-17 allows said antibody to be used as a therapeutic for IL-17-associated diseases and disorders, i.e., conditions, diseases or disorders which benefit from inhibition of an IL-17 biological activity.

The antigenic IL-17 epitope to which the antibodies of the invention bind is a non-linear epitope that comprises amino acids ADGNVDYHMN (SEQ ID NO: 266), more preferably amino acids DGNVDYIH (SEQ ID NO: 267) of human IL-17. Antibodies which bind said epitope, specifically and preferentially bind human IL-17 and cynomolgus monkey IL-17 as compared to their binding murine IL-17 or rat IL-17. The monoclonal antibodies of the invention bind human IL-17 at least 5, 10, 20, 30, 40, 50, 60, 70, 80, 90, or 100-fold greater (e.g., greater affinity or greater specificity) than with which it binds murine IL-17 or rat IL-17; more preferably at least 150, 200, 250, 300, 350, 400, 450, 500, 550 or 600-fold greater than with which it binds murine IL-17 or rat IL-17 even more preferably it does not bind murine IL-17 or rat IL-17 at levels greater than background levels as determined e.g., by ELISA assay, competition ELISA assay or $K_D$ values in a BIACORE or KINEXA assay.

In a preferred embodiment, the invention provides an anti-IL-17 monoclonal antibody that possesses a strong binding affinity for human IL-17, i.e., binds human IL-17, or a portion thereof comprising DGNVDYH (SEQ ID NO: 267) [i.e., antibody contacts the DGNVDYH polypeptide], with a binding affinity ($K_D$) for human IL-17 of less than about 7 pM, 6.5 pM or 6 pM, preferably less than about 5.5 pM, 5 pM or 4.5 pM and most preferably less than about 4 pM. Alternatively, the antibodies of the invention are characterized by a $K_D$ for human IL-17 of no greater than about 7 pM, 6.5 pM or 6 pM, preferably no greater than about 5.5 pM, 5 pM or 4.5 pM and most preferably no greater than about 4 pM. Antibody affinities may be determined as described in the examples hereinbelow or other methods available in the art. Preferably the anti-IL-17 antibodies of the invention which possess a strong binding affinity as described above also bind a non-linear human IL-17 epitope that comprises amino acids ADGNVDYHMN (SEQ ID NO: 266), more preferably amino acids DGNVDYH (SEQ ID NO: 267), wherein the antibody makes contact with the polypeptide DGNVDYH.

In one embodiment, the antibodies of the invention have an off rate ($k_{off}$) for human IL-17 of less than $5 \times 10^{-5}$, $4 \times 10^{-5}$, $3 \times 10^{-5}$ or $2 \times 10^{-5}$ s$^{-1}$. In a preferred embodiment, the antibodies of the invention characterized by possessing a strong binding affinity for human IL-17 as described above ($K_D$ less than about 7 pM or 6 pM, preferably less than about 5 pM or 4.5 pM and most preferably less than about 4 pM) also have an off rate ($k_{off}$) for human IL-17 of less than $5 \times 10^{-5}$, $4 \times 10^{-5}$, $3 \times 10^{-5}$ or $2 \times 10^{-5}$ s$^{-1}$ and even more preferably also bind a non-linear human IL-17 epitope that comprises amino acids ADGNVDYHMN (SEQ ID NO: 266), more preferably amino acids DGNVDYH (SEQ ID NO: 267) of human IL-17.

In another embodiment, the antibodies of the invention have an IC$_{50}$ of less than 1 nM, 900 pM, 800 pM, 700 pM, 650 pM, 600 pM, 560 pM, 550 pM or 500 pM in e.g., an in vitro IL-8 reporter assay or less than about 560 pM in a GROα reporter assay (see Example 6). In a preferred embodiment, the antibodies of the invention are characterized by possessing a strong binding affinity for human IL-17 as described above ($K_D$ less than about 7 pM or 6 pM, preferably less than about 5 pM or 4.5 pM and most preferably less than about 4 pM) and also have an IC$_{50}$ of less than 1 nM, 900 pM, 800 pM, 700 pM, 650 pM, 600 pM, 560 pM, 550 pM or 500 pM in e.g., an in vitro IL-8 reporter assay or less than about 560 pM in a GROα reporter assay and even more preferably also have an off rate ($k_{off}$) for human IL-17 of less than $5 \times 10^{-5}$, $4 \times 10^{-5}$, $3 \times 10^{-5}$ or $2 \times 10^{-5}$ s$^{-1}$ and even more preferably also bind a non-linear human IL-17 epitope that comprises amino acids DGNVDYH (SEQ ID NO: 267) of human IL-17 wherein the antibody contacts the DGNVDYH polypeptide.

The most preferred embodiment of the invention is an anti-IL-17 antibody comprising a light chain amino acid sequence consisting of SEQ ID NO: 279 and a heavy chain amino acid sequence consisting of SEQ ID NO: 280. Preferably this antibody comprises two identical light chains and two identical heavy chains. Preferably the light chain with amino acid sequence as shown in SEQ ID NO: 279 is encoded by a nucleic acid comprising the sequence shown in SEQ ID NO: 281 (including signal sequence) or SEQ ID NO: 283 (without the signal sequence). Preferably the heavy chain with amino acid sequence as shown in SEQ ID NO: 280 is encoded by a nucleic acid comprising the sequence shown in SEQ ID NO: 282 (including the signal sequence) or SEQ ID NO: 284 (without the signal sequence).

Monoclonal antibodies ("mAbs") may be made using the hybridoma method widely known in the art (see e.g., Kohler et al., *Nature*, 256:495, 1975) or may be made by recombinant DNA methods (e.g., as in U.S. Pat. No. 4,816,567). Generally, a hybridoma can be produced by fusing a suitable immortal cell line (e.g., a myeloma cell line such as SP2/0) with antibody producing cells of the immunized animal. The antibody producing cell, preferably those of the spleen or lymph nodes, are obtained from animals immunized with the antigen of interest. The fused cells (hybridomas) can be isolated using selective culture conditions, and cloned by limiting dilution. Culture medium in which hybridoma cells are growing is assayed for production of monoclonal antibodies directed against the antigen. Preferably, the binding specificity of mAbs produced by hybridoma cells is determined by immunoprecipitation or by an in vitro binding assay, such as radioimmunoassay or ELISA. Cells which produce antibodies with the desired binding properties can be selected by a suitable assay. Methods for such isolation and screening are well known in the art.

Other suitable methods of producing or isolating antibodies of the invention, including human or artificial antibodies, can be used, including, for example, methods which select a recombinant antibody (e.g., single chain Fv or Fab) from a library, or which rely upon immunization of transgenic animals (e.g., mice) capable of producing a repertoire of human antibodies (see e.g., Jakobovits et al., *Proc. Natl. Acad. Sci. USA*, 90:2551-2555, 1993; Jakobovits et al., *Nature*, 362: 255-258, 1993; U.S. Pat. Nos. 5,545,806 and 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. For example, nucleic acids encoding a chimeric or humanized chain can be expressed to produce a contiguous protein. See e.g., U.S. Pat. No. 4,816,567; European Patent No. 125,023 B1; U.S. Pat. No. 4,816,397; European Patent No. 120,694 B1; WO 86/01533; European Patent No. 194, 276 B1; U.S. Pat. No. 5,225,539; European Patent No. 239, 400 B1 and U.S. Pat. Nos. 5,585,089 and 5,698,762.

In addition, functional fragments of antibodies (i.e., antigen-binding fragments), including fragments of chimeric, humanized, primatized or single chain antibodies, can also be produced and fall within the scope of the invention. Preferred functional fragments retain an antigen-binding function of a corresponding full-length antibody. Particularly preferred functional fragments retain the ability to inhibit one or more functions or bioactivities characteristic of a mammalian mature IL-17, preferably human IL-17, such as a binding activity, a signaling activity, and/or stimulation or inhibition of a cellular response. For example, in one embodiment, a functional fragment can inhibit the interaction of mature IL-17 with its receptor and/or can inhibit one or more receptor-mediated functions.

Antibody portions capable of binding to human IL-17 include, but are not limited to, Fv, Fab, Fab' and F(ab')$_2$ fragments and are encompassed by the invention. Such fragments can be produced by enzymatic cleavage or by recombinant techniques. For instance, papain or pepsin cleavage of an intact antibody can generate Fab or F(ab')$_2$ fragments, respectively. Papain digestion of antibodies produces two identical antigen-binding fragments, called "Fab" fragments, each with a single antigen-binding site. The Fab fragment also contains the constant domain of the light chain and the first constant domain (CH1) of the heavy chain. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. To overcome the tendency of non-covalently linked HCVR and LCVR domains in the Fv to dissociate when co-expressed in a host cell, a single chain Fv fragment (scFv) can be constructed in which a flexible and adequately long polypeptide links either the C-terminus of the HCVR to the N-terminus of the LCVR or the C-terminus of the LCVR to the N-terminus of the HCVR. A commonly used linker is a 15-residue (Gly$_4$Ser)$_3$ peptide. For a review of sFv, see Pluckthun in *The Pharmacology of Monoclonal Antibodies*, vol. 113, Rosenburg and Moore eds., Springer-Verlag, New York, pp. 269-315 (1994). Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Selection of antibody fragments from libraries using enrichment technologies such as phage-display (Matthews D J and Wells J A. *Science*. 260:1113-7, 1993), ribosome display (Hanes, et al., *Proc. Natl. Acad. Sci. (USA)* 95:14130-5, 1998), bacterial display (Samuelson P., et al., *Journal of Biotechnology*. 96:129-54, 2002) or yeast display (Kieke M. C., et al., *Protein Engineering*, 10: 1303-10, 1997) have proven to be successful alternatives to classical hybridoma technology (Review: Little M. et al., *Immunology Today*, 21:364-70, 2000).

Variant Antibodies

A murine monoclonal antibody or a human antibody (produced e.g., in a transgenic mouse) raised against IL-17 may be a parent antibody. A parent antibody may be further altered to create a chimeric or humanized form of the antibody or other variant form of the antibody using methods available in the art, e.g., PCR mutagenesis. Such chimeric, humanized, or otherwise variant antibodies, may serve as parent antibodies for further variation or mutagenesis. Parent antibodies of the invention may be mutagenized, e.g., within the CDR domain(s) (see, e.g., Tables 2 and 3) to create variant antibodies that may be screened for presence of a property of interest, e.g., binding affinity (lower $K_D$), IC$_{50}$, specificity, preferential binding, etc. Preferably the property of interest in the variant antibody is an improvement over that property in the parent antibody. An amino acid substitution variant antibody is preferred and has at least 1, 2, 3, 4, 5, 6, 7, 8, 9 or 10 amino acid residue(s) of the parent antibody molecule removed and a different residue inserted in its place. The site of greatest interest for substitutional mutagenesis is one or more CDR regions, but FR alterations are also contemplated. Conservative amino acid substitutions are preferred; although, for more substantial changes, non-conservative amino acid changes may be introduced and the resulting antibodies screened for the property of interest.

A convenient way for generating substitution variants of a parent antibody is affinity maturation using phage display. Briefly, a polynucleotide molecule encoding a parent antibody is mutated within one or more CDR regions to generate all possible amino acid substitutions at each amino acid residue at which a substitution is desired. The antibody variants thus generated are displayed in a monovalent fashion from filamentous phage particles as fusions to the gene III product of M13 packaged within each particle. The phage-displayed variant antibodies are then screened for their biological activity (e.g., binding affinity, specificity, $IC_{50}$). In order to identify candidate CDR region sites for modification, alanine scanning mutagens can be performed to identify CDR region residues contributing significantly to antigen binding.

Alternatively, or in addition, it may be beneficial to analyze a crystal structure of the antigen-antibody complex to identify contact points between the antibody and IL-17. Such contact residues and neighboring residues are candidates for substitution according to the techniques elaborated herein or known in the art. Alternatively, or in addition, random mutagenesis or point mutagenesis may be performed, on one or more polynucleotide molecules encoding at least one CDR. The mutagenesis may be performed, at one or more positions, either while the CDR is operably linked to the framework region within the variable region or while the CDR is independent of other variable region sequence and then the altered CDR returned to the variable region using recombinant DNA technology. Once such variant antibodies are generated the panel of variants is subjected to screening for a property or activity of interest and antibodies with superior properties in one or more relevant assays may be selected for further development.

Any cysteine residue not involved in maintaining the proper conformation of an anti-IL-17 antibody of the invention may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the parent antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagines side chain. Thus the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Sequence

A preferred monoclonal antibody of the invention comprises a LCVR comprising a peptide with a sequence selected from the group consisting of SEQ ID NOs: 178-243 and/or a HCVR comprising a peptide with a sequence selected from the group consisting of SEQ ID NOs: 56-121. In a preferred embodiment, an antibody of the invention comprises a LCVR comprising a peptide with a sequence selected from the group consisting of SEQ ID NOs: 178-243 and further comprises a HCVR comprising a peptide with a sequence selected from the group consisting of SEQ ID NOs: 56-121, wherein the HCVR and LCVR present in an antibody of the invention exist together in a Fab listed in Table 1. For example, an antibody of the invention comprising an LCVR polypeptide with an amino acid sequence of SEQ ID NO: 178, preferably further comprises a HCVR polypeptide comprising an amino acid sequence selected from the group consisting of SEQ ID NOs: 56, 60, 68-93 and 95. Furthermore, an antibody of the invention comprising an LCVR polypeptide with an amino acid sequence of SEQ ID NO: 241, preferably further comprises a HCVR polypeptide comprising an amino acid sequence selected from the group consisting of SEQ ID NOs: 118 and 106. The skilled artisan will appreciate that the antibodies of the invention are not limited to the specific sequences of HCVR and LCVR as listed in Table 1 herein, but also include variants of these sequences that, when present in an anti-IL-17 antibody of the invention, retain or improve antigen binding ability and at least one other functional property of the parent antibody, e.g., epitope specificity, ability to compete with the parent antibody for binding to IL-17, $IC_{50}$ and/or $K_D$ or $k_{off}$ values for binding human IL-17.

Furthermore, a monoclonal antibody of the invention is one that is competitively inhibited from binding human IL-17 (or a portion thereof comprising DGNVDYH) by a competing monoclonal antibody wherein the competing monoclonal antibody comprises two polypeptides with the amino acid sequences shown in SEQ ID NOs: 241 (LCVR) and 118 (HCVR). Such competitive inhibition between antibodies may be measured by assays in the art, e.g., a competition ELISA assay.

Preferably, an antibody of the invention which competes with the competing antibody defined above is further characterized by specifically binding human IL-17 but not binding human IL-17B, IL-17C, IL-17D, IL-17E or IL-17F. Additionally, the antibody is further characterized by specifically binding human IL-17 and cynomolgus monkey IL-17 but not binding rat IL-17 or mouse IL-17 at levels greater than background.

More preferably, an antibody of the invention which competes for binding to human IL-17 with a competing antibody comprising amino acid sequences shown in SEQ ID NOs: 241 and 118 is further characterized by binding a human IL-17 nonlinear epitope comprising amino acids DGNVDYH (SEQ ID NO: 276). Even more preferably, an antibody of the invention which competes for binding to human IL-17 with a competing antibody comprising amino acid sequences shown in SEQ ID NOs: 241 and 118 is further characterized by having a $K_D$ for human IL-17 of less than about 7 pM, 6.5 pM or 6 pM, preferably less than about 5.5 pM, 5 pM or 4.5 pM and most preferably less than about 4 pM and/or is characterized by an $IC_{50}$, preferably in an in vitro IL-8 reporter assay, that is less than 700 pM, 650 pM, 600 pM, 560 pM, 550 pM or 500 pM, or by an $IC_{50}$ in an in vitro GROα reporter assay of less than about 560 pM, and/or has an off rate ($k_{off}$) for human IL-17 of less than $5 \times 10^{-5}$, $4 \times 10^{-5}$, $3 \times 10^{-5}$ or $2 \times 10^{-5}$ s$^{-1}$.

In one embodiment, an anti-IL-17 antibody of the invention has a heavy chain variable region and a light chain variable region, wherein the heavy chain variable region comprises CDR regions with the following amino acid sequences: CDRH1 (SEQ ID NO: 244), CDRH2 (SEQ ID NO: 245), and CDRH3 (SEQ ID NO: 246); and/or wherein the light chain variable region comprises CDR regions with the following amino acid sequences: CDRL1 (SEQ ID NO: 247), CDRL2

(SEQ ID NO: 248) and CDRL3 (SEQ ID NO: 249). Preferably, the six CDRs of an antibody of the invention exist together as in a Fab listed in Table 1 herein. Even more preferably, the heavy chain CDRS are in the context of the following framework sequences: FR1 with SEQ ID NO: 262, FR2 with SEQ ID NO: 263, FR3 with SEQ ID NO: 264 and FR4 with SEQ ID NO: 265 and the light chain CDRs are in the context of the following framework sequences: FR1 with SEQ ID NO: 266, FR2 with SEQ ID NO: 267, FR3 with SEQ ID NO: 268 and FR4 with SEQ ID NO: 269, wherein the order from the amino terminus is FR1-CDR1-F2-CDR2-FR3-CDR3-FR4.

It is further contemplated that an anti-IL-17 antibody of the invention comprises a HCVR comprising a CDRH1 comprising a sequence selected from the group consisting of SEQ ID NOs: 11-28, and/or a CDRH2 comprising a sequence selected from the group consisting of SEQ ID NOs: 29-32, and/or a CDRH3 comprising a sequence selected from the group consisting of SEQ ID NOs: 33-55 and 261. In another embodiment, an anti-IL-17 antibody of the invention comprises a LCVR comprising a CDRL1 comprising a sequence selected from the group consisting of SEQ ID NOs: 122-149, and/or a CDRL2 comprising a sequence selected from the group consisting of SEQ ID NOs: 150-167, and/or a CDRL3 comprising a sequence selected from the group consisting of SEQ ID NOs: 168-177. In a preferred embodiment, an anti-IL-17 antibody of the invention comprises a HCVR comprising a CDRH1 comprising a sequence selected from the group consisting of SEQ ID NOs: 11-28, and/or a CDRH2 comprising a sequence selected from the group consisting of SEQ ID NOs: 29-32, and/or a CDRH3 comprising a sequence selected from the group consisting of SEQ ID NOs: 33-55 and 261, and further comprises a LCVR comprising a CDRL1 comprising a sequence selected from the group consisting of SEQ ID NOs: 122-149, and/or a CDRL2 comprising a sequence selected from the group consisting of SEQ ID NOs: 150-167, and/or a CDRL3 comprising a sequence selected from the group consisting of SEQ ID NOs: 168-177.

The composition comprising a CDR of the invention will generally be an antibody heavy or light chain sequence or a substantial portion thereof, in which the CDR is located at a location consistent with Kabat numbering. The three CDR regions for each chain, heavy an light, are provided in a framework region as a contiguous sequence represented by the following formula: FR1-CDR1-FR2-CDR2-FR3-CDR3-FR4. The heavy chain or light chain FR1, FR2, FR3 and FR4 combine to form the complete framework region of an antibody when arranged as a contiguous sequence with the CDRs in the order stated. Preferably the framework regions of an antibody of the invention are of human origin or substantially of human origin (i.e., greater than about 80, 82, 85, 87, 90, 92, 95, 97%).

In a humanized antibody for therapeutic use in humans, the framework sequence is preferably entirely or substantially of human origin. Preferably the light chain framework region of a humanized, human or chimeric antibody of the invention comprises FR1 with SEQ ID NO: 266, FR2 with SEQ ID NO: 267, FR3 with SEQ ID NO: 268 and FR4 with SEQ ID NO: 269. Preferably the heavy chain framework region of a humanized, human or chimeric antibody of the invention comprises FR1 with SEQ ID NO: 262, FR2 with SEQ ID NO: 263, FR3 with SEQ ID NO: 264, and FR4 with SEQ ID NO: 265. For example, a preferred embodiment of LCVR of antibody 126 of the invention, as described in Tables 1, 2 and 3 herein comprises (polypeptides in order from N-terminus) FR1 with SEQ ID NO: 266, CDR1 with SEQ ID NO: 131, FR2 with SEQ ID NO: 267, CDR2 with SEQ ID NO: 167, FR3 with SEQ ID NO: 268, CDR3 with SEQ ID NO: 168 and FR4 with SEQ ID NO: 269. The entire LCVR sequence, operably linked to a human kappa constant region is as shown in SEQ ID NO: 274. Further, a preferred embodiment of HCVR of antibody 126 of the invention comprises (in order from N-terminus) FR1 with SEQ ID NO: 262, CDR1 with SEQ ID NO: 26, FR2 with SEQ ID NO: 262, CDR2 with SEQ ID NO: 30, FR3 with SEQ ID NO: 264, CDR3 with SEQ ID NO: 52 and FR4 with SEQ ID NO: 265. The entire HCVR sequence, operably linked to a human IgG$_4$ Fc region is as shown in SEQ ID NO: 273.

In one embodiment, an anti-IL-17 antibody of the invention, wherein all or a portion of the variable region is limited by a particular sequence as shown by a SEQ ID NO herein (see, e.g., Tables 1-3) is further characterized by being a chimeric, humanized, or fully human antibody or antigen-binding portion thereof that antagonizes or neutralizes at least one human IL-17 activity in vivo or in vitro. An IL-17 antibody of the invention, wherein all or a portion of the variable region is limited by a particular sequence as shown by a SEQ ID NO herein is further characterized by specifically binding human IL-17 but not binding human IL-17B, IL-17C, IL-17D, IL-17E or IL-17F. Additionally, the antibody is further characterized by specifically binding human IL-17 and cynomolgus monkey IL-17 but not binding rat IL-17 or mouse IL-17 at levels greater than background.

More preferably, such antibody is further characterized by binding a human IL-17 nonlinear epitope comprising amino acids DGNVDYH (SEQ ID NO: 276) wherein the antibody makes contact with the polypeptide with SEQ ID NO: 276. Even more preferably, such antibody is further characterized by having a $K_D$ for human IL-17 of less than about 7 pM, 6.5 pM or 6 pM, preferably less than about 5.5 pM, 5 pM or 4.5 pM and most preferably less than about 4 pM and/or is characterized by an $IC_{50}$, preferably in an in vitro IL-8 reporter assay, that is less than 700 pM, 650 pM, 600 pM, 560 pM, 550 pM or 500 pM, or an $IC_{50}$ in an in vitro GROα reporter assay of less than about 560 pM, and/or has an off rate ($k_{off}$) for human IL-17 of less than $5×10^{-5}$, $4×10^{-5}$, $3×10^{-5}$ or $2×10^{-5}$ s$^{-1}$.

Antibody Expression

The present invention is also directed to cell lines that express an anti-IL-17 monoclonal antibody of the invention or portion thereof. Creation and isolation of cell lines producing a monoclonal antibody of the invention can be accomplished using standard techniques known in the art. Preferred cell lines include COS, CHO, SP2/0, NS0 and yeast (available from public repositories such as ATCC, American Type Culture Collection, Manassas, Va.).

A wide variety of host expression systems can be used to express an antibody of the present invention including prokaryotic and eukaryotic expression systems (such as yeast, baculovirus, plant, mammalian and other animal cells, transgenic animals, and hybridoma cells), as well as phage display expression systems. An example of a suitable bacterial expression vector is pUC119 and a suitable eukaryotic expression vector is a modified pcDNA3.1 vector with a weakened dhfr selection system. Other antibody expression systems are also known in the art and are contemplated herein.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally the heavy chain and light chain may be expressed in different host cells. Preferably, the recombinant antibodies are secreted into the medium in which the host cells are cultured, from which the antibodies can be recovered or purified. Standard recombinant DNA methodologies are used to obtain antibody heavy and light chain genes, incorporate these genes into recombinant expression vectors, and introduce the vectors into host cells. Such standard recombinant DNA technologies are described, for example, in Sambrook, Fritsch, and Maniatis (Eds.), *Molecular Cloning, A Laboratory Manual*, Second Edition, Cold Spring Harbor, N.Y., 1989; Ausubel, et al (Eds.) *Current Protocols in Molecular Biology*, Greene Publishing Associates, 1989.

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art. See, e.g., Kabat, et al., *Sequences of Proteins of Immunological Interest*, Fifth Edition, U.S. Department of Health and Human Services, NIH Publication No. 91-3242 (1991). DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra). Alternatively, the antigen binding portion can be a Fab fragment, Fab' fragment, $F(ab')_2$ fragment, Fd, or a single chain Fv fragment (scFv). For a Fab fragment heavy chain gene, the HCVR-encoding DNA may be operably linked to another DNA molecule encoding only a heavy chain CH1 constant region.

An isolated DNA encoding a LCVR region may be converted to a full-length light chain gene (as well as to a Fab light chain gene) by operably linking the LCVR-encoding DNA to another DNA molecule encoding a light chain constant region, CL. The sequences of human light chain constant region genes are known in the art. See, e.g., Kabat, supra. DNA fragments encompassing these regions can be obtained by standard PCR amplification. The light chain constant region can be a kappa or lambda constant region.

To create an scFv gene, the HCVR- and LCVR-encoding DNA fragments are operably linked to another fragment encoding a flexible linker, e.g., encoding the amino acid sequence $(Gly_4-Ser)_3$, such that the HCVR and LCVR sequences can be expressed as a contiguous single-chain protein, with the LCVR and HCVR regions joined by the flexible linker. See, e.g., Bird, et al., *Science* 242:423-6, 1988; Huston, et al., *Proc. Natl. Acad. Sci. USA* 85:5879-83, 1988; McCafferty, et al., *Nature* 348:552-4, 1990.

In one embodiment, the invention provides a vector, preferably (but not limited to) a plasmid, a recombinant expression vector, a yeast expression vector, or a retroviral expression vector comprising a polynucleotide encoding an anti-IL-17 monoclonal antibody of the invention. Alternatively, a vector of the invention comprises a polynucleotide encoding an LCVR and/or a polynucleotide encoding an HCVR of the invention. When both an LCVR and an HCVR encoding sequence are present in the same vector, they may be transcribed independently, each from a separate promoter to which it is operably linked. If the sequences encoding the LCVR and HCVR are present in the same vector and transcribed from one promoter to which they are both operably linked, the LCVR may be 5' to the HCVR or the LCVR may be 3' to the HCVR, furthermore, the LCVR and HCVR coding region in the vector may be separated by a linker sequence of any size or content, preferably such linker, when present, is a polynucleotide encoding an internal ribosome entry site.

To express an antibody of the invention, a DNA encoding a partial or full-length light and/or heavy chain, obtained as described above, are inserted into an expression vector such that the gene is operably linked to transcriptional and translational control sequences. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the anti-IL-17 monoclonal antibody light and/or heavy chain from a host cell. The anti-IL-17 monoclonal antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, described in Urlaub and Chasin, *Proc. Natl. Acad. Sci. USA* 77:4216-20, 1980, used with a DHFR selectable marker, e.g., as described in Kaufman and Sharp, *J. Mol. Biol.* 159: 601-21, 1982] NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

Host cells can also be used to produce portions, or fragments, of intact antibodies, e.g., Fab fragments or scFv molecules by techniques that are conventional. It will be understood by a skilled artisan that variations on the above procedure are within the scope of the present invention. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to IL-17. The molecules expressed from such truncated DNA molecules are also encompassed by the antibodies of the invention.

The invention provides a host cell comprising a nucleic acid molecule of the present invention. Preferably a host cell of the invention comprises one or more vectors or constructs comprising a nucleic acid molecule of the present invention. The host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably linked to a promoter sequence. The host cell types include mammalian, bacterial, plant and yeast cells. Preferably the host cell is a CHO cell, a COS cell, a SP2/0 cell, a NS0 cell, a yeast cell or a derivative or progeny of any preferred cell type.

In a preferred system for recombinant expression of an antibody of the invention, a recombinant expression vector encoding both the antibody heavy chain and the antibody light chain is introduced into dhfr-minus CHO cells by e.g., calcium phosphate-mediated transfection. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a dhfr gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies, or antigen-binding portions thereof, of the invention can be expressed in an animal (e.g., a mouse) that is transgenic for human immunoglobulin genes (see, e.g., Taylor, et al., *Nucleic Acids Res.* 20:6287-95, 1992).

Once expressed, the intact antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90%, 92%, 94% or 96% homogeneity are preferred, and 98 to 99% or more homogeneity most preferred, for pharmaceutical uses. Once purified, partially or to homogeneity as desired, the peptides may then be used therapeutically or prophylactically, as directed herein.

Chimeric Antibody

As used herein, the term "chimeric antibody" includes monovalent, divalent or polyvalent immunoglobulins. A monovalent chimeric antibody is a dimer formed by a chimeric heavy chain associated through disulfide bridges with a chimeric light chain. A divalent chimeric antibody is a tetramer formed by two heavy chain-light chain dimers associated through at least one disulfide bridge.

A chimeric heavy chain of an antibody comprises an antigen-binding region derived from the heavy chain of a non-human antibody specific for IL-17, which is operably linked to at least a portion of a human, or substantially human (or species different from that from which the antigen-binding region was derived), heavy chain constant region such as CH1 or CH2, or preferably to a full-length heavy chain constant region. A chimeric light chain of an antibody for use in humans comprises an antigen-binding region derived entirely or substantially from the light chain of a non-human antibody specific for IL-17, operably linked to at least a portion of a human, or substantially human (or species different from that from which the antigen-binding region was derived), light chain constant region (CL), or preferably to a full-length light chain constant region. Antibodies, fragments or derivatives having chimeric heavy chains and light chains of the same or different variable region binding specificity, can also be prepared by appropriate association of the individual polypeptide chains, according to known method steps.

With this approach, hosts expressing chimeric heavy chains are separately cultured from hosts expressing chimeric light chains, and the immunoglobulin chains are separately recovered and then associated. Alternatively, the hosts can be co-cultured and the chains allowed to associate spontaneously in the culture medium, followed by recovery of the assembled immunoglobulin or fragment. Methods for producing chimeric antibodies are known in the art (see, e.g., U.S. Pat. Nos. 6,284,471; 5,807,715; 4,816,567; and 4,816, 397).

Humanized Antibodies

Preferably an antibody of the invention to be used for therapeutic purposes, would have the sequence of the framework and constant region (to the extent it exists in the antibody) derived from the mammal in which it would be used as a therapeutic so as to decrease the possibility that the mammal would illicit an immune response against the therapeutic antibody. Humanized antibodies are of particular interest since they are considered to be valuable for therapeutic application and avoid the human anti-mouse antibody response frequently observed with rodent antibodies. Additionally, in humanized antibodies the effector portion of the antibody is of human origin so it may interact better with the other parts of the human immune system (e.g., destroy the target cells more efficiently by complement-dependent cytotoxicity or antibody-dependent cellular cytotoxicity). Also, injected humanized antibodies may have a half-life more like that of naturally occurring human antibodies than do e.g., murine antibodies, thereby allowing smaller and less frequent doses to be given. The term "humanized antibody" as used herein refers to an antibody comprising portions of antibodies of different origin, wherein at least one portion is of human origin. For example, the humanized antibody can comprise portions derived from an antibody of nonhuman origin with the requisite specificity, such as a mouse, and from an antibody of human origin, joined together chemically by conventional techniques (e.g., synthetic) or prepared as a contiguous polypeptide using genetic engineering techniques.

Preferably, a "humanized antibody" has CDRs that originate (or substantially originate) from a non-human antibody (preferably a mouse monoclonal antibody) while framework and constant region, to the extent it is present, (or a significant or substantial portion thereof, i.e., at least about 90%, 92%, 94%, 95%, 96%, 97%, 98% or 99%) are encoded by nucleic acid sequence information that occurs in the human germline immunoglobulin region (see, e.g., the International ImMunoGeneTics Database) or in recombined or mutated forms thereof whether or not said antibodies are produced in human cell.

The CDRs of a humanized antibody may be altered or optimized from the CDRs of a non-human parent antibody from which they originated to generate desired properties, e.g., specificity, affinity and/or preferential binding. Altered or optimized CDRs may have amino acid substitutions, additions and/or deletions when compared to a parent CDRs, preferably about 1, 2, 3, 4, 5, 6, 7, 8, 9 or 10 total within the six CDR domains. For example, the amino acid positions of CDRs that are underlined and in bold print in Tables 2 and 3 are positions which have been altered from the CDRs as shown in Fab 1 of Tables 2 and 3. Alternatively murine antibody 2321 may be a parent antibody for comparison of CDRs of an antibody of the invention.

Humanized forms of non-human (e.g., murine) antibodies include an intact antibody, a substantially intact antibody, a portion of an antibody comprising an antigen-binding site, or a portion of an antibody comprising a Fab fragment, Fab' fragment, F(ab')$_2$, or a single chain Fv fragment. Humanized antibodies preferably contain minimal sequence derived from non-human immunoglobulin. Humanized antibodies may also comprise residues which are found neither in the recipient antibody nor in the imported CDR or framework sequences. In general, the humanized antibody will comprise substantially all of at least one, and typically two, variable domains, in which all or substantially all of the amino acids in the CDR regions correspond to those of a non-human immunoglobulin and all or substantially all of the amino acids in the FR regions are those of a human immunoglobulin consensus sequence. The humanized antibody optimally also comprises at least a portion of an immunoglobulin constant region (Fc), typically that of a human immunoglobulin. [Jones et al., Nature, 321:522-525, 1986; Riechmann et al., Nature, 332: 323-329, 1988; and Presta, Curr. Op. Struct. Biol., 2:593-596, 1992.]

Humanized antibodies may be subjected to in vitro mutagenesis using methods of routine use in the art (or, when an animal transgenic for human Ig sequences is used, in vivo somatic mutagenesis) and, thus, the framework region amino acid sequences of the HCVR and LCVR regions of the humanized recombinant antibodies are sequences that, while derived from those related to human germline HCVR and LCVR sequences, may not naturally exist within the human antibody germline repertoire in vivo. It is contemplated that such amino acid sequences of the HCVR and LCVR framework regions of the humanized recombinant antibodies are at least 90%, 92%, 94%, 95%, 96%, 98% or most preferably at least 99% identical to a human germline sequence. Preferably, those framework residues of the parent antibody (e.g., murine antibody or generally the antibody from which the humanized antibody is derived) which maintain or affect combining-site structures will be retained. These residues may be identified e.g., by X-ray crystallography of the parent antibody or Fab fragment, thereby identifying the three-dimensional structure of the antigen-binding site. One strategy to humanize antibodies is to choose a human germline sequence with the greatest homology to the framework of the parent antibody as the framework to receive the donor CDRs. This germline approach is based on the same rationale as the best-fit strategy, but only germline sequences are searched in the databases.

The humanized antibody of the present invention may comprise or be derived from a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the humanized antibody of the present invention may comprise or be derived from a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework. In other embodiments, at least FRH1, FRH2, FRH3, or FRH4 is a germline sequence (e.g., human germline) or comprises human consensus sequences for the particular framework. In preferred embodiments, all of the framework region is human framework region.

In general, humanized antibodies may be produced by obtaining nucleic acid sequences encoding the HCVR and LCVR of an antibody, e.g., a murine antibody or antibody made by a hybridoma, which binds a IL-17 epitope of the invention, identifying the CDRs in said HCVR and LCVR (nonhuman), and grafting such CDR-encoding nucleic acid sequences onto selected human framework-encoding nucleic acid sequences. Optionally, a CDR region may be optimized by mutagenizing randomly or at particular locations in order to substitute one or more amino acids in the CDR with a different amino acid prior to grafting the CDR region into the framework region. Alternatively, a CDR region may be optimized subsequent to insertion into the human framework region using methods available to one of skill in the art. Preferably, the human framework amino acid sequences are selected such that the resulting antibody is likely to be suitable for in vivo administration in humans. This can be determined, e.g., based on previous usage of antibodies containing such human framework sequence. Preferably, the human framework sequence will not itself be significantly immunogenic.

Alternatively, the amino acid sequences of the frameworks for the antibody to be humanized may be compared to those of known human framework sequences the human framework sequences to be used for CDR-grafting and selected based on their comprising sequences highly similar to those of the parent antibody, e.g., a murine antibody which binds IL-17 (e.g., an antibody comprising a HCVR with SEQ ID NO: 270 and further comprising a LCVR with SEQ ID NO: 271). Numerous human framework sequences have been isolated and their sequences reported in the art. This enhances the likelihood that the resultant CDR-grafted humanized antibody, which contains CDRs of the parent (e.g., murine) or optimized CDRs of the parent antibody grafted onto selected human frameworks (and possibly also the human constant region) will substantially retain the antigen binding structure and thus retain the binding affinity of the parent antibody. To retain a significant degree of antigen binding affinity, the selected human framework regions will preferably be those that are expected to be suitable for in vivo administration, i.e., not immunogenic.

In either method, the DNA sequence encoding the HCVR and LCVR regions of the preferably murine anti-IL-17 antibody are obtained. Methods for cloning nucleic acid sequences encoding immunoglobulins are known in the art. Such methods may, for example, involve the amplification of the immunoglobulin-encoding sequences to be cloned using appropriate primers by polymerase chain reaction (PCR). Primers suitable for amplifying immunoglobulin nucleic acid sequences, and specifically murine HCVR and LCVR sequences have been reported in the literature. After such immunoglobulin-encoding sequences have been cloned, they will be sequences by methods well known in the art.

After the CDR-encoding sequences are grafted onto the selected human framework encoding sequences, the resultant DNA sequences encoding the "humanized" variable heavy and variable light sequences are then expressed to produce a humanized Fv or humanized antibody that binds IL-17. The humanized HCVR and LCVR may be expressed as part of a whole anti-IL-17 antibody molecule, i.e., as a fusion protein with human constant domain sequences whose encoding DNA sequences have been obtained from a commercially available library or which have been obtained using, e.g., one of the above described methods for obtaining DNA sequences, or are in the art. However, the HCVR and LCVR sequences can also be expressed in the absence of constant sequences to produce a humanized anti-IL-17 Fv. Nevertheless, fusion of human constant sequences onto the variable region is potentially desirable because the resultant humanized anti-IL-17 antibody may possess human effector functions.

Methods for synthesizing DNA encoding a protein of known sequence are well known in the art. Using such methods, DNA sequences which encode the subject humanized HCVR and LCVR sequences (with or without constant regions) are synthesized, and then expressed in a vector system suitable for expression of recombinant antibodies. This may be effected in any vector system which provides for the subject humanized HCVR and LCVR sequences to be expressed as a fusion protein with human constant domain sequences and to associate to produce functional (antigen binding) antibodies or antibody fragments.

Human constant domain sequences are known in the art, and have been reported in the literature. Preferred human constant light chain sequences include the kappa and lambda constant light chain sequences. Preferred human constant heavy chain sequences include human $IgG_1$, human $IgG_2$, human $IgG_3$, human $IgG_4$ (see, e.g., Seq ID NOs: 257-260 respectively) and mutated versions thereof which provide for altered effector function, e.g., enhanced in vivo half-life, reduced Fc receptor binding, altered deamidation profile and the like.

If present, human framework regions are preferably derived from a human antibody variable region having sequence similarity to the analogous or equivalent region of the antigen binding region donor (i.e., the parent antibody). Other sources of framework regions for portions of human origin of a humanized antibody include human variable consensus sequences (see e.g., Kettleborough, C. A. et al. *Protein Engineering* 4:773-783 (1991); Carter et al., WO 94/04679. For example, the sequence of the antibody or variable region used to obtain the nonhuman portion can be compared to human sequences as described in Kabat et al. *Sequences of Proteins of Immunological Interest*, Fifth Edition, NIH, U.S. Government Printing Office (1991). In a particularly preferred embodiment, the framework regions of a humanized antibody chain are derived from a human variable region having at least about 60% overall sequence identity, preferably at least about 70%, 80%, or 90% overall sequence identity and more preferably at least about 85% overall sequence identity, with the variable region of the nonhuman donor. A human portion can also be derived from a human antibody having at least about 65% sequence identity, and preferably at least about 70% sequence identity, within the particular portion (e.g., FR) being used, when compared to the equivalent portion (e.g., FR) of the nonhuman donor.

References further describing methods involved in humanizing a mouse antibody that may be used are e.g., Queen et al., *Proc. Natl. Acad. Sci. USA* 88:2869, 1991; U.S. Pat. Nos. 5,693,761; 4,816,397; 5,225,539; computer programs ABMOD and ENCAD as described in Levitt, M., *J. Mol. Biol.* 168:595-620, 1983; humanization can be essentially performed following the method of Winter and co-workers (Jones et al., *Nature*, 321:522-525, 1986; Riechmann et al., *Nature*, 332:323-327, 1988; Verhoeyen et al., *Science*, 239: 1534-1536, 1988).

Human Antibodies

As an alternative to humanization, human antibodies can be generated. Human antibodies can be produced using various techniques known in the art, including phage display libraries (Hoogenboom and Winter, *J. Mol. Biol.*, 227:381, 1991; Marks et al., *J. Mol. Biol.*, 222:581, 1991). The techniques of Cole et al. and Boerner et al. are also available for the preparation of human monoclonal antibodies (Cole et al., Monoclonal Antibodies and *Cancer Therapy*, Alan R. Liss, p. 77 (1985) and Boerner et al., *J. Immunol.*, 147:86-95, 1991). Similarly, human antibodies can be made by introducing human immunoglobulin loci into transgenic animals, e.g., mice in which the endogenous immunoglobulin genes have been partially or complete inactivated. Upon immunization, e.g., with an antigen comprising an immunogenic epitope of the invention, a full repertoire of human antibody production is obtained, which closely resembles that seen in humans in all respects, including gene rearrangement, assembly and antibody repertoire. This approach is described, for example, in U.S. Pat. Nos. 5,545,807; 5,545,806; 5,569,825; 5,589,369; 5,591,669; 5,625,126; 5,633,425; 5,661,016, and in the following scientific publications: Marks et al., *BioTechnology* 10:779-783, 1992; Lonberg et al., *Nature* 368: 856-859, 1994; Morrison, *Nature* 368: 812-13, 1994; Fishwild et al., *Nature Biotechnology* 14:845-51, 1996; Neuberger, *Nature Biotechnology* 14: 826 (1996); Lonberg and Huszar, *Intern. Rev. Immunol.* 13: 65-93 (1995) and Jobkobovits et al., *Proc. Natl. Acad. Sci. USA*, 90:2551, 1993.

Human immunoglobulin genes introduced into the mouse, thus creating transgenic mice capable of responding to antigens with antibodies having human sequences are also described in Bruggemann et al. (*Proc. Nat'l. Acad. Sci. USA* 86:6709-6713, 1989). There are several strategies that exist for the generation of mammals that produce human antibodies. In particular, there is the "minilocus" approach in which an exogenous Ig locus is mimicked through the inclusion of pieces (e.g., individual genes) from the Ig locus (see, e.g., U.S. Pat. Nos. 5,545,807, 5,545,806, 5,625,825, 5,625,126, 5,633,425, 5,661,016, 5,770,429, 5,789,650, and 5,814,318, 5,612,205, 5,721,367, 5,789,215), YAC introduction of large and substantially germline fragments of the Ig loci (See Mendez et al. *Nature Genetics* 15:146-156, 1997; Green and Jakobovits *J. Exp. Med.* 188:483-495, 1998), and introduction of entire or substantially entire loci through the use of microcell fusion (see European Patent Application No. EP 0 843 961 A1).

Any transgenic mouse capable of responding to immunization with antibodies having human sequences may be used to produce an anti-IL-17 antibody of the invention when using methods available to one skilled in the art, e.g., when such mouse is immunized with a polypeptide comprising an immunogenic epitope of the invention.

Uses

Antibodies of the present invention are useful in therapeutic, prophylactic, diagnostic and research applications as described herein. An antibody of the invention may be used to diagnose a disorder or disease associated with the expression of human IL-17. In a similar manner, the antibody of the invention can be used in an assay to monitor IL-17 levels in a subject being tested for an IL-17-associated condition. Research applications include methods that utilize the antibody of the invention and a label to detect IL-17 in a sample, e.g., in a human body fluid or in a cell or tissue extract. Antibodies of the invention may by used with or without modification, and are labeled by covalent or non-covalent attachment of a detectable moiety. The detectable moiety can be any one that is capable of producing, either directly or indirectly, a detectable signal. For example, the detectable moiety may be a radioisotope such as, e.g., $^{3}H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, beta-galactosidase, or horseradish peroxidase. Any method known in the art for separately conjugating the antibody to the detectable moiety may be employed, including those methods described by Hunter, et al., *Nature* 144:945, 1962; David, et al., *Biochemistry* 13: 1014, 1974; Pain, et al., *J. Immunol. Meth.* 40: 219, 1981; and Nygren, J. *Histochem. and Cytochem.* 30: 407, 1982.

A variety of conventional protocols for measuring IL-17, including e.g., ELISAs, RIAs, and FACS, are known in the art and provide a basis for diagnosing altered or abnormal levels of IL-17 expression. Normal or standard expression values are established using any art known technique, e.g., by combining a sample comprising a IL-17 polypeptide with, e.g., antibodies under conditions suitable to form a antigen:antibody complex. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of a radioactive material include $^{125}I$, $^{131}I$, $^{35}S$, or $^{3}H$. (See, e.g., Zola, *Monoclonal Antibodies: A Manual of Techniques*, CRC Press, Inc. (1987)). The amount of a standard complex formed is quantitated by various methods, such as, e.g., photometric means. Amounts of IL-17 polypeptide expressed in samples are then compared with the standard values.

As a matter of convenience, the antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a blocking buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic Uses for the Antibody

IL-17 is a pro-inflammatory cytokine secreted by activated T cells at sites of inflammation, not in the systemic circulation; it is not readily detectable in the serum or tissues of a healthy person. IL-17 upregulates adhesion molecules, induces production of multiple inflammatory cytokines and chemokines from various cell types including synoviocytes, chondroctes, fibroblasts, endothelial cells, epithelial cells, thereby inducing recruitment of neutrophils to an inflammatory site, stimulates the production of prostaglandins and metalloproteinases, and inhibits proteoglycan synthesis. Furthermore, IL-17 plays an important role in the maturation of hematopoietic progenitor cells. IL-17 has signaling roles in different organs and tissues including lung, articular cartilage, bone, brain, hematopoietic cells, kidney, skin and intestine. IL-17 shares 15-27% amino acid homology with IL-17 B, C and E and 44-50% amino acid homology with IL-17 D and F. IL-17 binds to the IL-17 receptor with low affinity (about 1 nM), while other IL-17 family members do not bind to the IL-17 receptor.

Increased levels of IL-17 (i.e., IL-17A) have been associated with several conditions including airway inflammation, RA, osteoarthritis, bone erosion, intraperitoneal abscesses and adhesions, IBD, allograft rejection, psoriasis, certain types of cancer, angiogenesis, atherosclerosis and MS. Both IL-17 and IL-17R are up-regulated in the synovial tissue of RA patients. IL-17 exerts its role in pathogenesis of RA through IL-1-β and TNF-α dependent and independent pathways. IL-17 stimulates secretion of other cytokines and chemokines, e.g., TNF-α, IL-1β, IL-6, IL-8 and Gro-α. IL-17 directly contributes to disease progression in RA. Injection of IL-17 into the mouse knee promotes joint destruction independently of IL-1β activity (Ann. Rheum. Dis. 59:529-32, 2000). Anti-IL-1β antibody has no effect on IL-17 induced inflammation and joint damage (J. Immunol. 167:1004-1013, 2001). In an SCW-induced murine arthritis model, IL-17 induced inflammatory cell infiltration and proteoglycan depletion in wild-type and IL-1β knock out and TNF-α knock out mice. IL-17 knock out mice are phenotypically normal in the absence of antigenic challenge, but have markedly reduced arthritis following type II collagen immunization (J. Immunol. 171:6173-6177, 2003).

Multiple sclerosis ("MS") is an autoimmune disease characterized by central nervous system ("CNS") inflammation with damage to the myelin sheath surrounding axons. A hallmark of MS is that T cells infiltrate into the CNS. MS affects more than 350,000 persons in the U.S. and 2.5 million worldwide. There are many forms and the most common is relapsing/remitting disease ("RRMS") followed by a secondary progressive stage. Current therapeutics consist of Interferon-β (AVONEX, BETASERON and REBIF) that reduces the relapse/exacerbation rate by 31%-34%, but may produce flu-like symptoms and/or synthesis of neutralizing antibodies (e.g., about 15% of patients receiving AVONEX produce neutralizing antibodies in 18 months. TYSABRI, approved by the FDA for RRMS was subsequently removed from the market due to CNS immunosuppression concerns. There is still an unmet medical need in the treatment of MS. IL-17 mRNA is increased in MS lesions and in mononuclear cells (MNC) in blood and cerebrospinal fluid from MS patients. Higher numbers of IL-17 mRNA-expressing blood MNC are detected during MS clinical exacerbation compared to remission (Multiple Sclerosis, 5:101-104, 1999). Furthermore, experimental autoimmune encephalomyelitis ("EAE"), a preclinical animal model for MS is significantly suppressed in IL-17 knockout mice.

Therefore, a pharmaceutical composition comprising an anti-IL-17 monoclonal antibody of the invention may be useful for the treatment or prevention of conditions wherein the presence of IL-17 causes or contributes to undesirable pathological effects or decrease of IL-17 activity has a therapeutic benefit in mammals, preferably humans, including, but not limited to, airway inflammation, asthma, RA, osteoarthritis, bone erosion, intraperitoneal abscesses and adhesions, IBD, allograft rejection, psoriasis, certain types of cancer, angiogenesis, atherosclerosis and MS, as well as other inflammatory disorders, conditions, diseases or states including without limit: erythematosus, response to allergen exposure, *Helicobacter pylori* associated gastritis, bronchial asthma, and allograft rejection (e.g., renal), systemic lupus erythematosis and lupus nephritis. The use of an anti-IL-17 monoclonal antibody of the present invention for treating or preventing of at least one of the aforementioned disorders in which IL-17 activity is detrimental or which benefits for decreased levels of bioactive IL-17 is contemplated herein. Additionally, the use of an anti-IL-17 monoclonal antibody of the present invention for use in the manufacture of a medicament for the treatment of at least one of the aforementioned disorders is contemplated.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, includes administration of a compound of the present invention for treatment of a disease or condition in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease or disorder or alleviating symptoms or complications thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

Pharmaceutical Composition

An antibody of the invention can be incorporated into pharmaceutical compositions suitable for administration to a subject (see, e.g., Example 14). The compounds of the invention may be administered alone or in combination with a pharmaceutically acceptable carrier, diluent, and/or excipient, in single or multiple doses. The pharmaceutical compositions for administration are designed to be appropriate for the selected mode of administration, and pharmaceutically acceptable diluent, carrier, and/or excipients such as dispersing agents, buffers, surfactants, preservatives, solubilizing agents, isotonicity agents, stabilizing agents and the like are used as appropriate (See, e.g., Example 14 herein). Said compositions are designed in accordance with conventional techniques as in e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners.

A pharmaceutical composition comprising an anti-IL-17 monoclonal antibody of the present invention can be administered to a subject at risk for or exhibiting pathologies as described herein using standard administration techniques including oral, intravenous, intraperitoneal, subcutaneous, pulmonary, transdermal, intramuscular, intranasal, buccal, sublingual, or suppository administration.

A pharmaceutical composition of the invention preferably is a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effect of the antibody, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically-effective or prophylactically-effective amount is at least the minimal dose, but less than a toxic dose, of an active agent which is necessary to impart therapeutic benefit to a subject. Stated another way, a therapeutically-effective amount of an antibody of the invention is an amount which in mammals, preferably humans, decreases an IL-17 bioactivity, e.g., binding to IL17R, wherein the presence of IL-17 causes or contributes to undesirable pathological effects or decrease in IL-17 levels results in a beneficial therapeutic effect in a mammal, preferably a human.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are straightforward in the art.

The pharmaceutical composition typically must be sterile and stable under the conditions of manufacture and storage in the container provided, including e.g., a sealed vial or syringe. Therefore, pharmaceutical compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/ml, or more) of antibody concentration. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 0.001 to 1000 μg; however, doses below or above this exemplary range are envisioned, especially considering the aforementioned factors. The daily parenteral dosage regimen can be about 0.1 μg/kg to about 100 mg/kg of total body weight, preferably from about 0.3 μg/kg to about 10 mg/kg and more preferably from about 1 μg/kg to 1 mg/kg, even more preferably from about 0.5 to 10 mg/kg body weight per day. Progress may be monitored by periodic assessment. For repeated administrations over several days or longer, depending on the condition, the treatment is repeated until a desired suppression of disease symptoms occurs. However, other dosage regimens may be useful and are not excluded herefrom. The desired dosage can be delivered by a single bolus administration, by multiple bolus administrations, or by continuous infusion administration of antibody, depending on the pattern of pharmacokinetic decay that the practitioner wishes to achieve.

These suggested amounts of antibody are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate. Generally, pH between 6 and 8 is preferred.

Article of Manufacture

In another embodiment of the invention, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of an antibody of the invention which is effective for preventing or treating the disorder or condition and may have a sterile access port (for example the container may be an intravenous solution bag or a vial having a stopper pierceable by a hypodermic injection needle). The active agent in the composition is an anti-IL-17 antibody of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

TABLE 1

| | | SEQ ID NUMBERS | | | | | | |
|---|---|---|---|---|---|---|---|---|
| Fab # | LCVR | Light CDR1 | Light CDR2 | Light CDR3 | HCVR | H-CDR1 | H-CDR2 | H-CDR3 |
| 1 | 178 | 122 | 150 | 168 | 56 | 11 | 29 | 33 |
| 2 | 179 | 122 | 150 | 169 | 57 | 11 | 29 | 34 |
| 3 | 180 | 123 | 150 | 168 | 56 | 11 | 29 | 33 |
| 4 | 181 | 124 | 150 | 168 | 58 | 11 | 29 | 35 |
| 5 | 179 | 122 | 150 | 169 | 59 | 11 | 29 | 36 |
| 6 | 182 | 124 | 150 | 169 | 60 | 11 | 29 | 37 |
| 7 | 183 | 125 | 150 | 170 | 56 | 11 | 29 | 33 |
| 8 | 184 | 124 | 150 | 171 | 61 | 11 | 29 | 38 |
| 9 | 185 | 124 | 150 | 170 | 62 | 11 | 29 | 39 |
| 10 | 178 | 122 | 150 | 168 | 60 | 11 | 29 | 37 |

TABLE 1-continued

| | | | | SEQ ID NUMBERS | | | | |
|---|---|---|---|---|---|---|---|---|
| Fab # | LCVR | Light CDR1 | Light CDR2 | Light CDR3 | HCVR | H-CDR1 | H-CDR2 | H-CDR3 |
| 11 | 181 | 124 | 150 | 168 | 61 | 11 | 29 | 38 |
| 12 | 186 | 124 | 150 | 172 | 63 | 11 | 29 | 40 |
| 13 | 187 | 123 | 150 | 169 | 64 | 11 | 29 | 41 |
| 14 | 188 | 123 | 150 | 173 | 65 | 11 | 29 | 42 |
| 15 | 189 | 124 | 150 | 174 | 66 | 11 | 29 | 43 |
| 16 | 181 | 124 | 150 | 168 | 62 | 11 | 29 | 39 |
| 17 | 187 | 123 | 150 | 169 | 61 | 11 | 29 | 38 |
| 18 | 181 | 124 | 150 | 168 | 67 | 11 | 29 | 44 |
| 19 | 190 | 124 | 150 | 175 | 56 | 11 | 29 | 33 |
| 20 | 178 | 122 | 150 | 168 | 68 | 12 | 29 | 33 |
| 21 | 178 | 122 | 150 | 168 | 69 | 13 | 29 | 33 |
| 22 | 178 | 122 | 150 | 168 | 70 | 14 | 29 | 33 |
| 23 | 178 | 122 | 150 | 168 | 71 | 15 | 29 | 33 |
| 24 | 178 | 122 | 150 | 168 | 72 | 16 | 29 | 33 |
| 25 | 178 | 122 | 150 | 168 | 73 | 17 | 29 | 33 |
| 26 | 178 | 122 | 150 | 168 | 74 | 18 | 29 | 33 |
| 27 | 178 | 122 | 150 | 168 | 75 | 19 | 29 | 33 |
| 28 | 178 | 122 | 150 | 168 | 76 | 20 | 29 | 33 |
| 29 | 178 | 122 | 150 | 168 | 77 | 21 | 29 | 33 |
| 30 | 178 | 122 | 150 | 168 | 78 | 22 | 29 | 33 |
| 31 | 178 | 122 | 150 | 168 | 79 | 23 | 29 | 33 |
| 32 | 178 | 122 | 150 | 168 | 80 | 24 | 29 | 33 |
| 33 | 178 | 122 | 150 | 168 | 81 | 11 | 30 | 33 |
| 34 | 178 | 122 | 150 | 168 | 82 | 11 | 31 | 33 |
| 35 | 178 | 122 | 150 | 168 | 83 | 11 | 32 | 33 |
| 36 | 178 | 122 | 150 | 168 | 58 | 11 | 29 | 35 |
| 37 | 178 | 122 | 150 | 168 | 84 | 11 | 29 | 45 |
| 38 | 178 | 122 | 150 | 168 | 85 | 11 | 29 | 261 |
| 39 | 178 | 122 | 150 | 168 | 86 | 11 | 29 | 47 |
| 40 | 178 | 122 | 150 | 168 | 87 | 11 | 29 | 48 |
| 41 | 178 | 122 | 150 | 168 | 88 | 11 | 29 | 49 |
| 42 | 178 | 122 | 150 | 168 | 89 | 11 | 29 | 50 |
| 43 | 178 | 122 | 150 | 168 | 90 | 11 | 29 | 51 |
| 44 | 178 | 122 | 150 | 168 | 91 | 11 | 29 | 52 |
| 45 | 178 | 122 | 150 | 168 | 92 | 11 | 29 | 53 |
| 46 | 178 | 122 | 150 | 168 | 93 | 11 | 29 | 54 |
| 47 | 191 | 125 | 150 | 168 | 56 | 11 | 29 | 33 |
| 48 | 192 | 126 | 150 | 168 | 56 | 11 | 29 | 33 |
| 49 | 193 | 127 | 150 | 168 | 56 | 11 | 29 | 33 |
| 50 | 194 | 128 | 150 | 168 | 56 | 11 | 29 | 33 |
| 51 | 195 | 129 | 150 | 168 | 56 | 11 | 29 | 33 |
| 52 | 196 | 130 | 150 | 168 | 56 | 11 | 29 | 33 |
| 53 | 197 | 131 | 150 | 168 | 56 | 11 | 29 | 33 |
| 54 | 198 | 132 | 150 | 168 | 56 | 11 | 29 | 33 |
| 55 | 199 | 133 | 150 | 168 | 56 | 11 | 29 | 33 |
| 56 | 200 | 134 | 150 | 168 | 56 | 11 | 29 | 33 |
| 57 | 201 | 135 | 150 | 168 | 56 | 11 | 29 | 33 |
| 58 | 202 | 136 | 150 | 168 | 56 | 11 | 29 | 33 |
| 59 | 203 | 137 | 150 | 168 | 56 | 11 | 29 | 33 |
| 60 | 204 | 138 | 150 | 168 | 56 | 11 | 29 | 33 |
| 61 | 205 | 139 | 150 | 168 | 56 | 11 | 29 | 33 |
| 62 | 206 | 140 | 150 | 168 | 56 | 11 | 29 | 33 |
| 63 | 199 | 133 | 150 | 168 | 56 | 11 | 29 | 33 |
| 64 | 207 | 141 | 150 | 168 | 56 | 11 | 29 | 33 |
| 65 | 208 | 142 | 150 | 168 | 56 | 11 | 29 | 33 |
| 66 | 209 | 143 | 150 | 168 | 56 | 11 | 29 | 33 |
| 67 | 210 | 144 | 150 | 168 | 56 | 11 | 29 | 33 |
| 68 | 211 | 122 | 151 | 168 | 56 | 11 | 29 | 33 |
| 69 | 212 | 122 | 150 | 176 | 56 | 11 | 29 | 33 |
| 70 | 213 | 122 | 150 | 177 | 56 | 11 | 29 | 33 |
| 71 | 214 | 145 | 150 | 168 | 94 | 25 | 29 | 46 |
| 72 | 191 | 125 | 150 | 168 | 95 | 26 | 29 | 46 |
| 73 | 215 | 146 | 150 | 168 | 96 | 26 | 29 | 55 |
| 74 | 199 | 133 | 150 | 168 | 97 | 26 | 29 | 48 |
| 75 | 178 | 122 | 150 | 168 | 95 | 26 | 29 | 46 |
| 76 | 199 | 133 | 150 | 168 | 95 | 26 | 29 | 46 |
| 78 | 178 | 122 | 150 | 168 | 98 | 26 | 29 | 47 |
| 79 | 195 | 129 | 150 | 168 | 99 | 27 | 29 | 46 |
| 80 | 195 | 129 | 150 | 168 | 97 | 26 | 29 | 48 |
| 82 | 199 | 133 | 150 | 168 | 98 | 26 | 29 | 47 |
| 84 | 199 | 133 | 150 | 168 | 100 | 26 | 29 | 52 |
| 85 | 191 | 125 | 150 | 168 | 98 | 26 | 29 | 47 |
| 86 | 191 | 125 | 150 | 168 | 95 | 26 | 29 | 46 |
| 87 | 216 | 147 | 150 | 168 | 95 | 26 | 29 | 46 |

TABLE 1-continued

| Fab # | LCVR | Light CDR1 | Light CDR2 | Light CDR3 | HCVR | H-CDR1 | H-CDR2 | H-CDR3 |
|---|---|---|---|---|---|---|---|---|
| 88 | 199 | 133 | 150 | 168 | 94 | 25 | 29 | 46 |
| 89 | 196 | 130 | 150 | 168 | 100 | 26 | 29 | 52 |
| 91 | 195 | 129 | 150 | 168 | 97 | 26 | 29 | 48 |
| 92 | 216 | 147 | 150 | 168 | 97 | 26 | 29 | 48 |
| 93 | 195 | 129 | 150 | 168 | 101 | 27 | 29 | 48 |
| 94 | 199 | 133 | 150 | 168 | 95 | 26 | 29 | 46 |
| 95 | 217 | 130 | 152 | 168 | 98 | 26 | 29 | 47 |
| 96 | 218 | 125 | 153 | 168 | 102 | 26 | 32 | 46 |
| 97 | 219 | 145 | 154 | 168 | 97 | 26 | 29 | 48 |
| 98 | 199 | 133 | 150 | 168 | 98 | 26 | 29 | 47 |
| 99 | 199 | 133 | 150 | 168 | 95 | 26 | 29 | 46 |
| 100 | 220 | 125 | 155 | 168 | 103 | 26 | 32 | 33 |
| 101 | 221 | 133 | 156 | 168 | 95 | 26 | 29 | 46 |
| 102 | 222 | 148 | 157 | 168 | 95 | 26 | 29 | 46 |
| 103 | 223 | 130 | 158 | 168 | 104 | 26 | 32 | 46 |
| 104 | 224 | 145 | 159 | 168 | 104 | 26 | 32 | 46 |
| 105 | 225 | 130 | 150 | 169 | 105 | 26 | 32 | 47 |
| 106 | 226 | 133 | 160 | 168 | 106 | 26 | 29 | 47 |
| 107 | 227 | 130 | 161 | 169 | 107 | 25 | 32 | 48 |
| 108 | 228 | 133 | 162 | 169 | 108 | 25 | 29 | 47 |
| 109 | 229 | 130 | 163 | 168 | 109 | 27 | 32 | 46 |
| 110 | 230 | 131 | 164 | 169 | 100 | 26 | 29 | 52 |
| 111 | 231 | 146 | 165 | 168 | 95 | 26 | 29 | 46 |
| 112 | 232 | 125 | 166 | 168 | 97 | 26 | 29 | 48 |
| 113 | 199 | 133 | 150 | 168 | 110 | 27 | 29 | 47 |
| 114 | 233 | 129 | 159 | 168 | 106 | 26 | 29 | 47 |
| 115 | 234 | 133 | 167 | 168 | 106 | 26 | 29 | 47 |
| 116 | 235 | 149 | 167 | 168 | 110 | 27 | 29 | 47 |
| 117 | 236 | 125 | 167 | 168 | 111 | 28 | 32 | 53 |
| 118 | 234 | 133 | 167 | 168 | 112 | 26 | 30 | 53 |
| 119 | 237 | 122 | 167 | 168 | 100 | 26 | 29 | 52 |
| 120 | 238 | 122 | 167 | 169 | 112 | 26 | 30 | 46 |
| 121 | 239 | 147 | 167 | 169 | 113 | 28 | 32 | 46 |
| 122 | 237 | 122 | 167 | 168 | 114 | 26 | 30 | 53 |
| 123 | 236 | 125 | 167 | 168 | 115 | 26 | 29 | 53 |
| 124 | 240 | 131 | 167 | 168 | 116 | 11 | 30 | 53 |
| 125 | 178 | 122 | 150 | 168 | 117 | 26 | 32 | 52 |
| 126 | 241 | 131 | 167 | 168 | 118 | 26 | 30 | 52 |
| 127 | 241 | 131 | 167 | 168 | 106 | 26 | 29 | 47 |
| 128 | 242 | 129 | 167 | 169 | 119 | 27 | 30 | 47 |
| 129 | 236 | 125 | 167 | 168 | 120 | 26 | 30 | 52 |
| 130 | 243 | 129 | 167 | 168 | 119 | 27 | 30 | 47 |
| 131 | 236 | 125 | 167 | 168 | 117 | 26 | 32 | 52 |
| 132 | 236 | 125 | 167 | 168 | 121 | 27 | 30 | 52 |

TABLE 2

Heavy Chain CDR Alignments

| Fab# | CDR1 | SEQ ID No. | CDR2 | Seq ID No. | CDR3 | Seq ID No. |
|---|---|---|---|---|---|---|
| 1 | GYSFTDYNMN | 11 | VINPNYGTTDYNQRFKG | 29 | YDYATGTGAY | 33 |
| 2 | GYSFTDYNMN | 11 | VINPNYGTTDYNQRFKG | 29 | YDYWTGTGGY | 34 |
| 3 | GYSFTDYNMN | 11 | VINPNYGTTDYNQRFKG | 29 | YDYATGTGAY | 33 |
| 4 | GYSFTDYNMN | 11 | VINPNYGTTDYNQRFKG | 29 | YDYWTGTGAY | 35 |
| 5 | GYSFTDYNMN | 11 | VINPNYGTTDYNQRFKG | 29 | YDYATGTGLY | 36 |
| 6 | GYSFTDYNMN | 11 | VINPNYGTTDYNQRFKG | 29 | YDYATGTGGY | 37 |
| 7 | GYSFTDYNMN | 11 | VINPNYGTTDYNQRFKG | 29 | YDYATGTGAY | 33 |
| 8 | GYSFTDYNMN | 11 | VINPNYGTTDYNQRFKG | 29 | YDYATGTGVY | 38 |
| 9 | GYSFTDYNMN | 11 | VINPNYGTTDYNQRFKG | 29 | YDYHTGTGGY | 39 |
| 10 | GYSFTDYNMN | 11 | VINPNYGTTDYNQRFKG | 29 | YDYATGTGGY | 37 |

TABLE 2-continued

Heavy Chain CDR Alignments

| Fab# | CDR1 | SEQ ID No. | CDR2 | Seq ID No. | CDR3 | Seq ID No. |
|---|---|---|---|---|---|---|
| 11 | GYSFTDYNMN | 11 | VINPNYGTTDYNQRFKG | 29 | YDYATGTGVY | 38 |
| 12 | GYSFTDYNMN | 11 | VINPNYGTTDYNQRFKG | 29 | YDYATGTGTY | 40 |
| 13 | GYSFTDYNMN | 11 | VINPNYGTTDYNQRFKG | 29 | YDYFTGTGGY | 41 |
| 14 | GYSFTDYNMN | 11 | VINPNYGTTDYNQRFKG | 29 | YDYFTGTGPY | 42 |
| 15 | GYSFTDYNMN | 11 | VINPNYGTTDYNQRFKG | 29 | YDYYTGTGGY | 43 |
| 16 | GYSFTDYNMN | 11 | VINPNYGTTDYNQRFKG | 29 | YDYHTGTGGY | 39 |
| 17 | GYSFTDYNMN | 11 | VINPNYGTTDYNQRFKG | 29 | YDYATGTGVY | 38 |
| 18 | GYSFTDYNMN | 11 | VINPNYGTTDYNQRFKG | 29 | YDYSTGTGGY | 44 |
| 19 | GYSFTDYNMN | 11 | VINPNYGTTDYNQRFKG | 29 | YDYATGTGAY | 33 |
| 20 | GYSFTDYNIN | 12 | VINPNYGTTDYNQRFKG | 29 | YDYATGTGAY | 33 |
| 21 | GYSFTDYNLN | 13 | VINPNYGTTDYNQRFKG | 29 | YDYATGTGAY | 33 |
| 22 | GYSFGDYNMN | 14 | VINPNYGTTDYNQRFKG | 29 | YDYATGTGAY | 33 |
| 23 | GYSFRDYNMN | 15 | VINPNYGTTDYNQRFKG | 29 | YDYATGTGAY | 33 |
| 24 | GYSFTWYNMN | 16 | VINPNYGTTDYNQRFKG | 29 | YDYATGTGAY | 33 |
| 25 | GYSFNDYNMN | 17 | VINPNYGTTDYNQRFKG | 29 | YDYATGTGAY | 33 |
| 26 | GYSFTDYNMS | 18 | VINPNYGTTDYNQRFKG | 29 | YDYATGTGAY | 33 |
| 27 | GYSFTDYNTN | 19 | VINPNYGTTDYNQRFKG | 29 | YDYATGTGAY | 33 |
| 28 | GYSFPDYNMN | 20 | VINPNYGTTDYNQRFKG | 29 | YDYATGTGAY | 33 |
| 29 | HYSFTDYNMN | 21 | VINPNYGTTDYNQRFKG | 29 | YDYATGTGAY | 33 |
| 30 | GYHFTDYNMN | 22 | VINPNYGTTDYNQRFKG | 29 | YDYATGTGAY | 33 |
| 31 | GYPFTDYNMN | 23 | VINPNYGTTDYNQRFKG | 29 | YDYATGTGAY | 33 |
| 32 | GYSFTDFNMN | 24 | VINPNYGTTDYNQRFKG | 29 | YDYATGTGAY | 33 |
| 33 | GYSFTDYNMN | 11 | VINPMYGTTDYNQRFKG | 30 | YDYATGTGAY | 33 |
| 34 | GYSFTDYNMN | 11 | VINPAYGTTDYNQRFKG | 31 | YDYATGTGAY | 33 |
| 35 | GYSFTDYNMN | 11 | VINPEYGTTDYNQRFKG | 32 | YDYATGTGAY | 33 |
| 36 | GYSFTDYNMN | 11 | VINPNYGTTDYNQRFKG | 29 | YDYWTGTGAY | 35 |
| 37 | GYSFTDYNMN | 11 | VINPNYGTTDYNQRFKG | 29 | YDYSTGTGAY | 45 |
| 38 | GYSFTDYNMN | 11 | VINPNYGTTDYNQRFKG | 29 | YDAFTGTGAY | 261 |
| 39 | GYSFTDYNMN | 11 | VINPNYGTTDYNQRFKG | 29 | YDYYTGTGAY | 47 |
| 40 | GYSFTDYNMN | 11 | VINPNYGTTDYNQRFKG | 29 | YDYHTGTGAY | 48 |
| 41 | GYSFTDYNMN | 11 | VINPNYGTTDYNQRFKG | 29 | YDYLTGTGAY | 49 |
| 42 | GYSFTDYNMN | 11 | VINPNYGTTDYNQRFKG | 29 | YDYATSTGAY | 50 |
| 43 | GYSFTDYNMN | 11 | VINPNYGTTDYNQRFKG | 29 | YDYAPGTGAY | 51 |
| 44 | GYSFTDYNMN | 11 | VINPNYGTTDYNQRFKG | 29 | YDYFTGTGVY | 52 |
| 45 | GYSFTDYNMN | 11 | VINPNYGTTDYNQRFKG | 29 | YDYYTGTGVY | 53 |
| 46 | GYSFTDYNMN | 11 | VINPNYGTTDYNQRFKG | 29 | YDPATGTGAY | 54 |
| 47 | GYSFTDYNMN | 11 | VINPNYGTTDYNQRFKG | 29 | YDYATGTGAY | 33 |

TABLE 2-continued

Heavy Chain CDR Alignments

| Fab# | CDR1 | SEQ ID No. | CDR2 | Seq ID No. | CDR3 | Seq ID No. |
|---|---|---|---|---|---|---|
| 48 | GYSFTDYNMN | 11 | VINPNYGTTDYNQRFKG | 29 | YDYATGTGAY | 33 |
| 49 | GYSFTDYNMN | 11 | VINPNYGTTDYNQRFKG | 29 | YDYATGTGAY | 33 |
| 50 | GYSFTDYNMN | 11 | VINPNYGTTDYNQRFKG | 29 | YDYATGTGAY | 33 |
| 51 | GYSFTDYNMN | 11 | VINPNYGTTDYNQRFKG | 29 | YDYATGTGAY | 33 |
| 52 | GYSFTDYNMN | 11 | VINPNYGTTDYNQRFKG | 29 | YDYATGTGAY | 33 |
| 53 | GYSFTDYNMN | 11 | VINPNYGTTDYNQRFKG | 29 | YDYATGTGAY | 33 |
| 54 | GYSFTDYNMN | 11 | VINPNYGTTDYNQRFKG | 29 | YDYATGTGAY | 33 |
| 55 | GYSFTDYNMN | 11 | VINPNYGTTDYNQRFKG | 29 | YDYATGTGAY | 33 |
| 56 | GYSFTDYNMN | 11 | VINPNYGTTDYNQRFKG | 29 | YDYATGTGAY | 33 |
| 57 | GYSFTDYNMN | 11 | VINPNYGTTDYNQRFKG | 29 | YDYATGTGAY | 33 |
| 58 | GYSFTDYNMN | 11 | VINPNYGTTDYNQRFKG | 29 | YDYATGTGAY | 33 |
| 59 | GYSFTDYNMN | 11 | VINPNYGTTDYNQRFKG | 29 | YDYATGTGAY | 33 |
| 60 | GYSFTDYNMN | 11 | VINPNYGTTDYNQRFKG | 29 | YDYATGTGAY | 33 |
| 61 | GYSFTDYNMN | 11 | VINPNYGTTDYNQRFKG | 29 | YDYATGTGAY | 33 |
| 62 | GYSFTDYNMN | 11 | VINPNYGTTDYNQRFKG | 29 | YDYATGTGAY | 33 |
| 63 | GYSFTDYNMN | 11 | VINPNYGTTDYNQRFKG | 29 | YDYATGTGAY | 33 |
| 64 | GYSFTDYNMN | 11 | VINPNYGTTDYNQRFKG | 29 | YDYATGTGAY | 33 |
| 65 | GYSFTDYNMN | 11 | VINPNYGTTDYNQRFKG | 29 | YDYATGTGAY | 33 |
| 66 | GYSFTDYNMN | 11 | VINPNYGTTDYNQRFKG | 29 | YDYATGTGAY | 33 |
| 67 | GYSFTDYNMN | 11 | VINPNYGTTDYNQRFKG | 29 | YDYATGTGAY | 33 |
| 68 | GYSFTDYNMN | 11 | VINPNYGTTDYNQRFKG | 29 | YDYATGTGAY | 33 |
| 69 | GYSFTDYNMN | 11 | VINPNYGTTDYNQRFKG | 29 | YDYATGTGAY | 33 |
| 70 | GYSFTDYNMN | 11 | VINPNYGTTDYNQRFKG | 29 | YDYATGTGAY | 33 |
| 71 | GYSFTDYHLG | 25 | VINPNYGTTDYNQRFKG | 29 | YDYFTGTGAY | 46 |
| 72 | GYSFTDYHIH | 26 | VINPNYGTTDYNQRFKG | 29 | YDYFTGTGAY | 46 |
| 73 | GYSFTDYHIH | 26 | VINPNYGTTDYNQRFKG | 29 | YDYHTGTGVY | 55 |
| 74 | GYSFTDYHIH | 26 | VINPNYGTTDYNQRFKG | 29 | YDYHTGTGAY | 48 |
| 75 | GYSFTDYHIH | 26 | VINPNYGTTDYNQRFKG | 29 | YDYFTGTGAY | 46 |
| 76 | GYSFTDYHIH | 26 | VINPNYGTTDYNQRFKG | 29 | YDYFTGTGAY | 46 |
| 78 | GYSFTDYHIH | 26 | VINPNYGTTDYNQRFKG | 29 | YDYYTGTGAY | 47 |
| 79 | GYSFTDYHMS | 27 | VINPNYGTTDYNQRFKG | 29 | YDYFTGTGAY | 46 |
| 80 | GYSFTDYHIH | 26 | VINPNYGTTDYNQRFKG | 29 | YDYHTGTGAY | 48 |
| 82 | GYSFTDYHIH | 26 | VINPNYGTTDYNQRFKG | 29 | YDYYTGTGAY | 47 |
| 84 | GYSFTDYHIH | 26 | VINPNYGTTDYNQRFKG | 29 | YDYFTGTGVY | 52 |
| 85 | GYSFTDYHIH | 26 | VINPNYGTTDYNQRFKG | 29 | YDYYTGTGAY | 47 |
| 86 | GYSFTDYHIH | 26 | VINPNYGTTDYNQRFKG | 29 | YDYFTGTGAY | 46 |
| 87 | GYSFTDYHIH | 26 | VINPNYGTTDYNQRFKG | 29 | YDYFTGTGAY | 46 |

TABLE 2-continued

Heavy Chain CDR Alignments

| Fab# | CDR1 | SEQ ID No. | CDR2 | Seq ID No. | CDR3 | Seq ID No. |
|---|---|---|---|---|---|---|
| 88 | GYSFTDYHLG | 25 | VINPNYGTTDYNQRFKG | 29 | YDYFTGTGAY | 46 |
| 89 | GYSFTDYHIH | 26 | VINPNYGTTDYNQRFKG | 29 | YDYFTGTGVY | 52 |
| 91 | GYSFTDYHIH | 26 | VINPNYGTTDYNQRFKG | 29 | YDYHTGTGAY | 48 |
| 92 | GYSFTDYHIH | 26 | VINPNYGTTDYNQRFKG | 29 | YDYHTGTGAY | 48 |
| 93 | GYSFTDYHMS | 27 | VINPNYGTTDYNQRFKG | 29 | YDYHTGTGAY | 48 |
| 94 | GYSFTDYHIH | 26 | VINPNYGTTDYNQRFKG | 29 | YDYFTGTGAY | 46 |
| 95 | GYSFTDYHIH | 26 | VINPNYGTTDYNQRFKG | 29 | YDYYTGTGAY | 47 |
| 96 | GYSFTDYHIH | 26 | VINPEYGTTDYNQRFKG | 32 | YDYFTGTGAY | 46 |
| 97 | GYSFTDYHIH | 26 | VINPNYGTTDYNQRFKG | 29 | YDYHTGTGAY | 48 |
| 98 | GYSFTDYHIH | 26 | VINPNYGTTDYNQRFKG | 29 | YDYYTGTGAY | 47 |
| 99 | GYSFTDYHIH | 26 | VINPNYGTTDYNQRFKG | 29 | YDYFTGTGAY | 46 |
| 100 | GYSFTDYHIH | 26 | VINPEYGTTDYNQRFKG | 32 | YDYATGTGAY | 33 |
| 101 | GYSFTDYHIH | 26 | VINPNYGTTDYNQRFKG | 29 | YDYFTGTGAY | 46 |
| 102 | GYSFTDYHIH | 26 | VINPNYGTTDYNQRFKG | 29 | YDYFTGTGAY | 46 |
| 103 | GYSFTDYHIH | 26 | VINPEYGTTDYNQRFKG | 32 | YDYFTGTGAY | 46 |
| 104 | GYSFTDYHIH | 26 | VINPEYGTTDYNQRFKG | 32 | YDYFTGTGAY | 46 |
| 105 | GYSFTDYHIH | 26 | VINPEYGTTDYNQRFKG | 32 | YDYYTGTGAY | 47 |
| 106 | GYSFTDYHIH | 26 | VINPNYGTTDYNQRFKG | 29 | YDYYTGTGAY | 47 |
| 107 | GYSFTDYHLG | 25 | VINPEYGTTDYNQRFKG | 32 | YDYHTGTGAY | 48 |
| 108 | GYSFTDYHLG | 25 | VINPNYGTTDYNQRFKG | 29 | YDYYTGTGAY | 47 |
| 109 | GYSFTDYHMS | 27 | VINPEYGTTDYNQRFKG | 32 | YDYFTGTGAY | 46 |
| 110 | GYSFTDYHIH | 26 | VINPNYGTTDYNQRFKG | 29 | YDYFTGTGVY | 52 |
| 111 | GYSFTDYHIH | 26 | VINPNYGTTDYNQRFKG | 29 | YDYFTGTGAY | 46 |
| 112 | GYSFTDYHIH | 26 | VINPNYGTTDYNQRFKG | 29 | YDYHTGTGAY | 48 |
| 113 | GYSFTDYHMS | 27 | VINPNYGTTDYNQRFKG | 29 | YDYYTGTGAY | 47 |
| 114 | GYSFTDYHIH | 26 | VINPNYGTTDYNQRFKG | 29 | YDYYTGTGAY | 47 |
| 115 | GYSFTDYHIH | 26 | VINPNYGTTDYNQRFKG | 29 | YDYYTGTGAY | 47 |
| 116 | GYSFTDYHMS | 27 | VINPNYGTTDYNQRFKG | 29 | YDYYTGTGVY | 47 |
| 117 | GYSFTDYHIS | 28 | VINPEYGTTDYNQRFKG | 32 | YDYYTGTGVY | 53 |
| 118 | GYSFTDYHIH | 26 | VINPMYGTTDYNQRFKG | 30 | YDYYTGTGVY | 53 |
| 119 | GYSFTDYHIH | 26 | VINPNYGTTDYNQRFKG | 29 | YDYFTGTGVY | 52 |
| 120 | GYSFTDYHIS | 28 | VINPMYGTTDYNQRFKG | 30 | YDYFTGTGAY | 46 |
| 121 | GYSFTDYHIS | 28 | VINPEYGTTDYNQRFKG | 32 | YDYFTGTGAY | 46 |
| 122 | GYSFTDYHIH | 26 | VINPMYGTTDYNQRFKG | 30 | YDYYTGTGVY | 53 |

TABLE 2-continued

Heavy Chain CDR Alignments

| Fab# | CDR1 | SEQ ID No. | CDR2 | Seq ID No. | CDR3 | Seq ID No. |
|---|---|---|---|---|---|---|
| 123 | GYSFTDYHIH | 26 | VINPNYGTTDYNQRFKG | 29 | YDYYTGTGVY | 53 |
| 124 | GYSFTDYNMN | 11 | VINPMYGTTDYNQRFKG | 30 | YDYYTGTGVY | 53 |
| 125 | GYSFTDYHIH | 26 | VINPEYGTTDYNQRFKG | 32 | YDYFTGTGVY | 52 |
| 126 | GYSFTDYHIH | 26 | VINPMYGTTDYNQRFKG | 30 | YDYFTGTGVY | 52 |
| 127 | GYSFTDYHIH | 26 | VINPNYGTTDYNQRFKG | 29 | YDYYTGTGAY | 47 |
| 128 | GYSFTDYHMS | 27 | VINPMYGTTDYNQRFKG | 30 | YDYYTGTGAY | 47 |
| 129 | GYSFTDYHIH | 26 | VINPMYGTTDYNQRFKG | 30 | YDYFTGTGVY | 52 |
| 130 | GYSFTDYHMS | 27 | VINPMYGTTDYNQRFKG | 30 | YDYYTGTGAY | 47 |
| 131 | GYSFTDYHIH | 26 | VINPEYGTTDYNQRFKG | 32 | YDYFTGTGVY | 52 |
| 132 | GYSFTDYHMS | 27 | VINPMYGTTDYNQRFKG | 30 | YDYFTGTGVY | 52 |

Consensus:
SEQ ID NO: 244
$X_1YX_3FX_5X_6X_7X_8X_9X_{10}$
$X_1$ is H or G
$X_3$ is S, H or P
$X_5$ is G, R, T, N or P
$X_6$ is D or W
$X_7$ is Y or F
$X_8$ is N or H
$X_9$ is M, T, L or I
$X_{10}$ is N, G, H or S
SEQ ID NO: 245
VINP$X_5$YGTTDYNQRFKG
$X_5$ is N, A, M or E
SEQ ID NO: 246
YD$X_3X_4X_5X_6$TG$X_9$Y
$X_3$ is Y, A or P
$X_4$ is Y, F, H, S, W, L or A
$X_5$ is T or P
$X_6$ is G or S
$X_9$ is A, G, L, V or T

TABLE 3

Light Chain CDR Alignments

| Fab# | CDR1 | SEQ ID NO: | CDR2 | SEQ ID NO: | CDR3 | SEQ ID NO: |
|---|---|---|---|---|---|---|
| 1 | RSSQSLVHSRGNTYLH | 122 | KVSNRFS | 150 | SQSTHLPFT | 168 |
| 2 | RSSQSLVHSRGNTYLH | 122 | KVSNRFS | 150 | SQSTHYPFT | 169 |
| 3 | RSSQSLVHSHGNTYLH | 123 | KVSNRFS | 150 | SQSTHLPFT | 168 |
| 4 | RSSQSLVHSNGNTYLH | 124 | KVSNRFS | 150 | SQSTHLPFT | 168 |
| 5 | RSSQSLVHSRGNTYLH | 122 | KVSNRFS | 150 | SQSTHYPFT | 169 |
| 6 | RSSQSLVHSNGNTYLH | 124 | KVSNRFS | 150 | SQSTHYPFT | 169 |
| 7 | RSSQSLVHSYGNTYLH | 125 | KVSNRFS | 150 | SQSTHIPFT | 170 |
| 8 | RSSQSLVHSNGNTYLH | 124 | KVSNRFS | 150 | SQSLHVPFT | 171 |
| 9 | RSSQSLVHSNGNTYLH | 124 | KVSNRFS | 150 | SQSTHIPFT | 170 |
| 10 | RSSQSLVHSRGNTYLH | 122 | KVSNRFS | 150 | SQSTHLPFT | 168 |
| 11 | RSSQSLVHSNGNTYLH | 124 | KVSNRFS | 150 | SQSTHLPFT | 168 |
| 12 | RSSQSLVHSNGNTYLH | 124 | KVSNRFS | 150 | SQSTHEPFT | 172 |
| 13 | RSSQSLVHSHGNTYLH | 123 | KVSNRFS | 150 | SQSTHYPFT | 169 |
| 14 | RSSQSLVHSHGNTYLH | 123 | KVSNRFS | 150 | NQSTHVPFT | 173 |
| 15 | RSSQSLVHSNGNTYLH | 124 | KVSNRFS | 150 | SQTTHVPFT | 174 |
| 16 | RSSQSLVHSNGNTYLH | 124 | KVSNRFS | 150 | SQSTHLPFT | 168 |
| 17 | RSSQSLVHSHGNTYLH | 123 | KVSNRFS | 150 | SQSTHYPFT | 169 |
| 18 | RSSQSLVHSNGNTYLH | 124 | KVSNRFS | 150 | SQSTHLPFT | 168 |
| 19 | RSSQSLVHSNGNTYLH | 124 | KVSNRFS | 150 | SQSMHVPFT | 175 |
| 20 | RSSQSLVHSRGNTYLH | 122 | KVSNRFS | 150 | SQSTHLPFT | 168 |
| 21 | RSSQSLVHSRGNTYLH | 122 | KVSNRFS | 150 | SQSTHLPFT | 168 |

TABLE 3-continued

Light Chain CDR Alignments

| Fab# | CDR1 | SEQ ID NO: | CDR2 | SEQ ID NO: | CDR3 | SEQ ID NO: |
|---|---|---|---|---|---|---|
| 22 | RSSQSLVHSRGNTYLH | 122 | KVSNRFS | 150 | SQSTHLPFT | 168 |
| 23 | RSSQSLVHSRGNTYLH | 122 | KVSNRFS | 150 | SQSTHLPFT | 168 |
| 24 | RSSQSLVHSRGNTYLH | 122 | KVSNRFS | 150 | SQSTHLPFT | 168 |
| 25 | RSSQSLVHSRGNTYLH | 122 | KVSNRFS | 150 | SQSTHLPFT | 168 |
| 26 | RSSQSLVHSRGNTYLH | 122 | KVSNRFS | 150 | SQSTHLPFT | 168 |
| 27 | RSSQSLVHSRGNTYLH | 122 | KVSNRFS | 150 | SQSTHLPFT | 168 |
| 28 | RSSQSLVHSRGNTYLH | 122 | KVSNRFS | 150 | SQSTHLPFT | 168 |
| 29 | RSSQSLVHSRGNTYLH | 122 | KVSNRFS | 150 | SQSTHLPFT | 168 |
| 30 | RSSQSLVHSRGNTYLH | 122 | KVSNRFS | 150 | SQSTHLPFT | 168 |
| 31 | RSSQSLVHSRGNTYLH | 122 | KVSNRFS | 150 | SQSTHLPFT | 168 |
| 32 | RSSQSLVHSRGNTYLH | 122 | KVSNRFS | 150 | SQSTHLPFT | 168 |
| 33 | RSSQSLVHSRGNTYLH | 122 | KVSNRFS | 150 | SQSTHLPFT | 168 |
| 34 | RSSQSLVHSRGNTYLH | 122 | KVSNRFS | 150 | SQSTHLPFT | 168 |
| 35 | RSSQSLVHSRGNTYLH | 122 | KVSNRFS | 150 | SQSTHLPFT | 168 |
| 36 | RSSQSLVHSRGNTYLH | 122 | KVSNRFS | 150 | SQSTHLPFT | 168 |
| 37 | RSSQSLVHSRGNTYLH | 122 | KVSNRFS | 150 | SQSTHLPFT | 168 |
| 38 | RSSQSLVHSRGNTYLH | 122 | KVSNRFS | 150 | SQSTHLPFT | 168 |
| 39 | RSSQSLVHSRGNTYLH | 122 | KVSNRFS | 150 | SQSTHLPFT | 168 |
| 40 | RSSQSLVHSRGNTYLH | 122 | KVSNRFS | 150 | SQSTHLPFT | 168 |
| 41 | RSSQSLVHSRGNTYLH | 122 | KVSNRFS | 150 | SQSTHLPFT | 168 |
| 42 | RSSQSLVHSRGNTYLH | 122 | KVSNRFS | 150 | SQSTHLPFT | 168 |
| 43 | RSSQSLVHSRGNTYLH | 122 | KVSNRFS | 150 | SQSTHLPFT | 168 |
| 44 | RSSQSLVHSRGNTYLH | 122 | KVSNRFS | 150 | SQSTHLPFT | 168 |
| 45 | RSSQSLVHSRGNTYLH | 122 | KVSNRFS | 150 | SQSTHLPFT | 168 |
| 46 | RSSQSLVHSRGNTYLH | 122 | KVSNRFS | 150 | SQSTHLPFT | 168 |
| 47 | RSSKSLVHSRGNTYLH | 125 | KVSNRFS | 150 | SQSTHLPFT | 168 |
| 48 | RSSQSVHSRGNTYLH | 126 | KVSNRFS | 150 | SQSTHLPFT | 168 |
| 49 | VSSQSLVHSRGNTYLH | 127 | KVSNRFS | 150 | SQSTHLPFT | 168 |
| 50 | RSSALVHSRGNTYLH | 128 | KVSNRFS | 150 | SQSTHLPFT | 168 |
| 51 | RSSQSLKHSRGNTYLH | 129 | KVSNRFS | 150 | SQSTHLPFT | 168 |
| 52 | RSSQSLRHSRGNTYLH | 130 | KVSNRFS | 150 | SQSTHLPFT | 168 |
| 53 | RSSRSLVHSRGNTYLH | 131 | KVSNRFS | 150 | SQSTHLPFT | 168 |
| 54 | RSHQSLVHSRGNTYLH | 132 | KVSNRFS | 150 | SQSTHLPFT | 168 |
| 55 | RSSQSLVHSRGNTFLH | 133 | KVSNRFS | 150 | SQSTHLPFT | 168 |
| 56 | RSSQSLVHNRGNTYLH | 134 | KVSNRFS | 150 | SQSTHLPFT | 168 |
| 57 | RSSQSLVHSRGRTYLH | 135 | KVSNRFS | 150 | SQSTHLPFT | 168 |
| 58 | RSSQSLVHRRGNTYLH | 136 | KVSNRFS | 150 | SQSTHLPFT | 168 |
| 59 | RSSQSLVHSRGNTYTH | 137 | KVSNRFS | 150 | SQSTHLPFT | 168 |
| 60 | RSSQSLVHSRGNTYSH | 138 | KVSNRFS | 150 | SQSTHLPFT | 168 |
| 61 | RSSQSLVHSRGNTYHH | 139 | KVSURFS | 150 | SQSTHLPFT | 168 |
| 62 | RSSQSLVHARGNTYLH | 140 | KVSNRFS | 150 | SQSTHLPFT | 168 |
| 63 | RSSQSLVHSRGNTYFH | 133 | KVSNRFS | 150 | SQSTHLPFT | 168 |
| 64 | RSSQSLVHSRGNTWLH | 141 | KVSNRFS | 150 | SQSTHLPFT | 168 |
| 65 | RSSQSLVHSRGNVYLH | 142 | KVSNRFS | 150 | SQSTHLPFT | 168 |
| 66 | RSSQSLVHSRGKTYLH | 143 | KVSNRFS | 150 | SQSTHLPFT | 168 |
| 67 | RSSQSLVHLRGNTYLH | 144 | KVSNRFS | 150 | SQSTHLPFT | 168 |
| 68 | RSSQSLVHSRGNTYLH | 122 | KVSNRFI | 167 | SQSTHLPFT | 168 |
| 69 | RSSQSLVHSRGNTYLH | 122 | KVSNRFS | 150 | SQTTHLPFT | 176 |
| 70 | RSSQSLVHSRGNTYLH | 122 | KVSNRFS | 150 | SQSTSLPFT | 177 |
| 71 | RSSKSLVHSRGNTFLH | 145 | KVSNRFS | 150 | SQSTHLPFT | 168 |
| 72 | RSSKSLVHSRGNTYLH | 125 | KVSNRFS | 150 | SQSTHLPFT | 168 |
| 73 | RSSQSLRHSRGNTFLH | 146 | KVSNRFS | 150 | SQSTHLPFT | 168 |
| 74 | RSSQSLVHSRGNTFLH | 133 | KVSNRFS | 150 | SQSTHLPFT | 168 |
| 75 | RSSQSLVHSRGNTYLH | 122 | KVSNRFS | 150 | SQSTHLPFT | 168 |
| 76 | RSSQSLVHSRGNTFLH | 133 | KVSNRFS | 150 | SQSTHLPFT | 168 |
| 78 | RSSQSLVHSRGNTYLH | 122 | KVSNRFS | 150 | SQSTHLPFT | 168 |
| 79 | RSSQSLKHSRGNTYLH | 129 | KVSNRFS | 150 | SQSTHLPFT | 168 |
| 80 | RSSQSLKHSRGNTYLH | 129 | KVSNRFS | 150 | SQSTHLPFT | 168 |
| 82 | RSSQSLVHSRGNTFLH | 133 | KVSNRFS | 150 | SQSTHLPFT | 168 |
| 84 | RSSQSLVHSRGNTFLH | 133 | KVSNRFS | 150 | SQSTHLPFT | 168 |
| 85 | RSSKSLVHSRGNTYLH | 125 | KVSNRFS | 150 | SQSTHLPFT | 168 |
| 86 | RSSKSLVHSRGNTYLH | 125 | KVSNRFS | 150 | SQSTHLPFT | 168 |
| 87 | RSSQSLKHSRGNTFLH | 147 | KVSNRFS | 150 | SQSTHLPFT | 168 |
| 88 | RSSQSLVHSRGNTFLH | 133 | KVSNRFS | 150 | SQSTHLPFT | 168 |
| 89 | RSSQSLRHSRGNTFLH | 130 | KVSNRFS | 150 | SQSTHLPFT | 168 |
| 91 | RSSQSLKHSRGNTYLH | 129 | KVSNRFS | 150 | SQSTHLPFT | 168 |
| 92 | RSSQSLKHSRGNTFLH | 147 | KVSNRFS | 150 | SQSTHLPFT | 168 |
| 93 | RSSQSLKHSRGNTYLH | 129 | KVSNRFS | 150 | SQSTHLPFT | 168 |
| 94 | RSSQSLVHSRGNTFLH | 133 | KVSNRFS | 150 | SQSTHLPFT | 168 |
| 95 | RSSQSLRHSRGNTYLH | 130 | KVSNRFH | 152 | SQSTHLPFT | 168 |
| 96 | RSSKSLVHSRGNTYLH | 125 | KVANRFS | 153 | SQSTHLPFT | 168 |

TABLE 3-continued

Light Chain CDR Alignments

| Fab# | CDR1 | SEQ ID NO:CDR2 | | SEQ ID NO:CDR3 | | SEQ ID NO: |
|---|---|---|---|---|---|---|
| 97 | RSSKSLVHSRGNTFLH | 145 | KVSVRFS | 154 | SQSTHLPFT | 168 |
| 98 | RSSQSLVHSRGNTFLH | 133 | KVSNRFS | 150 | SQSTHLPFT | 168 |
| 99 | RSSQSLVHSRGNTFLH | 133 | KVSNRFS | 150 | SQSTHLPFT | 168 |
| 100 | RSSKSLVHSRGNTYLH | 125 | KVSNNFS | 155 | SQSTHLPFT | 168 |
| 101 | RSSQSLVHSRGNTFLH | 133 | KVDNRFS | 156 | SQSTHLPFT | 168 |
| 102 | RSSRSLVHSRGNTFLH | 148 | KVTNRFS | 157 | SQSTHLPFT | 168 |
| 103 | RSSQSLRHSRGNTYLH | 130 | KVSNIFS | 158 | SQSTHLPFT | 168 |
| 104 | RSSKSLVHSRGNTFLH | 145 | KVSTRFS | 159 | SQSTHLPFT | 168 |
| 105 | RSSQSLRHSRGNTYLH | 130 | KVSNRFS | 150 | SQSTHYPFT | 169 |
| 106 | RSSQSLVHSRGNTFLH | 133 | KVRNRFS | 160 | SQSTHLPFT | 168 |
| 107 | RSSQSLRHSRGNTYLH | 130 | KVPNRFS | 161 | SQSTHYPFT | 169 |
| 108 | RSSQSLVHSRGNTFLH | 133 | KVSNRFV | 162 | SQSTHYPFT | 169 |
| 109 | RSSQSLRHSRGNTYLH | 130 | KVSNRIS | 163 | SQSTHLPFT | 168 |
| 110 | RSSRSLVHSRGNTYLH | 131 | KVSNRFT | 164 | SQSTHYPFT | 169 |
| 111 | RSSQSLRHSRGNTFLH | 146 | KVSNRNS | 165 | SQSTHLPFT | 168 |
| 112 | RSSKSLVHSRGNTYLH | 125 | KVHNRFS | 166 | SQSTHLPFT | 168 |
| 113 | RSSQSLVHSRGNTFLH | 133 | KVSNRFS | 150 | SQSTHLPFT | 168 |
| 114 | RSSQSLKHSRGNTYLH | 129 | KVSTRFS | 159 | SQSTHLPFT | 168 |
| 115 | RSSQSLVHSRGNTFLH | 133 | KVSNRFI | 167 | SQSTHLPFT | 168 |
| 116 | RSSQSLKHSGNTYLH | 149 | KVSNRFI | 167 | SQSTHLPFT | 168 |
| 117 | RSSKSLVHSRGNTYLH | 125 | KVSNRFI | 167 | SQSTHLPFT | 168 |
| 118 | RSSQSLVHSRGNTFLH | 133 | KVSNRFI | 167 | SQSTHLPFT | 168 |
| 119 | RSSQSLVHSRGNTFLH | 122 | KVSNRFI | 167 | SQSTHLPFT | 168 |
| 120 | RSSQSLVHSRGNTFLH | 122 | KVSNRFI | 167 | SQSTHYPFT | 169 |
| 121 | RSSQSLKHSRGNTFLH | 147 | KVSNRFI | 167 | SQSTHYPFT | 169 |
| 122 | RSSQSLVHSRGNTFLH | 122 | KVSNRFI | 167 | SQSTHLPFT | 168 |
| 123 | RSSKSLVHSRGNTYLH | 125 | KVSNRFI | 167 | SQSTHLPFT | 168 |
| 124 | RSSRSLVHSRGNTYLH | 131 | KVSNRFI | 167 | SQSTHLPFT | 168 |
| 125 | RSSQSLVHSRGNTFLH | 122 | KVSNRFS | 150 | SQSTHLPFT | 168 |
| 126 | RSSRSLVHSRGNTYLH | 131 | KVSNRFI | 167 | SQSTHLPFT | 168 |
| 127 | RSSRSLVHSRGNTYLH | 131 | KVSNRFI | 167 | SQSTHLPFT | 168 |
| 128 | RSSQSLKHSRGNTYLH | 129 | KVSNRFI | 167 | SQSTHYPFT | 169 |
| 129 | RSSKSLVHSRGNTYLH | 125 | KVSNRFI | 167 | SQSTHLPFT | 168 |
| 130 | RSSQSLKHSRGNTYLH | 129 | KVSNRFI | 167 | SQSTHLPFT | 168 |
| 131 | RSSKSLVHSRGNTYLH | 125 | KVSNRFI | 167 | SQSTHLPFT | 168 |
| 132 | RSSKSLVHSRGNTYLH | 125 | KVSNRFI | 167 | SQSTHLPFT | 168 |

Consensus:
SEQ ID NO: 247
$X_1SX_3X_4SX_6X_7HX_9X_{10}GX_{12}X_{13}X_{14}X_{15}H$
$X_1$ is R or V
$X_3$ is S or H
$X_4$ is Q, K, R or A
$X_6$ is V or L
$X_7$ is R, V or K
$X_9$ is S, N, R, A or L
$X_{10}$ is H, R, N or Y
$X_{12}$ is N, K or R
$X_{13}$ is T or V
$X_{14}$ is F, Y or W
$X_{15}$ is L, T, S, H or F
SEQ ID NO: 248
$X_1VX_3X_4RX_6X_7$
$X_3$ is K or I
$X_3$ is S, A, D, T, R, H or P
$X_4$ is N, R or T
$X_5$ is R, I or N
$X_6$ is F, I, or N or
$X_7$ is S, H, I, T or V
SEQ ID NO: 249
$X_1QX_3X_4X_5X_6PFT$
$X_1$ is S or N
$X_3$ is S or T
$X_4$ is T, L or M
$X_5$ is H or S
$X_6$ is L, I, V, E or Y

EXAMPLES

Example 1

ELISA I: Antibody Binding to IL-17 of Various Species

An exemplary ELISA assay for measuring binding of antibodies to IL-17 uses sealed Costar 3366 microtiter plates that are coated overnight at 4° C. with 50 μl of 1.0 μg/ml human IL-17 per well (R&D Systems, #317-IL/CF) in carbonate coating buffer (50 mM sodium carbonate, pH 9.0). Alternatively, mouse, rat, rabbit or cynomolgus monkey IL-17 are used. Human IL-22 (R&D Systems) is used as a control antigen. Rabbit and cynomolgus monkey IL-17 are not commercially available and therefore require cloning and expression, or artificial synthesis, according to methods known in the art making use of the amino acid sequences for IL-17 of the various species provided in FIG. 2 (Seq ID NOs: 9 and 10). Exemplary nucleotide sequences encoding IL-17 of the various species are shown in SEQ ID NOs: 250-254.

The plate is subsequently blocked by adding 100 μl blocking buffer (Pierce #37515). The plate is incubated for 1 hour at 37° C. then washed three times in wash buffer (PBS pH 7.4 and 0.05% Tween). Then, 50 μl of either sample antibody or control antibody (diluted to various concentrations in PBS pH 7.4, e.g., 2, 0.4, 0.08, 0.016, 0.0032 and 0 μg/ml) is added to each well and the plate is further incubated for 1 hour at 37° C. The plate is then washed three times with wash buffer before adding 50 μl per well of anti-human kappa-alkaline phosphatase conjugated diluted to 1:1000 in PBS pH 7.4. The test samples are incubated for 1 hour at 37° C. Then p-nitrophenyl phosphate disodium salt (PNPP, Pierce #37620) is freshly made by dissolving in diethanolamine substrate buffer according to manufacturer's instruction and 50 µl is added to each well. Color development is allowed to proceed for about 10 minutes at room temperature then color signal is measured at an absorbance of 405 nm using any appropriate ELISA plate reader. The degree of binding is proportional to color signal production.

Antibodies of the invention bind human IL-17 in an ELISA assay as described herein, but do not bind rat or mouse IL-17. It is anticipated, given the Biacore data of Example 4 demonstrating that antibodies of the invention bind human and monkey IL-17, that the antibodies of the invention would also demonstrate binding to monkey IL-17 in an ELISA assay as described herein.

Example 2

ELISA II: Antibody Binding to Proteins of IL-17 Family

An ELISA is used to measure whether antibodies of the invention selectively and/or preferentially bind particular human IL-17 members (e.g., IL-17A, IL-17B, IL-17C, IL-17D, IL-17E or IL-17F) or human IL-22 (negative control).

In an exemplary assay, ELISA plate wells (Nunc Immuno Maxisorp) are coated with 100 µl (0.5 µg/ml in 1× coating buffer (BioFx)) of IL-17 family member proteins (R&D Systems) sealed and incubated overnight at 4° C. The solution in the well is removed by flicking and blocking buffer (200 µl 1.5% BSA in PBS) is added. The plates are incubated on a rotating shaker for 30 minutes at room temperature. Then 100 µl of an antibody to be tested is added per well at varying concentrations (e.g., 2, 0.4, 0.08, 0.016, 0.0032 and 0 µg/ml). The plates are again incubated overnight (4° C.) followed by warming on a rotating shaker (60 min room temp). Each plate-well is then washed five times with buffer (1× Ish buffer, BioFX). After washing, an appropriate commercially available HRP-conjugated secondary antibody (1:2000 in PBS with 1.5% BSA) is added (100 µl/well). Plates are re-incubated on a rotating shaker (60 min. room temp.) followed by buffer washing (5×) as described above. The calorimetric signal is developed by adding TMB (100 µl/well) until saturation (approx 3-5 min.) then further development is ended by adding stop solution (100 µl/well, BioFX). The color signal is measured at 450 nm absorbance using any appropriate ELISA plate reader. The degree of binding is proportional to color signal production. Antibodies of the invention (e.g., Fabs 103, 104, 118, 121, 126 and 131 as described in Table 1) specifically bind human IL-17 (i.e., IL-17A), but, under similar conditions, do not bind at greater than background levels to human IL-17B, human IL-17C, human IL-17D, human IL-17E, human IL-17F, murine IL-17 or human IL-22.

Example 3

Isolation and Activation of Cells for Cloning IL-17

A. Rat Splenocytes

Using sterile forceps and scissors, remove spleen of a rat sacrificed by $CO_2$ inhalation and put the spleen into a tube containing 5 ml RPMI 1640 media+10% fetal bovine serum and penicillin/streptomycin (media solution). Pour contents of the tube into a 10 cm Petri dish and remove fat from spleen. Homogenize the spleen gently using a pair of fully frosted, pre-autoclaved microscopy slides. Wash cells off slides using media solution, pipette a few times and filter cells through cell strainer (Fisher Scientific). Wash cells once with media solution, count cells and resuspend them to a final concentration of $2 \times 10^7$ cells/ml in 80 ml. Add cell solution to a T150 flask, add Concanavalin A to a final concentration of 3 µg/ml and incubate at 37° C. for about 15 hours. Harvest the cells, wash with PBS, freeze the cell pellet on dry ice and proceed immediately to standard RNA isolation procedures.

B. Cynomolgus Monkey and Rabbit Peripheral Blood Mononuclear Cells (PBMC)

Load about 7 ml whole blood from cynomolgus monkey or 10 ml whole blood from New Zealand white rabbit into a BD Vacutainer™ CPT™ System for separation of mononuclear cells from whole blood. Centrifuge the CPT cell preparation tube for 20 min at 1500× gravity in a horizontal swinging bucket rotor. Collect lymphocytes and monocytes at the interface, wash twice with media solution, count and resuspend in media solution at a final concentration of $10^6$ cells/ml. Add Concanavalin A to a final concentration of 3 µg/ml and incubate at 37° C. for about 15 hours. Harvest the cells, wash with PBS, freeze the cell pellet on dry ice and proceed immediately to standard RNA isolation procedures.

Example 4

Measuring Binding Kinetic Constants

A BIACORE® 2000 instrument is used to measure antigen-antibody binding kinetics and affinity. The instrument utilizes the optical properties of surface plasmon resonance to detect alteration in protein concentration of interacting molecules within a dextran biosensor matrix. Except as noted, all reagents and materials are purchased from BIACORE® AB. All measurements are performed at 25° C. Samples are resuspended in HBS-EP buffer to a final concentration of 2 µg/ml (150 mM sodium chloride, 3 mM EDTA, 0.005% (w/v) surfactant P-20, and 10 mM HEPES, pH 7.4). Protein A is immobilized on flow cells 1 to 4 of a CM4 sensor chip at a level of 500 response units using an amine coupling kit.

Binding is evaluated using multiple analytical cycles. Each cycle is performed at a flow rate of 50 µl/minute and consists of the following steps: injection of about 20 µl of an antibody composition at 2 µg/ml aiming at a capture of 100-200 response units, injection of 250 µl of human IL-17, Cynomalgus monkey IL-17, New Zealand white rabbit IL-17, rat IL-17 or mouse IL-17 (starting at 10 nM and using two-fold serial dilutions for each cycle) followed by 20 minutes for dissociation, and regeneration using 30 µl of 10 mM glycine hydrochloride, pH 1.5. Association and dissociation rates for each cycle are evaluated using a "1:1 with mass transfer" binding model in the BIAevaluation software.

Full-length mabs 103, 104, 118, 121, 126 and 131 (see Table 1) having an $IgG_4$ Fc region exhibit high affinity binding to human IL-17 and to monkey IL-17 with a $K_D$ less than 5 pM, a $K_{off}$ slower than $2 \times 10^{-5}$ $s^{-1}$ and a $K_{on}$ of at least $5 \times 10^6$ $M^{-1}$ $s^{-1}$. The $K_D$ and $k_{off}$ are improved (i.e., lower $K_D$, slower $k_{off}$) in these variant mAbs over Fab 2321 mAb (parent Fab of e.g., Fab 103 and 104) comprising a murine variable region [Seq ID Nos: 261 (VH of 2321), 262 (VL of 2321)], a human $IgG_4$ heavy chain constant region (SEQ ID NO: 260) and a kappa light chain constant regions (SEQ ID NO: 272). Antibodies of the invention exhibit binding no greater than background levels to mouse IL-17 or rat IL-17; no binding is detected up to 200 nM mouse IL-17 and no binding is detected up to 1 µM rat IL-17. When the full-length mAbs 103, 104, 121 and 126 are tested, under the same conditions described above, for binding to cynomolgus monkey IL-17 and rabbit IL-17; binding to rabbit IL-17 is weak and biphasic while binding to monkey IL-17 is similar to binding to human. Specific values for certain mabs (values are reported as mean ±standard error of mean) of the invention when tested in this assay are listed in Table 4 below. It is contemplated that Fc regions other than that of IgG$_4$ would not significantly affect $K_D$ and $k_{off}$.

TABLE 4

| | $k_{on}$ (M$^{-1}$ s$^{-1}$) | $k_{off}$ (s$^{-1}$) | $K_D$ (pM) |
|---|---|---|---|
| HUMAN IL-17 | | | |
| mAb 103 | 11 (±2) × 10$^6$ | 1.5 (±0.7) × 10$^{-5}$ | 1.4 (±0.7) |
| mAb 104 | 7.7 (±0.6) × 10$^6$ | 1.1 (±0.5) × 10$^{-5}$ | 1.7 (±0.9) |
| mAb 118 | 5 × 10$^6$ | 2 × 10$^{-5}$ | 3.9 |
| mAb 121 | 10 (±0.9) × 10$^6$ | 1.5 (±0.3) × 10$^{-5}$ | 1.6 (±0.4) |
| mAb 126 | 7.5 (±0.4) × 10$^6$ | 1.3 (±0.2) × 10$^{-5}$ | 1.8 (±0.3) |
| mAb 131 | 5.4 × 10$^6$ | 1.6 × 10$^{-5}$ | 2.9 |
| *Parent 2321 mAb | 2.7 × 10$^6$ | 6 × 10$^{-5}$ | 7 |
| CYNO IL-17 | | | |
| mAb 103 | 8.8 × 10$^6$ | 1.1 × 10$^{-5}$ | 1.3 |
| mAb 104 | 9.4 × 10$^6$ | 0.5 × 10$^{-5}$ | 0.5 |
| mAb 121 | 7.8 (±0.3) × 10$^6$ | 0.7 (±0.2) × 10$^{-5}$ | 1.1 (±0.04) |
| mAb 126 | 7.9 (±0.3) × 10$^6$ | 0.7 (±0.6) × 10$^{-5}$ | 0.8 (±0.8) |
| RABBIT IL-17$^a$ | | | |
| mAb 103 | 1.8 × 10$^5$ | 3.6 × 10$^{-4}$ | 2 |
| | 10.6 × 10$^6$ | 19.2 × 10$^{-2}$ | 18.1 |
| mAb 104 | 1.0 (±0.1) × 10$^5$ | 1.8 (±1.0) × 10$^{-4}$ | 1.9 (±1.3) |
| | 4.0 (±2) × 10$^6$ | 7.0 (±2) × 10$^{-2}$ | 20 (±6) |
| mAb 121 | 8 (±6) × 10$^5$ | 4 (±3) × 10$^{-4}$ | 0.51 (±0.13) |
| | 17 (±11) × 10$^6$ | 2.1 (±0.2) × 10$^{-2}$ | 1.5 (±1.0) |
| mAb 126 | 1.5 (±0.6) × 10$^5$ | 1.7 (±0.5) × 10$^{-4}$ | 1.3 (±0.6) |
| | 9 (±3) × 10$^6$ | 11 (±2) × 10$^{-2}$ | 14 (±4.0) |

$^a$Binding is biphasic and data fit with heterogeneous ligand binding model resulting two affinities.

Example 5

IL-17 Receptor/Anti-IL-17 Antibody Binding Competition Studies

This example demonstrates that the antibodies of the invention compete for binding to IL-17 with the IL-17 receptor.

BIACORE binding studies are performed using the IL-17 receptor Fc-fusion protein (R&D #177-IR). To demonstrate that the IL-17 receptor Fc-fusion protein binds human IL-17, a BIACORE assay is performed in BIACORE binding buffer (HBS-EP)+1 mg/ml BSA at 25° C. on a BIACORE 2000 instrument. A CM4 chip is used with approximately 600 response units of Protein A immobilized on flow cells 1, 2 and 3 of the chip. Approximately 100 response units of IL-17 receptor Fc-fusion protein is captured on flow cell 2 of the chip. Human IL-17 is then exposed to flow cells 1 and 2 in concentrations ranging from 600 nM to 9.4 nM. After each 250 µl injection of human IL-17, the complex is allowed to dissociate for about 12 minutes by running buffer across the chip. At the end of the dissociation, a 20 µl injection of 100 mM glycine pH 1.5 is used to regenerate the chip before the next cycle of binding begins. Flow cell 1 is used as a reference flow cell. The data is fit using the "Bivalent analyte" model in the BIAevaluation Version 3.2 software. The results indicate that this interaction has an on-rate of 1.06×10$^5$ M$^{-1}$ s$^{-1}$, a fast off-rate of 20.3 s$^{-1}$ and a slow off-rate of 1.63×10$^{-4}$ s$^{-1}$. Therefore, this interaction has a $K_D$ or binding affinity of 1.5 nM and 0.19 mM which is much weaker than the binding affinities of the antibodies of the invention to human IL-17.

Binding for the competition experiment is also measured in HBS-EP+1 mg/ml BSA at 25° C. on a BIACORE 2000 instrument with a CM4 chip. Approximately 1000 response units of an antibody of the invention is immobilized on flow cells 2, 3 and 4 of the chip; flow cell 1 is left blank. Using a flow rate of 50 µl/ml, 25 µl of 500 nM human IL-17 is injected over all four flow cells, forming the antibody:antigen complex on the surface of the chip. After the injection is complete and the complex formed, 250 µl of 500 nM human IL-17 receptor Fc fusion protein is injected over all four flow cells. At the end of this injection a 25 µl injection 100 mM glycine pH 1.5 is used to regenerate the chip. The same binding experiment is then repeated using a 250 µl injection of buffer rather than IL-17 receptor Fc fusion protein.

The binding profiles for both the receptor injection over the antibody:antigen complex and for the buffer control injection over the antibody:antigen complex are identical. This indicates that there are no binding sites available for the dimeric IL-17 to bind to its receptor once it is bound to an antibody of the invention. This result also indicates that the receptor is not able to "pull" IL-17 away from any of the antibodies once the complex is formed. These antibodies can inhibit human IL-17 from binding to its receptor, therefore neutralizing biological activity of human IL-17.

Example 6A

In vitro IL-8 Reporter Assay

To test the ability of an antibody of the invention to neutralize or antagonize an IL-17 bioactivity, one can utilize the IL-8 reporter assay described herein. This approach can also be used to determine the potency of Fabs or mAbs of the invention in a cell-based assay. The human HS27 cell line (ATCC #CRL-1634) secretes IL-8 in response to IL-17. The IL-17-induced IL-8 secretion is inhibited by neutralizing anti-IL-17 antibodies (See, e.g., *J. Imm.* 155:5483-5486, 1995 or *Cytokine* 9:794-800, 1997). Accordingly, IL-17-induced IL-8 secretion should proceed unconstrained if sufficient IL-17 is added to HS27 cells in the absence of neutralizing anti-IL-17 antibody.

HS27 cells are maintained in assay medium: DMEM high glucose medium lacking phenol red (Invitrogen #31053-028) with 10% fetal bovine serum, 4 mM L-glutamine, 1 mM sodium pyruvate, penicillin G (100 U/500 ml) and streptomycin (100 µg/500 ml). Cells are grown in T150 flasks until they are about 80-90% confluent the day of the assay. Human IL-17 (R&D Systems, #317-IL-050) is reconstituted in sterile PBS without Ca$^{2+}$ and Mg$^{2+}$ stored frozen, freshly thawed for use and diluted to 200 ng/ml in assay medium. A 50 µl aliquot of the diluted IL-17 is added to each well of a 96-well flat-bottom tissue culture plate (Falcon #35-3072) with the outer wells left empty. Duplicate wells are used for a media-only control (100 µl/well) and IL-17-only control (100 µl/well). Testing is carried out in duplicate or triplicate. Sterile full-length mAb proteins are diluted to a maximum concentration of 24 µg/ml in assay media. Serial dilutions (typically 1:5) are made in a separate assay plate and 50 µl of the Fab samples at the various dilutions are added to the wells containing IL-17 then incubated at 37° C. for 1 hour. Assay medium alone is used as a negative control.

HS27 cells (typically about 20,000 cells in 100 µl assay medium) are added to each well of the plate containing Fab+ IL-17 (or controls) and incubated for about 48 hours at 37° C. The media supernatants are then collected after centrifugation of the 96 well plates for 5 minutes at 500 times gravity and diluted 1:15 or 1:10 in assay media. The level of IL-17 neutralization is measured by determination of IL-8 amounts in supernatant using a commercial ELISA kit according to manufacturer's instruction except assay medium is substituted for standard diluent and substrate volume is 100 μl/well (R&D Systems, ELISA D-8000C or R&D DuoSet ELISA #DY208hIL-8). ELISA measurements (450 nm) are taken on a microplate reader. Calibration curves are obtained using a 4-parameter logistic fit with IL-8 values (pg/ml) determined from the calibration curves using standard statistical techniques. $IC_{50}$ values are obtained using standard statistical techniques.

Full-length mabs 103, 104, 121 and 126 of the invention (with $IgG_4$ Fc region), when tested in the assay described (2-4 replications), have an average $IC_{50}$ (based on an estimated molecular weight of 150 kD for each mAb) of between 450 and 500 pM with the range of all measured values between 365 and 618 pM.

Example 6B

In vitro GROα Reporter Assay

To test the ability of an antibody of the invention to neutralize or antagonize an IL-17 bioactivity, one can utilize the following cell-based assay. IL-17 can stimulate epithelial cells and other cells to secrete GROα. The ability of an antibody of the invention to neutralize IL-17-induced GROα secretion from the human colorectal adenocarcinoma epithelial cell line HT-29 is tested in this assay.

To test whether human IL-17 dose-dependently induced GROα secretion from HT-29 cells, recombinant IL-17 (R&D Systems #317-IL-050/CF; reconstituted in sterile Dulbecco's PBS without $Ca^{2+}$ and $Mg^{2+}$ (D-PBS)) is diluted (to 4.5 μg/ml; 3× the highest test concentration) in assay/culture medium (McCoy's 5A (Invitrogen); 10% FBS (Invitrogen); penicillin G (100 U/500 ml); and streptomycin (100 μg/500 ml. IL-17 is further diluted serially (1:5) in assay medium. Various concentrations of IL-17 (0.096 ng/ml-1,500 ng/ml; 3.0 pM-46,875 pM) are dispensed (50 μl each) into inner wells of a tissue-culture treated 96-well plate. Assay medium (50 μl) is dispensed into 3 wells for a "medium alone" treatment. Testing is carried out in triplicate (3 wells per treatment). The plate containing IL-17 in assay medium is incubated for approx. 60-90 minutes at 37° C., 5% $CO_2$, before the addition of HT-29 cells.

For evaluation of an antibody of the invention, e.g., mAb 126 with an $IgG_4$ Fc region, a concentration of IL-17 that gave approximately 70% of maximal GROα secretion from HT-29 cells is used (60 ng/ml). Recombinant human IL-17 (R&D Systems) is diluted (to 240 ng/ml; 4× working concentration) in assay/culture medium. Diluted IL-17 is dispensed (50 μl) into 60 separate inner wells of tissue-culture treated 96-well plates (Becton Dickinson Falcon #35-3072). Assay medium (50 μl) is dispensed into 3 wells for a "medium alone" treatment.

A dose range of an antibody of the invention to be tested is typically from 2.56-40,000 pM. In a separate dilution plate, the antibody of the invention and control antibody (sterile, in 1×PBS, pH 7.4) are diluted to 160,000 pM in assay medium. The antibody of the invention and control antibody are further diluted serially (1:5) in assay medium. Each test concentration of the antibody of the invention to be tested is then added (50 μl) to wells containing IL-17. Testing is typically carried out in triplicate. Assay medium alone (50 μl) is used for "medium alone" and "IL-17 alone" controls. Plates containing IL-17 and antibody of the invention mixtures are incubated for 60-90 minutes at 37° C., 5% $CO_2$, before the addition of HT-29 cells.

HT-29 cells (human colorectal adenocarcinoma epithelial cells, ATCC #HTB-38), are maintained in culture/assay medium in tissue culture-treated flasks using standard techniques. HT-29 cells are grown in tissue culture flasks until they were 50-80% confluent on the day of the assay. On the day of the assay, the cells are rinsed with HBSS (Cambrex #CC-5024) and detached from the culture flasks with trypsin+EDTA. The trypsin is inactivated with complete assay medium. HT-29 cells are then centrifuged at 500×g for 5 min. at RT. The cell pellet is then re-suspended in assay medium and 20,000 HT-29 cells (in 100 μl) are added to each treatment well of the 96-well plates. An equal volume of D-PBS is added to each of the unused edge wells (without cells) to reduce edge effects resulting from evaporation. The 96-well plates were placed in a tissue culture incubator (37° C., 5% $CO_2$) for approximately 48 hours.

At the end of the assay, the plates are centrifuged (500×g for 5 min. at RT), and the cell culture media is transferred to polypropylene 96-well plates. GROα levels are measured with a GROα sandwich ELISA (R+D Systems DuoSet #DY275), as per the manufacturer's instructions, except for: using assay medium as the standard diluent, using 1× ELISA wash buffer from BioFX Labs, using a sample and standard volume of 50 μl per well, using a substrate from BioFX Labs (HRP substrate, #TMBW-1000-01), and using a stop solution from BioFX Labs (#LSTP-1000-01) (100 μl per well). At the end of the ELISA reactions, plates are read at 450 nm on a microplate reader. Calibration curves for GROα are obtained by performing a 4-parameter logistic fit. GROα values (concentration in pg/ml) for the samples are obtained from the calibration curves. The human colorectal adenocarcinoma epithelial cell line HT-29 secreted GROα when stimulated with IL-17, in a dose-dependent manner (Table 5). Control human IgG4 did not cause a decrease in IL-17-induced GROα secretion. These results (Table 6) demonstrate that mAb 126 is able to completely neutralize human IL-17-induced GROα secretion from HT-29 cells in vitro using the conditions described. The $IC_{50}$ value for mAb 126 in this assay is approximately 560 pM.

TABLE 5

| Human IL-17 (ng/ml) | AVG GROα (pg/ml) | STDEV |
|---|---|---|
| 1,500.00 | 2,420.4 | 311.8 |
| 300.00 | 2,047.5 | 509.9 |
| 60.00 | 1,556.0 | 209.0 |
| 12.00 | 960.0 | 24.9 |
| 2.40 | 502.5 | 12.3 |
| 0.48 | 297.9 | 6.3 |
| 0.10 | 205.8 | 4.8 |
| 0 | 149.2 | 16.7 |

Abbreviations:
AVG = average;
STDEV = Standard deviation.

TABLE 6

| | mAb 126 | | $IgG_4$ negative control | |
|---|---|---|---|---|
| Antibody conc., pM | AVG GROα, pg/ml | STDEV | AVG GROα, pg/ml | STDEV |
| 40,000.0 | 123.8 | 1.4 | 1,297.3 | 29.4 |
| 8,000.0 | 134.1 | 6.4 | 1,419.9 | 133.4 |
| 1,600.0 | 151.3 | 9.5 | 1,370.4 | 114.7 |

TABLE 6-continued

| Antibody conc., pM | mAb 126 | | IgG$_4$ negative control | |
|---|---|---|---|---|
| | AVG GROα, pg/ml | STDEV | AVG GROα, pg/ml | STDEV |
| 320.0 | 1,170.6 | 56.0 | 1,388.6 | 54.1 |
| 64.0 | 1,340.8 | 59.1 | 1,380.4 | 36.0 |
| 12.8 | 1,362.0 | 21.1 | 1,346.2 | 81.6 |
| 2.56 | 1,280.9 | 56.1 | 1,243.4 | 118.3 |
| 0 (IL-17 alone) | 1,201.4 | 66.1 | | |
| Medium alone | 117.2 | 10.0 | | |

Abbreviations:
conc. = concentration;
AVG = average;
STDEV = Standard deviation.

Example 7

In vivo Neutralization of hIL-17

Human IL-17 is able to bind and stimulate the mouse IL-17 receptor, leading to an elevation and subsequent secretion of mouse KC(CXCL1) chemokine. Time and dose ranging experiments are undertaken to identify the optimal dose of human IL-17 and the optimal time for induction of mouse KC. These experiments indicate that a 150 µg/kg dose of human IL-17 and a time of 2 hours post IL-17 administration gives maximal levels of KC in mouse serum. Full-length antibodies of the present invention (e.g., Fab 126 or Fab 121 with HCVR operably linked to human IgG$_4$ Fc, SEQ ID NO:260 [or SEQ ID NO: 278] and the LCVR operably linked to a human kappa constant region, SEQ ID NO: 263 [or SEQ ID NO: 277]) are administered intravenously to mice at 1, 10, 100 and 1000 µg/kg, one hour prior to a subcutaneous injection of human IL-17. At two hours after human IL-17 administration, the mice are sacrificed and KC levels are determined by ELISA using a commercially available kit according to manufacturer's instruction (KC Quantikine, R&D). Isotype matched antibodies are used as negative controls. The antibodies block the ability of human IL-17 to stimulate the mouse IL-17 receptor, leading to inhibition of an elevation of mouse KC, in a dose dependent manner. Mab126 (a full length antibody comprising Fab 126), at a dose of 20 µg/mouse under the conditions described, decreases the mean KC level by approximately four-fold compared to a control antibody which had no effect. Mab 121, at a dose of 20 µg/mouse under the conditions described, decreases the mean KC level by approximately three-fold compared to a control antibody.

Example 8

Epitope Mapping

Two of the anti-IL-17 antibodies (Fab 126 and Fab 104) are used to determine that the humanization and optimization of the parent murine Fab (2321, SEQ ID NOs: 261 and 262) do not alter the epitope-binding ability of the Fabs resulting from humanization and optimization of the parent. The humanized, optimized Fabs bind to the same epitope as does the parent murine Fab as determined by a standard competition ELISA or by H-D exchange and mass spec analysis for epitope mapping (See, e.g., Hoofnagle, A., et al., *Methods Mol. Biol.* 250:283-298, 2004; Hoofnagle, A., et al., *Ann. Rev. Biophys.* *Biomol. Struct.*, 32:1-25, 2003; Baerga-Ortiz, A., et al., *Protein Sci.* 11: 1300-8, 2002) therefore, Fabs 1-132 of the invention derived from the same parent Fab, would be expected to bind the same epitope.

Using the H-D exchange and mass spec assay (H/DXMS) to map the epitope, it is determined that amino acids between 80 and 89 [ADGNVDYHMN (SEQ ID NO: 266)] of human IL-17 (SEQ ID NO: 1) are comprised within the discontinuous epitope to which the antibodies of the invention bind. DGNVDYH (SEQ ID NO: 267) is an essential sequence comprised within the discontinuous epitope to which antibodies of the invention bind based on comparison of sequence variation of IL-17 among different species and binding capability. Changing the amino acid sequence of SEQ ID NO: 267 within the context of entire IL-17 sequence, results in no detectable binding to the altered IL-17 by an antibody of the invention. Antibodies of the invention do not bind to rat or mouse IL-17 at levels greater than control antibody.

H/DXMS assay is used to identify regions of IL-17 to which antibodies of the invention bind. The rate of amide hydrogen exchange rate is dependent on the structure and solvent accessibility of the amid hydrogen. Free IL-17 or IL-17: antibody complex in water is mixed with deuterated water (D$_2$O) to allow exchange of amide protons by deuterium. Those backbone amide groups that participate in protein binding are protected from exchange and remain protonated. These regions are then identified by peptic proteolysis, coupled with LC and electrospray ionization mass spectrometry. Human IL-17 containing a C-terminal His and Flag tag (IL-17-Flis) is expressed and purified from GS-CHO cells using an IMAC column. Two 10 µg aliquots (7.7 µl) of IL-17-Flis solution is transferred into 2 Microcon, and 100 µg of either mAb 104 or mAb 126 (molar ratio of IL-17/Mab=1/2) is added into Microcon. Twenty µg of IL-17-Flis solution is transferred into another Microcon and no antibody added. Then 1×PBS buffer is added into each Microcon to the final volume of ~180 µl and centrifuged at 14,000 g for 14 min. Then 150 ml of 1×PBS buffer is added into each Microcon and centrifuged at 14,000 g for 14 min. These steps are necessary to ensure the free antigen and the antigen:antibody complex are in identical buffer conditions.

The protein portion is collected and the final volume is adjusted to 50 µl (complex) or 80 µl (IL-17-Flis only) with 1×PBS. Six microliters of IL-17-Flis or complex of IL-17-Flis and mAb complex are transferred into a micro plastic vial, and 14 µl of 100% D$_2$O is added into it, resulting in 70% D$_2$O in the sample. The solution is incubated at ambient temperature for 10 min. The exchange is immediately quenched, digested by adding 20 µl of 1% formic acid solution and 2 µl of 2 mg/ml pepsin solution, and incubated at ambient temperature for 30 sec or at 0° C. for 10 min. The digest is immediately injected onto a column manually. Waters 2795 HPLC and Micromass LTC Premier are used for all assays. HPLC stream from HPLC pump is connected to a metal tube (about 1 ml), to manual injector, to a Zorbax C18 column (2.1×50 mm) running under these settings (Column Temperature: 0° C.; Mobile Phase C, 0.15% formic acid in H2O, D: 0.12% Formic acid in ACN; Run Time: 23 min). The column is equilibrated with 98% A (0.15% formic acid aqueous solution) and 2% B (0.12% formic acid in acetonitrile) at a flow rate of 0.2 ml/min. A gradient elution is performed from 2% to 10% B over 0.5 min, then to 40% B over 14.5 min, then to 90% B over 1 min with 2 min hold, and then returned to 2% B in 1 min.). The sample from HPLC is analyzed by mass spectrometer operated with these settings (Ion Mode: Positive; Mass Scan Range: 300-2000; Sample Cone Voltage: 80; Desolvation Gas Flow (L/Hr): 700; Desolvation Temp:

300° C.). The metal tube, injector loop and column are submerged in ice water throughout the assay. Mass spectrum of each peptic peptide of IL-17 is obtained after H/D exchange with or without an anti-IL-17 mAb tested. For small peptides, the average mass of each peptide is calculated based on its isotopic ions and intensities. For larger peptides, the average masses are obtained from deconvoluted mass spectra after internal calibration.

When antibody forms a complex with IL-17, the binding region (epitope) of IL-17 is protected from solvent. This leads to slower amide hydrogen exchange rates when compared to those of IL-17 alone. By comparing the mass of peptides from the free and from the complex after deuterium exchange, the peptides protected by complex formation should be different from the corresponding peptide in free IL-17. Table 7 below lists mass differences that are obtained by H/DXMS for peptic peptides of IL-17. These peptic peptides cover the whole sequence of IL-17-Flis. As the data in the table demonstrate, the mass difference of IL-17-Flis peptide between the complex and itself is similar for both antibodies tested, i.e. they bind the same epitope. A major mass difference is found for the peptic peptide 24-87+117-133 (i.e., amino acids 24 to 87 and 117 to 133 of IL-17) (these two peptides are connected through disulfide bond) and 66-87+117-134, suggesting residues within these regions are involved in binding. Since those peptic peptides are quite large, other enzymatic digests are necessary to narrow down specific amino acid residues involved in binding. In addition to this data, the antibodies of the invention do not bind to other member of IL-17 family (IL-17 B, C, D, E, and F) and they also do not bind to mouse or rat IL-17. These data together with sequence comparison and examination of IL-17 homology structural model suggest that residues 80-89 are comprised within a non-linear epitope of IL-17 to which the antibodies of the invention bind.

TABLE 7

| Peptic Peptide | IL-17-Flis + mAb 104 | | IL-17-Flis + mAb 126 | |
|---|---|---|---|---|
| | Ave (n = 3) | SD | Ave (n = 3) | SD |
| 1-23 + 98-116 | −0.36 | 0.61 | −0.78 | 0.59 |
| 24-43 | −0.79 | 0.13 | −0.44 | 0.65 |
| 27-42 | −0.56 | 0.17 | −0.56 | 0.38 |
| 24-65 | −1.32 | 0.54 | −1.17 | 0.19 |
| 54 to 65 | −0.17 | 0.37 | −0.53 | 0.25 |
| 24-87 + 117-133 | −3.60 | 0.38 | −4.09 | 0.29 |
| 66-87 + 117-134* | −1.94 | | −2.38 | |
| 88-97 | −0.30 | 0.08 | −0.29 | 0.14 |
| 111-116 | −0.08 | 0.07 | −0.17 | 0.08 |
| 135-151 | −0.14 | 0.03 | −0.12 | 0.12 |

Note:
delta Mass is obtained by subtracting a peptic peptide average mass of IL-17-Flis only from the corresponding peptide average mass of IL-17-Flis and antibody complex.
*This data is from a 10 min digestion at 0° C. (n = 1). All others are from ambient digestion for 0.5 min.

Example 9

IL-17 Expression in Cancer Tissues

Various human non-cancerous and cancerous cell lysates are tested for the presence of IL-17 protein. Tissues (approximately 50-100 mg piece) are snap-frozen on dry ice, thawed on ice and lysed in 350 µl TPER buffer (Pierce #78510) including protease inhibitors (Pierce #78410) and phosphatase inhibitors in tubes containing ceramic lysing beads (Qbiogene #6913-050; 1.4 mm ceramic beads in 2.0 ml tubes). The tubes are placed on ice for 5-10 min then centrifuged at 13,000× gravity for 10 min at 4° C. and the material transferred to new tubes to remove debris. Recentrifuge as described and transfer to new tube. Protein concentration is determined using a standard BSA method. The samples are analyzed for IL-17 using a commercial IL-17 ELISA kit according to manufacturer's instructions (R&D #DY317 using wash buffer, substrate solution and stop solution from BioFX Labs). IL-17 levels are normalized to total protein concentration. IL-17 levels are increased between two- and three-fold in cancerous colon tissue (60 samples tested) as compared to normal colon tissue (63 samples tested). IL-17 levels are increased on average three- to four-fold in cancerous kidney tissue (21 samples tested) as compared to normal kidney tissue (21 samples tested). IL-17 levels in cancerous prostate tissue (44 samples tested) are increased as compared to the normal prostate tissue (7 samples tested). The IL-17 levels were not elevated in other types of tumor tissue tested including breast, neck, lung, larynx, thyroid, tongue, ovary and brain.

Example 10

IL-17 Activation of Microglial Cells

IL-17 induces a murine brain microglia cell line (BV-2) to secrete IFN and IL-12p70. The BV-2 murine microglial cell line [obtained from Scios, with permission from Elisabeta Blasi (Microbiology University of Perugia, Italy) who originally isolated them (E. Blasi et al., *J. Immunology* 1990, 27:229-237)] are cultured on poly-D-lysine coated tissue culture flasks, to no greater than 60% confluence in high-glucose DMEM (Invitrogen #31053-028) with 2 mM L-glutamine (Invitrogen/GIBCO #25030-081), 10% FBS (heat inactivated; Invitrogen/GIBCO #10082-147), 1 mM sodium pyruvate (Invitrogen/GIBCO #11360-070), 100 µg/ml Normocin (InvivoGen) at 37° C., 5% $CO_2$.

On day 0 of the assay, BV-2 cells are rinsed (Dulbecco's PBS without Ca2+ and Mg2+; Invitrogen), detached (0.25% trypsin+EDTA) followed by trypsin inactivation then centrifuged (500×g 5 min. at RT). The resulting cell pellet is resuspended to a cell density of ~7,000 cells/100 µl culture medium. 100 µl of cell suspension is dispensed into 60 separate inner wells of poly-D-lysine coated tissue-culture treated 96-well plates. Plates are incubated as described, for approx. 48 hrs before treatment with IL-17.

On day 2 of the assay, recombinant mouse IL-17 (mIL-17) (carrier-free; R&D Systems); reconstituted in sterile Dulbecco's PBS without Ca2+ and Mg+ is diluted in a polypropylene plate to 1.5 µg/ml (the highest test concentration) in culture medium. Mouse IL-17 is further serially diluted in the polypropylene plate. A positive control is LPS diluted in culture medium to 1 µg/ml (the highest test concentration). Assay medium is used as a negative control. Medium is gently aspirated from the cells, before adding treatments (150 µl/well). Testing is carried out in triplicate (3 wells per treatment). Separate replicate plates are incubated for either 24 hr. or 48 hr. at 37° C., 5% $CO_2$.

On days 3 and day 4 of the assay, plates are centrifuged (500×g for 5 min. RT), then cell culture media is transferred to polypropylene 96-well plates, which are sealed and frozen (−80° C.). Media samples are thawed and assayed for cytokine and chemokine levels with a murine 22-plex multiplex kit (Linco), as per the manufacturer's instructions (except: a black-walled polycarbonate filter plate (Millipore) replaces the filter plate included in the kit). Fluorescence is read on a Luminex® instrument (50 beads per bead set, low RP1 gain setting). Data is shown in Table 8 below.

Standard curves are obtained using a four- or five-parameter logistic fit. IFNγ and IL-12p70 values (pg/ml) are determined from the standard curves using standard statistical techniques.

TABLE 8

| conc. of mIL-17, µg/ml | AVG. IFNγ, pg/ml | AVG. IL-12p70, pg/ml |
|---|---|---|
| 24 hours after treatment with IL-17 | | |
| 1.5 | 125.87 | 65.58 |
| 0.375 | 123.89 | 59.63 |
| 0.0938 | 125.61 | 67.87 |
| 0.0059 | 58.91 | 38.12 |
| 0.0015 | 18.78 | 12.34 |
| medium only control | below detection limit | below detection limit |
| LPS, 1 µg/ml | 5.11 | 51.11 |
| LPS, 0.25 µg/ml | 5.07 | 49.00 |
| 48 hours after treatment with IL-17 | | |
| 1.5 | 134.38 | 61.48 |
| 0.375 | 124.99 | 58.65 |
| 0.0938 | 119.96 | 58.15 |
| 0.0059 | 47.07 | 27.87 |
| 0.0015 | 13.97 | 9.44 |
| medium only control | below detection limit | below detection limit |
| LPS, 1 µg/ml | 5.20 | 46.37 |
| LPS, 0.25 µg/ml | 4.30 | 36.36 |

Example 11

DSS Induction Model of Irritable Bowel Disorder

IBD is a chronic inflammatory disease which includes Crohn's Disease and Ulcerative Colitis. IL-17 protein levels are significantly elevated in the sera and in colon tissues from both ulcerative colitis and Crohn's disease patients. However, IL-17 is not detectable in the sera from normal individuals, or patients with infectious colitis or ischaemic colitis The DSS (Dextran Sodium Sulfate) model is one of the oldest and most representative pre-clinical model for irritable bowel disease (IBD). In the DSS model (see, e.g., *FASEB Journal.* 2004; 18:1550-1552) both acute and chronic inflammatory lesions are induced. Mice have a high degree of uniformity of the legions with losing body weight and colon length. It is reproducible in respect of time course and severity among individual mice. For disease induction, mice receive 5% DSS 30-40 Kd) in drinking water for 7 days. Disease Activity Index (DAI) including hemoccult positive or rectal bleeding, loose stool and loss of body weight (5-8%) is observed at about day 8. Body weights of mice are monitored every day for 2 weeks. Mice are sacrificed from about day 12 to about day 15. IL-17 protein is significantly increased in DSS-treated colon versus naïve colon. Treatment with IL-17 antibody may reduce the disease activity index.

Example 12

EAE Model for Multiple Sclerosis

EAE is a CD4+ T cell-mediated demyelinating disease of the central nervous system (CNS) that serves as a model for MS in humans. The pathogenic mechanisms of EAE development include antigen-specific T cell activation and Th1 differentiation followed by T cell and macrophage infiltration into the CNS. IL-17 contributes to the pathology of multiple sclerosis (MS). Microarray analysis of MS lesions of human patients have demonstrated an increase of IL-17 (Lock, et al. Nat. Med. 8:500-508, 2002). IL-17 mRNA-expressing mononuclear cells (MNC) in blood and cerebrospinal fluid are significantly elevated in number in MS patients and higher numbers of IL-17 mRNA-expressing blood MNC were detected during MS clinical exacerbation compared to remission (Matusevicius, et al. Multiple Sclerosis. 5:1-1-104, 1999). EAE is significantly suppressed in IL-17 knockout mice (Nakae et al., *J. Immun.* 171:6173-6177).

The example described here demonstrates that IL-17 protein is increased in the spinal cord of EAE mice and treatment with an anti-murine IL-17 antibody reduces the EAE score in the active EAE model. For disease induction, 8-9 week old female C57BL/6 mice are subcutaneously immunized on day 0 with either (i) 200 µl of 5 mg/ml pertussis toxin (PT) and Complete Freund's Adjuvant (CFA) or (ii) PT, CFA and 300 µg/200 µl of MOG35-55 (myelin oligodendrocyte glycoprotein emulsified in CFA containing 5 mg/ml of heat inactivated *Mycobacterium tuberculosis*). On day 2, mice are treated again with PT. Mice are scored throughout the study for levels of paralysis. Disease is expected in the group receiving MOG. A rat anti-murine IL-17 monoclonal IgG$_1$ antibody or isotype control antibody is administered to mice on days 1, 7 and 15 (BD Biosciences for rat anti-murine IL-17 antibody). Mice receiving MOG are sacrificed when clinical score reaches between 1-3 (on a scale of 0-4); this is between days 14-31 for study 1 in Table 9 below and between days 14-16 for study 2 in Table 10 below. Clinical signs of disease develop about day 10. Individual animals are subjectively scored by at least 2 scorers independently and blinded to the identity of treatment groups according to clinical CNS disease severity. Grade 0 is normal; Grade 1 is completely limp tail; Grade 2 is unilateral partial hind limb weakness; Grade 3 is complete hind limb paralysis; and Grade 4 is moribund. (see *J. Exp. Med.* 194: 873-881, 2001). A control mouse is sacrificed on the same day as a MOG-treated mouse. Spinal cords are isolated at the time of sacrifice and flash frozen to be used for IL-17 protein analysis by ELISA. IL-17 antibody treatment group has significantly lower disease scores as compared to isotype control group.

Lysates of each whole spinal cord are made in 1 ml (study 1 in Table 9 below) or 0.4 ml (study 2 in Table 7 below) TPER protein extraction reagent (Pierce #78510) with complete protease inhibitors (Roche Applied Science #11697498), in 2 ml tubes containing ceramic beads (lysing matrix D, QBiogene #6913050), and FastPrep instrument (Bio101) for 30 seconds at a scale of 5.5. After lysis, samples are centrifuged (5 min. at 14,000 rpm in a microfuge) to remove debris. Supernatants are transferred to new microfuge tubes. Total protein concentration in each lysate is determined with a BCA protein assay kit (Pierce #23225), using the microplate protocol of the manufacturer. Lysates are frozen and stored at −80° C.

After thawing lysates on ice, and clarifying by centrifugation, mouse IL-17 levels are measured in undiluted samples by ELISA (R&D Quantikine #M1700) as per manufacturer's instructions. Standard curves are obtained using a four-parameter logistic fit. IL-17 values are determined from the standard curves using standard statistical techniques. IL-17 levels are normalized to protein concentration in each sample and expressed as pg IL-17/ml total protein in each lysate in Tables 9 and 10 below. As demonstrated by the data in the tables, increased levels of IL-17 were detected in EAE mice.

TABLE 9

| | STUDY 1 | | | |
|---|---|---|---|---|
| GROUP | RANGE OF mIL-17 VALUES, pg/mg | AVG. mIL-17, pg/mg (+/−SE) | RANGE OF CLINICAL SCORES AT SACRIFICE | AVG. CLIN. SCORE AT SACRIFICE (+/−SE) |
| Naïve (n = 7) | 3.63-10.06 | 5.19 +/− 0.87 | N/A | N/A |
| CFA (n = 14) | 3.16-7.51 | 4.31 +/− 0.33 | N/A | N/A |
| CFA + MOG (n = 14) | 4.12-16.62 | 8.57 +/− 1.01 | 0.9-3.0 | 1.74 +/− 0.20 |

All IL-17 ELISA values were within the detection range of the ELISA, average of duplicates

TABLE 10

| | STUDY 2 | | | |
|---|---|---|---|---|
| GROUP | RANGE OF mIL-17 VALUES, pg/mg | AVG. mIL-17, pg/mg (+/−SE) | RANGE OF CLINICAL SCORES AT SACRIFICE | AVG. CLIN. SCORE AT SACRIFICE (+/−SE) |
| CFA (n = 6) | 1.88-2.78 | 2.24 +/− 0.14 | N/A | N/A |
| CFA + MOG (n = 8) | 1.78-5.42 | 3.34 +/− 0.45 | 2.75-3.20 | 2.94 +/− 0.06 |

All IL-17 ELISA values were within the detection range of the ELISA, average of duplicates Example 13

Collagen-Induced Arthritis Model

Collagen-induced arthritis (CIA) is a widely used rodent model for rheumatoid arthritis ("RA") and has histopathological features in common with human RA. Experimental arthritis, induced in DBA/1 mice by immunization and boosting with emulsions of type II collagen, is a polyarthritic disease characterized by inflammation of the small joints and progressive erosion of cartilage and bone (Trentham, D, et al, *J. Exp. Med.* 146:857-858, 1977). Recently, Lubberts, et al, (*Arthritis & Rheunmatism,* 50:650-659, 2004; incorporated herein) demonstrated that polyclonal rabbit anti-murine IL-17 antibody, administered either at the onset or at a later stage of murine CIA, ameliorated clinical signs of arthritis.

In the CIA model, mice given a single injection of rat anti-murine IL-17 IgG2a mAb intraperitoneally (8 mg/kg R&D, MAB421 clone 50104.11) show significantly lower clinical scores than mice injected with 16 mg/kg of control rat IgG2a. The acute phase reactant, C-reactive protein (CRP), is an accepted index of disease activity in RA patients. Similar to CRP, murine serum amyloid protein (SAP) serves as an indicator of disease in the murine CIA model (Bliven, M., et al, *Arthritis & Rheumatism,* 29:1131-1138, 1986). In animals treated with 8 mg/kg of anti-murine IL-17, SAP levels were significantly lower than in those treated with control antibody. Moreover, the decrease in clinical scores and SAP values are comparable to an anti-mouse IL-1β group (8 mg/kg) used as a positive control. Finally, significant reduction in synovial inflammation at 8 mg/kg antibody and bone resorption at 16 mg/kg antibody is present compared to that of mice treated with control antibody. A dose response study may be conducted in the CIA model with anti-murine IL-17 antibody (e.g., at 0.1, 1 and 8 mg/kg). The clinical scores for rat anti-murine IL-17 display a trend for dose responsiveness.

A similar assay may be performed in cynomolgus monkeys as a model for RA using an antibody of the invention.

Example 14

Anti-IL-17 mAb Purification

A vector expressing a mAb of the invention is stably incorporated into an appropriate host cell, (e.g., CHO DG44 (dhfr-) cells (Chasin) or NSO cells) using standard procedures and purified using Protein A affinity column. Briefly, clarified conditioned media is applied to a 5 ml HiTrap rProtein A Sepharose FF column (Amersham Biosciences) that has been equilibrated with PBS (pH 7.4). The column is washed with 5 column volumes of equilibration buffer at a flow rate of 110 cm/hr to wash out nonspecific binding components. The bound antibody is eluted using a linear pH gradient (0.1 M sodium phosphate buffer pH 6.8 to 0.1 M sodium citrate buffer pH 2.5). The main protein peak in the elution is collected and its pH adjusted to neutrality with 1 M Tris buffer (pH 8.5). The protein pool is concentrated to 1-2 mg/ml using 10K Vivaspin membrane (Vivasciences) and sterile filtered (0.45 μm) before storage at 4° C.

For large preparations of a mAb of the invention, the cell free concentrate is purified over three sequential chromatography columns (Protein A, Anion Exchange, and Hydrophobic Interaction chromatography). The purity of the mAb after these chromatography steps is greater than 99% as assessed by analytical size exclusion chromatography. The mAb is exchanged into a buffer as listed below depending upon the concentration of the antibody. Chemical stability results indicate a preferred pH between 6.0 and 7.0 (inclusive); although for 20 mg/ml preparations, the pH may be between 5.5 and 7.0 (inclusive, e.g., 5.5., 5.6, 5.7., 5.8, 5.9, 6.0, 6.1, 6.2, 6.3, 6.4, 6.5, 6.6, 6.7, 6.8, 6, or 7.0). For lyophilized product, a sodium chloride level of 90-30 mM (90, 85, 80, 75, 70, 65, 60, 55, 50, 45, 40, 35 or 30 mM or any value between 30 and 90 mM) is preferred, while for a liquid formulation (e.g., to be administered subcutaneously) a sodium chloride level of 100-150 mM (100, 110, 120, 130, 140, or 150 mM or any value between 100 and 150 mM) is preferred. The product is then concentrated to a final concentration of about 10, 20 or 25 mg/ml (alternatively higher, 30, 40, 50, 60, 70, 80, 90, 100, 110, 120, 130, 140, 150 mg/ml or higher) and sterile filtered. The filtered product may be immediately frozen at −70° C. or may be lyophilized. A minimal weight ratio of 1:2 for antibody to lyoprotectant, (e.g., sucrose or trehalose) is needed for stable lyophilized formulation but is not required for a liquid formulation. Additionally, 0.02% surfactant (w/v), i.e., polysorbate-80, is added for both solution formulations and solutions to be lyophilized. The lyophilized material is resuspended in sterile Water for Injection or sterile 0.9% sodium chloride prior to administration.

TABLE 11

| mAb conc. | Buffer | pH | NaCl (mM) |
|---|---|---|---|
| 10 mg/ml | 10 mM citrate (Na) | 6.0 | 30, 50-150 |
| 20 mg/ml | 10 mM citrate | 5.5 | 50-150 |
| 20 mg/ml | 10 mM citrate | 6.0 | 50-150 |
| 20 mg/ml | 10 mM citrate | 6.5 | 50-150 |
| 20 mg/ml | 10 mM citrate | 7.0 | 50-150 |
| 20 mg/ml | 10 mM histidine | 6.5 | 150 |
| >50 mg/ml | 10 mM citrate | 5.5 | 50-150 |
| >50 mg/ml | 10 mM citrate | 6.0 | 50-150 |
| >50 mg/ml | 10 mM citrate | 6.5 | 50-150 |
| >50 mg/ml | 10 mM histidine | 6.5 | 150 |

Example 15

Antibody Half Life in vivo

Serum pharmacokinetics of antibodies of the invention (e.g., mAb 126 and 121 [IgG4 Fc region with Fab 126 or 121 respectively]) are determined after intravenous or subcutaneous administration in male cynomolgus monkeys. Concentrations of the antibodies in the serum are determined using a standard antigen-capture ELISA assay in which plates are coated with human IL-17 and bound serum antibody is detected using an anti-IgG$_4$ secondary antibody. Following intravenous administration of 1 mg/kg, mAb 126 is eliminated with a mean half-life of 6.5 days and mAb 121 is eliminated with a mean half-life of about 11 days. Following subcutaneous administration of 1 mg/kg, mAb 126 has a mean elimination half-life of 10.3 days and mAb 121 has a mean elimination half-life of 13 days.

Example 16

Tumor Xenograft Model

To establish tumor xenograft models with which to test the antitumor activity of anti-IL-17 antibodies of the invention, 5 million HCT116 colorectal carcinoma cells are mixed with Matrigel and subcutaneously injected into the left flank of 56-week-old female athymic (nu/nu) mice (Charles River laboratories, Wilmington. Mass.). Mice are treated by subcutaneous injection every 7 days with control antibodies (e.g., human IgG4 and mouse IgG1), 4 mg/kg anti-human-IL-17, 8 mg/kg anti-mouse IL-17, or combination of 4 mg/kg anti-human-IL-17 and 8 mg/kg anti-mouse-IL-17 for 4 weeks. The first antibody administration starts one day prior to implanting the cells. Tumors are measured twice each week with a caliper and body weight is monitored twice a week. Plasma is collected from each mouse at day 34 and KC levels are measured using a KC ELISA kit according to manufacturer's instructions (R&D System). In comparison with control IgG-injected mice, mice treated with the combination of anti-human IL-17 antibody and anti-mouse-IL-17 antibody have significantly reduced tumor volume. Furthermore, mice treated with both anti-human IL17 antibody and anti-mouse IL17 antibody have dramatically decreased plasma KC. The mice treated with either 4 mg/kg anti-human IL17 antibody or 8 mg/kg anti-mouse IL17 antibody revealed no significant reduction in tumor volumes and plasma KC levels. Data are shown in Tables 12 and 13 herein.

To measure IL17 level in the tumors, the tumors from mouse xenograft models are prepared largely as described in Example 9. For protein measurement, tumor lysates are diluted 1:10 in TPER+1× Halt in a polypropylene 96-well dilution plate. Protein concentration is determined by using the microplate protocol of the Coomassie Plus Protein Assay (Pierce #23236). BSA standard is diluted in TPER+Halt. IL-17 protein levels are determined using human and mouse IL-17 ELISA kits from R&D System as per manufacturer's instructions (human IL-17 DuoSet ELISA, R+D Systems, Cat. #DY317; mouse IL-17 ELISA, R+D System, Cat. # 421). Both human and mouse IL-17 were increased in tumors from HCT 116 and HT29 colon tumor xenograft models as compared to H460 lung tumor xenograft model.

TABLE 12

| | Tumor Volume (n = 10) | |
|---|---|---|
| Time, days (post implantation of HCT-116 cells) | rat IgG1 + human IgG4 isotype controls (MEAN +/− SE) | anti-mouse IL-17 + anti-human IL-17 (MEAN +/− SE) |
| 8 | 101.4 +/− 6.7 | 91.5 +/− 9.4 |
| 14 | 149.2 +/− 9.2 | 123.9 +/− 16.2 |
| 17 | 162.1 +/− 12.4 | 134.6 +/− 14.7 |
| 20 | 177.7 +/− 17.1 | 152.8 +/− 18.7 |
| 24 | 279.2 +/− 22.8 | 222.4 +/− 35.4 |
| 28 | 323.3 +/− 22.5 | 244.6 +/− 32.8 |
| 31 | 405.8 +/− 33.4 | 275.1 +/− 36.6 |
| 34 | 537.7 +/− 50.7 | 339.8 +/− 46.3 |

Tumor volume is calculated using the LogVol, AR method

TABLE 13

| | KC Chemokine Levels in Plasma 35 days post implantation (n = 10) | |
|---|---|---|
| GROUP | RANGE OF KC VALUES, pg/ml | AVG. KC, pg/ml (+/−SE) |
| Rat IgG1 + human IgG4 isotype controls | 76.3-168.4 | 112.5 +/− 10.0 |
| Anti-mouse IL-17 + anti-human IL-17% | 55.6-110.5 | 84.7 +/− 5.7 |

PERCENT AVG. KC DIFFERENCE (anti-IL-17 group compared to isotype control group): −24.7

We claim:

1. A humanized anti-IL-17 monoclonal antibody comprising a light chain variable region (LCVR) comprising a polypeptide with the amino acid sequence shown in SEQ ID NO: 241 and a heavy chain variable region (HCVR) comprising a polypeptide with the amino acid sequence as shown in SEQ ID NO: 118.

2. A humanized anti-IL-17 monoclonal antibody comprising two polypeptide chains of a light chain variable region (LCVR) with the amino acid sequence shown in SEQ ID NO: 241 and two polypeptide chains of a heavy chain variable region (HCVR) with the amino acid sequence as shown in SEQ ID NO: 118.

3. A composition comprising the antibody according to claim 2.

4. The composition of claim 3 further comprising a pharmaceutically acceptable carrier.

* * * * *

UNITED STATES PATENT AND TRADEMARK OFFICE
CERTIFICATE OF CORRECTION

| | |
|---|---|
| PATENT NO. | : 7,838,638 B2 |
| APPLICATION NO. | : 12/095398 |
| DATED | : November 23, 2010 |
| INVENTOR(S) | : Barrett Allan et al. |

It is certified that error appears in the above-identified patent and that said Letters Patent is hereby corrected as shown below:

Title Page; item (75);

Insert the following name, on the front page of the patent, in the list of inventors:

--Ying Tang--

Signed and Sealed this
Twenty-second Day of March, 2011

David J. Kappos
*Director of the United States Patent and Trademark Office*

SEQUENCE LISTING

<160> NUMBER OF SEQ ID NOS: 284

<210> SEQ ID NO 1
<211> LENGTH: 155
<212> TYPE: PRT
<213> ORGANISM: Homo sapiens

<400> SEQUENCE: 1

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
                35                  40                  45

Leu Asn Ile His Asn Arg Asn Thr Asn Thr Asn Pro Lys Arg Ser Ser
            50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
                115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 2
<211> LENGTH: 178
<212> TYPE: PRT
<213> ORGANISM: Homo sapiens

<400> SEQUENCE: 2

Met Asp Trp Pro His Asn Leu Leu Phe Leu Leu Thr Ile Ser Ile Phe
1               5                   10                  15

Leu Gly Leu Gly Pro Trp Pro Lys Trp Lys Arg Lys Gly Gln Gly Arg
                20                  25                  30

Pro Gly Pro Leu Ala Pro Gly Pro His Gln Val Pro Leu Asp Leu Val
                35                  40                  45

Ser Arg Met Lys Pro Tyr Ala Arg Met Glu Glu Tyr Glu Arg Asn Ile
            50                  55                  60

Glu Glu Met Val Ala Gln Leu Arg Asn Ser Ser Glu Leu Ala Gln Arg
65                  70                  75                  80

Lys Cys Glu Val Asn Leu Gln Leu Trp Met Ser Asn Lys Arg Ser Leu
                85                  90                  95

Ser Pro Trp Gly Tyr Ser Ile Asn His Asp Pro Ser Arg Ile Pro Val
                100                 105                 110

Asp Leu Pro Glu Ala Arg Cys Leu Cys Leu Gly Cys Val Asn Pro Phe
            115                 120                 125

Thr Met Trp Glu Asp Arg Ser Met Val Ser Val Pro Val Phe Ser Gln
            130                 135                 140

Val Pro Val Arg Arg Arg Leu Cys Pro Pro Pro Arg Thr Gly Pro
145                 150                 155                 160

```
Cys Arg Gln Arg Ala Val Met Glu Thr Ile Ala Val Gly Cys Thr Cys
                165                 170                 175
Ile Phe

<210> SEQ ID NO 3
<211> LENGTH: 196
<212> TYPE: PRT
<213> ORGANISM: Homo sapiens

<400> SEQUENCE: 3

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30

Thr Pro His Cys Tyr Ser Ala Glu Glu Leu Pro Leu Gln Ala Pro Pro
        35                  40                  45

His Leu Ile Ala Arg Gly Ala Lys Trp Gly Gln Ala Leu Pro Val Ala
    50                  55                  60

Leu Val Ser Ser Leu Glu Ala Ala Ser His Arg Gly Arg His Glu Arg
65                  70                  75                  80

Pro Ser Ala Thr Thr Gln Cys Pro Val Leu Arg Pro Glu Glu Val Leu
                85                  90                  95

Glu Ala Asp Thr His Gln Arg Ser Ile Ser Pro Trp Arg Tyr Arg Val
            100                 105                 110

Asp Thr Asp Glu Asp Arg Tyr Pro Gln Lys Leu Ala Phe Ala Glu Cys
        115                 120                 125

Leu Cys Arg Gly Cys Ile Asp Ala Arg Thr Gly Arg Glu Thr Ala Ala
    130                 135                 140

Leu Asn Ser Val Arg Leu Leu Gln Ser Leu Leu Val Leu Arg Arg Arg
145                 150                 155                 160

Pro Cys Ser Arg Asp Gly Ser Gly Leu Pro Thr Pro Gly Ala Phe Ala
                165                 170                 175

Phe His Thr Glu Phe Ile His Val Pro Val Gly Cys Thr Cys Val Leu
            180                 185                 190

Pro Arg Ser Val
        195

<210> SEQ ID NO 4
<211> LENGTH: 202
<212> TYPE: PRT
<213> ORGANISM: Homo sapiens

<400> SEQUENCE: 4

Met Leu Val Ala Gly Phe Leu Leu Ala Leu Pro Pro Ser Trp Ala Ala
1               5                   10                  15

Gly Ala Pro Arg Ala Gly Arg Arg Pro Ala Arg Pro Gly Cys Ala
            20                  25                  30

Asp Arg Pro Glu Glu Leu Leu Glu Gln Leu Tyr Gly Arg Leu Ala Ala
        35                  40                  45

Gly Val Leu Ser Ala Phe His His Thr Leu Gln Leu Gly Pro Arg Glu
    50                  55                  60

Gln Ala Arg Asn Ala Ser Cys Pro Ala Gly Gly Arg Pro Ala Asp Arg
65                  70                  75                  80

Arg Phe Arg Pro Pro Thr Asn Leu Arg Ser Val Ser Pro Trp Ala Tyr
                85                  90                  95
```

```
Arg Ile Ser Tyr Asp Pro Ala Arg Tyr Pro Arg Tyr Leu Pro Glu Ala
            100                 105                 110

Tyr Cys Leu Cys Arg Gly Cys Leu Thr Gly Leu Phe Gly Glu Glu Asp
            115                 120                 125

Val Arg Phe Arg Ser Ala Pro Val Tyr Met Pro Thr Val Val Leu Arg
        130                 135                 140

Arg Thr Pro Ala Cys Ala Gly Gly Arg Ser Val Tyr Thr Glu Ala Tyr
145                 150                 155                 160

Val Thr Ile Pro Val Gly Cys Thr Cys Val Pro Glu Pro Glu Lys Asp
                165                 170                 175

Ala Asp Ser Ile Asn Ser Ser Ile Asp Lys Gln Gly Ala Lys Leu Leu
            180                 185                 190

Leu Gly Pro Asn Asp Ala Pro Ala Gly Pro
            195                 200

<210> SEQ ID NO 5
<211> LENGTH: 177
<212> TYPE: PRT
<213> ORGANISM: Homo sapiens

<400> SEQUENCE: 5

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Phe Phe
145                 150                 155                 160

Leu Tyr Arg Val Ser Leu Ala Cys Val Cys Val Arg Pro Arg Val Met
                165                 170                 175

Gly

<210> SEQ ID NO 6
<211> LENGTH: 132
<212> TYPE: PRT
<213> ORGANISM: Homo sapiens

<400> SEQUENCE: 6

Met Val Lys Tyr Leu Leu Leu Ser Ile Leu Gly Leu Ala Phe Leu Ser
1               5                   10                  15

Glu Ala Ala Ala Arg Lys Ile Pro Lys Val Gly His Thr Phe Phe Gln
            20                  25                  30

Lys Pro Glu Ser Cys Ser Met Ser Arg Asn Ile Glu Ser Arg Ser Thr
```

-continued

```
                35                  40                  45
Ser Pro Trp Asn Tyr Thr Val Thr Trp Asp Pro Asn Arg Tyr Pro Ser
 50                  55                  60

Glu Val Val Gln Ala Gln Cys Arg Asn Leu Gly Cys Ile Asn Ala Gln
 65                  70                  75                  80

Gly Lys Glu Asp Ile Ser Met Asn Ser Val Pro Ile Gln Gln Glu Thr
                 85                  90                  95

Leu Val Val Arg Arg Lys His Gln Gly Cys Ser Val Ser Phe Gln Leu
                100                 105                 110

Glu Lys Val Leu Val Thr Val Gly Cys Thr Cys Val Thr Pro Val Ile
                115                 120                 125

His His Val Gln
                130

<210> SEQ ID NO 7
<211> LENGTH: 158
<212> TYPE: PRT
<213> ORGANISM: Mus sp.

<400> SEQUENCE: 7

Met Ser Pro Gly Arg Ala Ser Ser Val Ser Leu Met Leu Leu Leu Leu
  1               5                  10                  15

Leu Ser Leu Ala Ala Thr Val Lys Ala Ala Ile Ile Pro Gln Ser
                 20                  25                  30

Ser Ala Cys Pro Asn Thr Glu Ala Lys Asp Phe Leu Gln Asn Val Lys
                 35                  40                  45

Val Asn Leu Lys Val Phe Asn Ser Leu Gly Ala Lys Val Ser Ser Arg
 50                  55                  60

Arg Pro Ser Asp Tyr Leu Asn Arg Ser Thr Ser Pro Trp Thr Leu His
 65                  70                  75                  80

Arg Asn Glu Asp Pro Asp Arg Tyr Pro Ser Val Ile Trp Glu Ala Gln
                 85                  90                  95

Cys Arg His Gln Arg Cys Val Asn Ala Glu Gly Lys Leu Asp His His
                100                 105                 110

Met Asn Ser Val Leu Ile Gln Gln Glu Ile Leu Val Leu Lys Arg Glu
                115                 120                 125

Pro Glu Ser Cys Pro Phe Thr Phe Arg Val Glu Lys Met Leu Val Gly
                130                 135                 140

Val Gly Cys Thr Cys Val Ala Ser Ile Val Arg Gln Ala Ala
145                 150                 155

<210> SEQ ID NO 8
<211> LENGTH: 158
<212> TYPE: PRT
<213> ORGANISM: Rattus rattus

<400> SEQUENCE: 8

Met Ser Pro Arg Arg Ile Pro Ser Met Cys Leu Met Leu Leu Leu Leu
  1               5                  10                  15

Leu Asn Leu Glu Ala Thr Val Lys Ala Ala Val Leu Ile Pro Gln Ser
                 20                  25                  30

Ser Val Cys Pro Asn Ala Glu Ala Asn Asn Phe Leu Gln Asn Val Lys
                 35                  40                  45

Val Asn Leu Lys Val Ile Asn Ser Leu Ser Ser Lys Ala Ser Ser Arg
 50                  55                  60

Arg Pro Ser Asp Tyr Leu Asn Arg Ser Thr Ser Pro Trp Thr Leu Ser
```

```
                65                  70                  75                  80
Arg Asn Glu Asp Pro Asp Arg Tyr Pro Ser Val Ile Trp Glu Ala Gln
                    85                  90                  95

Cys Arg His Gln Arg Cys Val Asn Ala Glu Gly Lys Leu Asp His His
                100                 105                 110

Met Asn Ser Val Leu Ile Gln Gln Glu Ile Leu Val Leu Lys Arg Glu
            115                 120                 125

Pro Glu Lys Cys Pro Phe Thr Phe Arg Val Glu Lys Met Leu Val Gly
        130                 135                 140

Val Gly Cys Thr Cys Val Ser Ser Ile Val Arg His Ala Ser
145                 150                 155

<210> SEQ ID NO 9
<211> LENGTH: 153
<212> TYPE: PRT
<213> ORGANISM: Oryctolagus cuniculus

<400> SEQUENCE: 9

Met Ser Leu Gly Arg Ile Ser Ser Val Ser Leu Leu Leu Leu Leu Cys
1               5                   10                  15

Leu Val Ala Thr Val Lys Asn Gly Ile Ala Met Pro Arg Asn Pro Gly
            20                  25                  30

Cys Pro Asn Ala Glu Asp Lys Asn Phe Pro Gln Asn Val Lys Val Ser
        35                  40                  45

Leu Asn Ile Leu Asn Lys Ser Val Asn Ser Arg Arg Pro Ser Asp Tyr
    50                  55                  60

Tyr Asn Arg Ser Thr Ser Pro Trp Thr Leu His Arg Asn Glu Asp Arg
65                  70                  75                  80

Glu Arg Tyr Pro Ser Val Ile Trp Glu Ala Lys Cys Arg His Leu Gly
                85                  90                  95

Cys Val Asn Ala Glu Gly Asn Glu Asp His His Met Asn Ser Val Pro
            100                 105                 110

Ile Gln Gln Glu Ile Leu Val Leu Arg Arg Glu Ser Gln His Cys Pro
        115                 120                 125

His Ser Phe Arg Leu Glu Lys Met Leu Val Ala Val Gly Cys Thr Cys
    130                 135                 140

Val Thr Pro Ile Ile His His Met Ala
145                 150

<210> SEQ ID NO 10
<211> LENGTH: 155
<212> TYPE: PRT
<213> ORGANISM: Macaca fascicularis

<400> SEQUENCE: 10

Met Thr Pro Gly Lys Thr Ser Leu Val Leu Leu Leu Leu Leu Leu Ser
1               5                   10                  15

Leu Glu Ala Ile Val Lys Ala Gly Ile Ala Ile Pro Arg Asn Ser Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Ser Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
```

```
                    85                  90                  95
Leu Gly Cys Val Lys Ala Asp Gly Asn Val Asp Tyr His Met Asn Ser
            100                 105                 110
Val Pro Ile Gln Gln Glu Ile Leu Val Leu Arg Arg Glu Pro Arg His
        115                 120                 125
Cys Pro Asn Ser Phe Arg Leu Glu Lys Ile Leu Val Ser Val Gly Cys
    130                 135                 140
Thr Cys Val Thr Pro Ile Val His His Val Ala
145                 150                 155

<210> SEQ ID NO 11
<211> LENGTH: 10
<212> TYPE: PRT
<213> ORGANISM: Artificial
<220> FEATURE:
<223> OTHER INFORMATION: Synthetic construct

<400> SEQUENCE: 11

Gly Tyr Ser Phe Thr Asp Tyr Asn Met Asn
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic construct

<400> SEQUENCE: 12

Gly Tyr Ser Phe Thr Asp Tyr Asn Ile Asn
1               5                   10

<210> SEQ ID NO 13
<211> LENGTH: 10
<212> TYPE: PRT
<213> ORGANISM: Artificial
<220> FEATURE:
<223> OTHER INFORMATION: Synthetic construct

<400> SEQUENCE: 13

Gly Tyr Ser Phe Thr Asp Tyr Asn Leu Asn
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic construct

<400> SEQUENCE: 14

Gly Tyr Ser Phe Gly Asp Tyr Asn Met Asn
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic construct

<400> SEQUENCE: 15

Gly Tyr Ser Phe Arg Asp Tyr Asn Met Asn
1               5                   10
```

```
<210> SEQ ID NO 16
<211> LENGTH: 10
<212> TYPE: PRT
<213> ORGANISM: Artificial
<220> FEATURE:
<223> OTHER INFORMATION: Synthetic construct

<400> SEQUENCE: 16

Gly Tyr Ser Phe Thr Trp Tyr Asn Met Asn
1               5                   10

<210> SEQ ID NO 17
<211> LENGTH: 10
<212> TYPE: PRT
<213> ORGANISM: Artificial
<220> FEATURE:
<223> OTHER INFORMATION: Synthetic construct

<400> SEQUENCE: 17

Gly Tyr Ser Phe Asn Asp Tyr Asn Met Asn
1               5                   10

<210> SEQ ID NO 18
<211> LENGTH: 10
<212> TYPE: PRT
<213> ORGANISM: Artificial
<220> FEATURE:
<223> OTHER INFORMATION: Synthetic construct

<400> SEQUENCE: 18

Gly Tyr Ser Phe Thr Asp Tyr Asn Met Ser
1               5                   10

<210> SEQ ID NO 19
<211> LENGTH: 10
<212> TYPE: PRT
<213> ORGANISM: Artificial
<220> FEATURE:
<223> OTHER INFORMATION: Synthetic construct

<400> SEQUENCE: 19

Gly Tyr Ser Phe Thr Asp Tyr Asn Thr Asn
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic construct

<400> SEQUENCE: 20

Gly Tyr Ser Phe Pro Asp Tyr Asn Met Asn
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic construct

<400> SEQUENCE: 21

His Tyr Ser Phe Thr Asp Tyr Asn Met Asn
1               5                   10
```

```
<210> SEQ ID NO 22
<211> LENGTH: 10
<212> TYPE: PRT
<213> ORGANISM: Artificial
<220> FEATURE:
<223> OTHER INFORMATION: Synthetic construct

<400> SEQUENCE: 22

Gly Tyr His Phe Thr Asp Tyr Asn Met Asn
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic construct

<400> SEQUENCE: 23

Gly Tyr Pro Phe Thr Asp Tyr Asn Met Asn
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic construct

<400> SEQUENCE: 24

Gly Tyr Ser Phe Thr Asp Phe Asn Met Asn
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic construct

<400> SEQUENCE: 25

Gly Tyr Ser Phe Thr Asp Tyr His Leu Gly
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic construct

<400> SEQUENCE: 26

Gly Tyr Ser Phe Thr Asp Tyr His Ile His
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic construct

<400> SEQUENCE: 27

Gly Tyr Ser Phe Thr Asp Tyr His Met Ser
1               5                   10

<210> SEQ ID NO 28
```

-continued

```
<211> LENGTH: 10
<212> TYPE: PRT
<213> ORGANISM: Artificial
<220> FEATURE:
<223> OTHER INFORMATION: Synthetic construct

<400> SEQUENCE: 28

Gly Tyr Ser Phe Thr Asp Tyr His Ile Ser
1               5                   10

<210> SEQ ID NO 29
<211> LENGTH: 16
<212> TYPE: PRT
<213> ORGANISM: Artificial
<220> FEATURE:
<223> OTHER INFORMATION: Synthetic construct

<400> SEQUENCE: 29

Val Ile Asn Pro Asn Tyr Gly Thr Thr Asp Tyr Asn Gln Arg Phe Lys
1               5                   10                  15

<210> SEQ ID NO 30
<211> LENGTH: 16
<212> TYPE: PRT
<213> ORGANISM: Artificial
<220> FEATURE:
<223> OTHER INFORMATION: Synthetic construct

<400> SEQUENCE: 30

Val Ile Asn Pro Met Tyr Gly Thr Thr Asp Tyr Asn Gln Arg Phe Lys
1               5                   10                  15

<210> SEQ ID NO 31
<211> LENGTH: 16
<212> TYPE: PRT
<213> ORGANISM: Artificial
<220> FEATURE:
<223> OTHER INFORMATION: Synthetic construct

<400> SEQUENCE: 31

Val Ile Asn Pro Ala Tyr Gly Thr Thr Asp Tyr Asn Gln Arg Phe Lys
1               5                   10                  15

<210> SEQ ID NO 32
<211> LENGTH: 16
<212> TYPE: PRT
<213> ORGANISM: Artificial
<220> FEATURE:
<223> OTHER INFORMATION: Synthetic construct

<400> SEQUENCE: 32

Val Ile Asn Pro Glu Tyr Gly Thr Thr Asp Tyr Asn Gln Arg Phe Lys
1               5                   10                  15

<210> SEQ ID NO 33
<211> LENGTH: 10
<212> TYPE: PRT
<213> ORGANISM: Artificial
<220> FEATURE:
<223> OTHER INFORMATION: Synthetic construct

<400> SEQUENCE: 33

Tyr Asp Tyr Ala Thr Gly Thr Gly Ala Tyr
1               5                   10

<210> SEQ ID NO 34
<211> LENGTH: 10
```

```
<212> TYPE: PRT
<213> ORGANISM: Artificial
<220> FEATURE:
<223> OTHER INFORMATION: Synthetic construct

<400> SEQUENCE: 34

Tyr Asp Tyr Trp Thr Gly Thr Gly Gly Tyr
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic construct

<400> SEQUENCE: 35

Tyr Asp Tyr Trp Thr Gly Thr Gly Ala Tyr
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic construct

<400> SEQUENCE: 36

Tyr Asp Tyr Ala Thr Gly Thr Gly Leu Tyr
1               5                   10

<210> SEQ ID NO 37
<211> LENGTH: 10
<212> TYPE: PRT
<213> ORGANISM: Artificial
<220> FEATURE:
<223> OTHER INFORMATION: Synthetic construct

<400> SEQUENCE: 37

Tyr Asp Tyr Ala Thr Gly Thr Gly Gly Tyr
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic construct

<400> SEQUENCE: 38

Tyr Asp Tyr Ala Thr Gly Thr Gly Val Tyr
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic construct

<400> SEQUENCE: 39

Tyr Asp Tyr His Thr Gly Thr Gly Gly Tyr
1               5                   10

<210> SEQ ID NO 40
<211> LENGTH: 10
<212> TYPE: PRT
```

```
<213> ORGANISM: Artificial
<220> FEATURE:
<223> OTHER INFORMATION: Synthetic construct

<400> SEQUENCE: 40

Tyr Asp Tyr Ala Thr Gly Thr Gly Thr Tyr
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic construct

<400> SEQUENCE: 41

Tyr Asp Tyr Phe Thr Gly Thr Gly Gly Tyr
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic construct

<400> SEQUENCE: 42

Tyr Asp Tyr Phe Thr Gly Thr Gly Pro Tyr
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic construct

<400> SEQUENCE: 43

Tyr Asp Tyr Tyr Thr Gly Thr Gly Gly Tyr
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic construct

<400> SEQUENCE: 44

Tyr Asp Tyr Ser Thr Gly Thr Gly Gly Tyr
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic construct

<400> SEQUENCE: 45

Tyr Asp Tyr Ser Thr Gly Thr Gly Ala Tyr
1               5                   10

<210> SEQ ID NO 46
<211> LENGTH: 10
<212> TYPE: PRT
<213> ORGANISM: Artificial
```

```
<220> FEATURE:
<223> OTHER INFORMATION: Synthetic construct

<400> SEQUENCE: 46

Tyr Asp Ala Phe Thr Gly Thr Gly Ala Tyr
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic construct

<400> SEQUENCE: 47

Tyr Asp Tyr Tyr Thr Gly Thr Gly Ala Tyr
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic construct

<400> SEQUENCE: 48

Tyr Asp Tyr His Thr Gly Thr Gly Ala Tyr
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic construct

<400> SEQUENCE: 49

Tyr Asp Tyr Leu Thr Gly Thr Gly Ala Tyr
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic construct

<400> SEQUENCE: 50

Tyr Asp Tyr Ala Thr Ser Thr Gly Ala Tyr
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic construct

<400> SEQUENCE: 51

Tyr Asp Tyr Ala Pro Gly Thr Gly Ala Tyr
1               5                   10

<210> SEQ ID NO 52
<211> LENGTH: 10
<212> TYPE: PRT
<213> ORGANISM: Artificial
<220> FEATURE:
```

<223> OTHER INFORMATION: Synthetic construct

<400> SEQUENCE: 52

Tyr Asp Tyr Phe Thr Gly Thr Gly Val Tyr
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic construct

<400> SEQUENCE: 53

Tyr Asp Tyr Tyr Thr Gly Thr Gly Val Tyr
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic construct

<400> SEQUENCE: 54

Tyr Asp Pro Ala Thr Gly Thr Gly Ala Tyr
1               5                   10

<210> SEQ ID NO 55
<211> LENGTH: 10
<212> TYPE: PRT
<213> ORGANISM: Artificial
<220> FEATURE:
<223> OTHER INFORMATION: Synthetic construct

<400> SEQUENCE: 55

Tyr Asp Tyr His Thr Gly Thr Gly Val Tyr
1               5                   10

<210> SEQ ID NO 56
<211> LENGTH: 119
<212> TYPE: PRT
<213> ORGANISM: Artificial
<220> FEATURE:
<223> OTHER INFORMATION: Synthetic construct

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 57
<211> LENGTH: 119
<212> TYPE: PRT
<213> ORGANISM: Artificial
<220> FEATURE:
<223> OTHER INFORMATION: Synthetic construct

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Trp Thr Gly Thr Gly Gly Tyr Trp Gly Gln Gly
            100                 105                 110

Thr Leu Val Thr Val Ser Ser
        115
```

<210> SEQ ID NO 58
<211> LENGTH: 119
<212> TYPE: PRT
<213> ORGANISM: Artificial
<220> FEATURE:
<223> OTHER INFORMATION: Synthetic construct

<400> SEQUENCE: 58

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Trp Thr Gly Thr Gly Ala Tyr Trp Gly Gln Gly
            100                 105                 110

Thr Leu Val Thr Val Ser Ser
        115
```

<210> SEQ ID NO 59
<211> LENGTH: 119
<212> TYPE: PRT
<213> ORGANISM: Artificial
<220> FEATURE:
<223> OTHER INFORMATION: Synthetic construct

<400> SEQUENCE: 59

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Leu Tyr Trp Gly Gln Gly
                100                 105                 110

Thr Leu Val Thr Val Ser Ser
        115

<210> SEQ ID NO 60
<211> LENGTH: 119
<212> TYPE: PRT
<213> ORGANISM: Artificial
<220> FEATURE:
<223> OTHER INFORMATION: Synthetic construct

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Gly Tyr Trp Gly Gln Gly
                100                 105                 110

Thr Leu Val Thr Val Ser Ser
        115

<210> SEQ ID NO 61
<211> LENGTH: 119
<212> TYPE: PRT
<213> ORGANISM: Artificial
<220> FEATURE:
<223> OTHER INFORMATION: Synthetic construct

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

```
Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Val Tyr Trp Gly Gln Gly
            100                 105                 110

Thr Leu Val Thr Val Ser Ser
        115
```

<210> SEQ ID NO 62
<211> LENGTH: 119
<212> TYPE: PRT
<213> ORGANISM: Artificial
<220> FEATURE:
<223> OTHER INFORMATION: Synthetic construct

<400> SEQUENCE: 62

```
Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ser Phe Thr Asp Tyr
             20                  25                  30

Asn Met Asn Trp Val Arg Gln Ala Pro Gly Gln Gly Leu Glu Trp Met
         35                  40                  45

Gly Val Ile Asn Pro Asn Tyr Gly Thr Thr Asp Tyr Asn Gln Arg Phe
     50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr His Thr Gly Thr Gly Gly Tyr Trp Gly Gln Gly
            100                 105                 110

Thr Leu Val Thr Val Ser Ser
        115
```

<210> SEQ ID NO 63
<211> LENGTH: 119
<212> TYPE: PRT
<213> ORGANISM: Artificial
<220> FEATURE:
<223> OTHER INFORMATION: Synthetic construct

<400> SEQUENCE: 63

```
Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ser Phe Thr Asp Tyr
             20                  25                  30

Asn Met Asn Trp Val Arg Gln Ala Pro Gly Gln Gly Leu Glu Trp Met
         35                  40                  45

Gly Val Ile Asn Pro Asn Tyr Gly Thr Thr Asp Tyr Asn Gln Arg Phe
     50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Tyr Trp Gly Gln Gly
            100                 105                 110

Thr Leu Val Thr Val Ser Ser
```

```
<210> SEQ ID NO 64
<211> LENGTH: 119
<212> TYPE: PRT
<213> ORGANISM: Artificial
<220> FEATURE:
<223> OTHER INFORMATION: Synthetic construct

<400> SEQUENCE: 64

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
Asn Met Asn Trp Val Arg Gln Ala Pro Gly Gln Gly Leu Glu Trp Met
        35                  40                  45
Gly Val Ile Asn Pro Asn Tyr Gly Thr Thr Asp Tyr Asn Gln Arg Phe
    50                  55                  60
Lys Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Tyr Phe Thr Gly Thr Gly Gly Tyr Trp Gly Gln Gly
            100                 105                 110
Thr Leu Val Thr Val Ser Ser
        115

<210> SEQ ID NO 65
<211> LENGTH: 119
<212> TYPE: PRT
<213> ORGANISM: Artificial
<220> FEATURE:
<223> OTHER INFORMATION: Synthetic construct

<400> SEQUENCE: 65

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
Asn Met Asn Trp Val Arg Gln Ala Pro Gly Gln Gly Leu Glu Trp Met
        35                  40                  45
Gly Val Ile Asn Pro Asn Tyr Gly Thr Thr Asp Tyr Asn Gln Arg Phe
    50                  55                  60
Lys Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Tyr Phe Thr Gly Thr Gly Pro Tyr Trp Gly Gln Gly
            100                 105                 110
Thr Leu Val Thr Val Ser Ser
        115

<210> SEQ ID NO 66
<211> LENGTH: 119
<212> TYPE: PRT
<213> ORGANISM: Artificial
<220> FEATURE:
<223> OTHER INFORMATION: Synthetic construct

<400> SEQUENCE: 66
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Tyr Thr Gly Thr Gly Gly Tyr Trp Gly Gln Gly
            100                 105                 110

Thr Leu Val Thr Val Ser Ser
        115

<210> SEQ ID NO 67
<211> LENGTH: 119
<212> TYPE: PRT
<213> ORGANISM: Artificial
<220> FEATURE:
<223> OTHER INFORMATION: Synthetic construct

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Ser Thr Gly Thr Gly Gly Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Artificial
<220> FEATURE:
<223> OTHER INFORMATION: Synthetic construct

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Ile Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe

```
                  50                  55                  60
Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 69
<211> LENGTH: 119
<212> TYPE: PRT
<213> ORGANISM: Artificial
<220> FEATURE:
<223> OTHER INFORMATION: Synthetic construct

<400> SEQUENCE: 69

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Thr Asp Tyr
                 20                  25                  30

Asn Leu Asn Trp Val Arg Gln Ala Pro Gly Gln Gly Leu Glu Trp Met
             35                  40                  45

Gly Val Ile Asn Pro Asn Tyr Gly Thr Thr Asp Tyr Asn Gln Arg Phe
         50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 70
<211> LENGTH: 119
<212> TYPE: PRT
<213> ORGANISM: Artificial
<220> FEATURE:
<223> OTHER INFORMATION: Synthetic construct

<400> SEQUENCE: 70

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Gly Asp Tyr
                 20                  25                  30

Asn Met Asn Trp Val Arg Gln Ala Pro Gly Gln Gly Leu Glu Trp Met
             35                  40                  45

Gly Val Ile Asn Pro Asn Tyr Gly Thr Thr Asp Tyr Asn Gln Arg Phe
         50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110
```

Thr Leu Val Thr Val Ser Ser
        115

<210> SEQ ID NO 71
<211> LENGTH: 119
<212> TYPE: PRT
<213> ORGANISM: Artificial
<220> FEATURE:
<223> OTHER INFORMATION: Synthetic construct

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Arg Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial
<220> FEATURE:
<223> OTHER INFORMATION: Synthetic construct

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Trp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 73
<211> LENGTH: 119
<212> TYPE: PRT
<213> ORGANISM: Artificial
<220> FEATURE:
<223> OTHER INFORMATION: Synthetic construct

```
<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Asn Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 74
<211> LENGTH: 119
<212> TYPE: PRT
<213> ORGANISM: Artificial
<220> FEATURE:
<223> OTHER INFORMATION: Synthetic construct

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Ser Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 75
<211> LENGTH: 119
<212> TYPE: PRT
<213> ORGANISM: Artificial
<220> FEATURE:
<223> OTHER INFORMATION: Synthetic construct

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Thr Asn Trp Val Arg Gln Ala Pro Gly Gln Gly Leu Glu Trp Met
        35                  40                  45
```

Gly Val Ile Asn Pro Asn Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 76
<211> LENGTH: 119
<212> TYPE: PRT
<213> ORGANISM: Artificial
<220> FEATURE:
<223> OTHER INFORMATION: Synthetic construct

<400> SEQUENCE: 76

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Pro Asp Tyr
                 20                  25                  30

Asn Met Asn Trp Val Arg Gln Ala Pro Gly Gln Gly Leu Glu Trp Met
             35                  40                  45

Gly Val Ile Asn Pro Asn Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 77
<211> LENGTH: 119
<212> TYPE: PRT
<213> ORGANISM: Artificial
<220> FEATURE:
<223> OTHER INFORMATION: Synthetic construct

<400> SEQUENCE: 77

Gln Val Gln Leu Val Gln Ser Gly Ala Glu Val Lys Lys Pro Gly Ser
 1               5                  10                  15

Ser Val Lys Val Ser Cys Lys Ala Ser His Tyr Ser Phe Thr Asp Tyr
                 20                  25                  30

Asn Met Asn Trp Val Arg Gln Ala Pro Gly Gln Gly Leu Glu Trp Met
             35                  40                  45

Gly Val Ile Asn Pro Asn Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Thr Gly Thr Gly Ala Tyr Trp Gly Gln Gly
                100                 105                 110

```
Thr Leu Val Thr Val Ser Ser
        115

<210> SEQ ID NO 78
<211> LENGTH: 119
<212> TYPE: PRT
<213> ORGANISM: Artificial
<220> FEATURE:
<223> OTHER INFORMATION: Synthetic construct

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser Gly Tyr His Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 79
<211> LENGTH: 119
<212> TYPE: PRT
<213> ORGANISM: Artificial
<220> FEATURE:
<223> OTHER INFORMATION: Synthetic construct

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Pro Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 80
<211> LENGTH: 119
<212> TYPE: PRT
<213> ORGANISM: Artificial
<220> FEATURE:
<223> OTHER INFORMATION: Synthetic construct
```

-continued

```
<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Phe
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 81
<211> LENGTH: 119
<212> TYPE: PRT
<213> ORGANISM: Artificial
<220> FEATURE:
<223> OTHER INFORMATION: Synthetic construct

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
            100                 105                 110

Thr Leu Val Thr Val Ser Ser
        115

<210> SEQ ID NO 82
<211> LENGTH: 119
<212> TYPE: PRT
<213> ORGANISM: Artificial
<220> FEATURE:
<223> OTHER INFORMATION: Synthetic construct

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45
```

Gly Val Ile Asn Pro Ala Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 83
<211> LENGTH: 119
<212> TYPE: PRT
<213> ORGANISM: Artificial
<220> FEATURE:
<223> OTHER INFORMATION: Synthetic construct

<400> SEQUENCE: 83

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Glu Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
                100                 105                 110

Thr Leu Val Thr Val Ser Ser
            115

<210> SEQ ID NO 84
<211> LENGTH: 119
<212> TYPE: PRT
<213> ORGANISM: Artificial
<220> FEATURE:
<223> OTHER INFORMATION: Synthetic construct

<400> SEQUENCE: 84

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Tyr Asp Tyr Ser Thr Gly Thr Gly Ala Tyr Trp Gly Gln Gly

Thr Leu Val Thr Val Ser Ser
        115

<210> SEQ ID NO 85
<211> LENGTH: 119
<212> TYPE: PRT
<213> ORGANISM: Artificial
<220> FEATURE:
<223> OTHER INFORMATION: Synthetic construct

<400> SEQUENCE: 85

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 86
<211> LENGTH: 119
<212> TYPE: PRT
<213> ORGANISM: Artificial
<220> FEATURE:
<223> OTHER INFORMATION: Synthetic construct

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Ala Tyr Trp Gly Gln Gly
            100                 105                 110

Thr Leu Val Thr Val Ser Ser
        115

<210> SEQ ID NO 87
<211> LENGTH: 119
<212> TYPE: PRT
<213> ORGANISM: Artificial
<220> FEATURE:

-continued

<223> OTHER INFORMATION: Synthetic construct

<400> SEQUENCE: 87

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
Asn Met Asn Trp Val Arg Gln Ala Pro Gly Gln Gly Leu Glu Trp Met
        35                  40                  45
Gly Val Ile Asn Pro Asn Tyr Gly Thr Thr Asp Tyr Asn Gln Arg Phe
    50                  55                  60
Lys Gly Arg Val Thr Ile Thr Ala Asp Glu Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Tyr His Thr Gly Thr Gly Ala Tyr Trp Gly Gln Gly
            100                 105                 110
Thr Leu Val Thr Val Ser Ser
        115
```

<210> SEQ ID NO 88
<211> LENGTH: 119
<212> TYPE: PRT
<213> ORGANISM: Artificial
<220> FEATURE:
<223> OTHER INFORMATION: Synthetic construct

<400> SEQUENCE: 88

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
Asn Met Asn Trp Val Arg Gln Ala Pro Gly Gln Gly Leu Glu Trp Met
        35                  40                  45
Gly Val Ile Asn Pro Asn Tyr Gly Thr Thr Asp Tyr Asn Gln Arg Phe
    50                  55                  60
Lys Gly Arg Val Thr Ile Thr Ala Asp Glu Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Tyr Leu Thr Gly Thr Gly Ala Tyr Trp Gly Gln Gly
            100                 105                 110
Thr Leu Val Thr Val Ser Ser
        115
```

<210> SEQ ID NO 89
<211> LENGTH: 119
<212> TYPE: PRT
<213> ORGANISM: Artificial
<220> FEATURE:
<223> OTHER INFORMATION: Synthetic construct

<400> SEQUENCE: 89

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Asp Tyr
            20                  25                  30
Asn Met Asn Trp Val Arg Gln Ala Pro Gly Gln Gly Leu Glu Trp Met
```

```
                35                  40                  45
Gly Val Ile Asn Pro Asn Tyr Gly Thr Thr Asp Tyr Asn Gln Arg Phe
         50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Tyr Asp Tyr Ala Thr Ser Thr Gly Ala Tyr Trp Gly Gln Gly
                100                 105                 110
Thr Leu Val Thr Val Ser Ser
                115

<210> SEQ ID NO 90
<211> LENGTH: 119
<212> TYPE: PRT
<213> ORGANISM: Artificial
<220> FEATURE:
<223> OTHER INFORMATION: Synthetic construct

<400> SEQUENCE: 90

Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Ser Phe Thr Asp Tyr
                 20                  25                  30
Asn Met Asn Trp Val Arg Gln Ala Pro Gly Gln Gly Leu Glu Trp Met
             35                  40                  45
Gly Val Ile Asn Pro Asn Tyr Gly Thr Thr Asp Tyr Asn Gln Arg Phe
         50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Tyr Asp Tyr Ala Pro Gly Thr Gly Ala Tyr Trp Gly Gln Gly
                100                 105                 110
Thr Leu Val Thr Val Ser Ser
                115

<210> SEQ ID NO 91
<211> LENGTH: 119
<212> TYPE: PRT
<213> ORGANISM: Artificial
<220> FEATURE:
<223> OTHER INFORMATION: Synthetic construct

<400> SEQUENCE: 91

Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Ser Phe Thr Asp Tyr
                 20                  25                  30
Asn Met Asn Trp Val Arg Gln Ala Pro Gly Gln Gly Leu Glu Trp Met
             35                  40                  45
Gly Val Ile Asn Pro Asn Tyr Gly Thr Thr Asp Tyr Asn Gln Arg Phe
         50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
```

-continued

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 92
<211> LENGTH: 119
<212> TYPE: PRT
<213> ORGANISM: Artificial
<220> FEATURE:
<223> OTHER INFORMATION: Synthetic construct

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 93
<211> LENGTH: 119
<212> TYPE: PRT
<213> ORGANISM: Artificial
<220> FEATURE:
<223> OTHER INFORMATION: Synthetic construct

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

Asn Met Asn Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Pro Ala Thr Gly Thr Gly Ala Tyr Trp Gly Gln Gly
            100                 105                 110

Thr Leu Val Thr Val Ser Ser
        115

<210> SEQ ID NO 94
<211> LENGTH: 119
<212> TYPE: PRT
<213> ORGANISM: Artificial

```
<220> FEATURE:
<223> OTHER INFORMATION: Synthetic construct

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Leu Gly Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 95
<211> LENGTH: 119
<212> TYPE: PRT
<213> ORGANISM: Artificial
<220> FEATURE:
<223> OTHER INFORMATION: Synthetic construct

<400> SEQUENCE: 95

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile His Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Artificial
<220> FEATURE:
<223> OTHER INFORMATION: Synthetic construct

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30
```

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr His Thr Gly Thr Gly Val Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial
<220> FEATURE:
<223> OTHER INFORMATION: Synthetic construct

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr His Thr Gly Thr Gly Ala Tyr Trp Gly Gln Gly
            100                 105                 110

Thr Leu Val Thr Val Ser Ser
        115

<210> SEQ ID NO 98
<211> LENGTH: 119
<212> TYPE: PRT
<213> ORGANISM: Artificial
<220> FEATURE:
<223> OTHER INFORMATION: Synthetic construct

<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Tyr Asp Tyr Tyr Thr Gly Thr Gly Ala Tyr Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Artificial
<220> FEATURE:
<223> OTHER INFORMATION: Synthetic construct

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Met Ser Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial
<220> FEATURE:
<223> OTHER INFORMATION: Synthetic construct

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 101
<211> LENGTH: 119
<212> TYPE: PRT
```

<213> ORGANISM: Artificial
<220> FEATURE:
<223> OTHER INFORMATION: Synthetic construct

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Met Ser Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr His Thr Gly Thr Gly Ala Tyr Trp Gly Gln Gly
            100                 105                 110

Thr Leu Val Thr Val Ser Ser
        115

<210> SEQ ID NO 102
<211> LENGTH: 119
<212> TYPE: PRT
<213> ORGANISM: Artificial
<220> FEATURE:
<223> OTHER INFORMATION: Synthetic construct

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Artificial
<220> FEATURE:
<223> OTHER INFORMATION: Synthetic construct

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
                35                  40                  45

Gly Val Ile Asn Pro Glu Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Ala Thr Gly Thr Gly Ala Tyr Trp Gly Gln Gly
                100                 105                 110

Thr Leu Val Thr Val Ser Ser
        115

<210> SEQ ID NO 104
<211> LENGTH: 119
<212> TYPE: PRT
<213> ORGANISM: Artificial
<220> FEATURE:
<223> OTHER INFORMATION: Synthetic construct

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile His Trp Val Arg Gln Ala Pro Gly Gln Gly Leu Glu Trp Met
                35                  40                  45

Gly Val Ile Asn Pro Glu Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
                100                 105                 110

Thr Leu Val Thr Val Ser Ser
        115

<210> SEQ ID NO 105
<211> LENGTH: 119
<212> TYPE: PRT
<213> ORGANISM: Artificial
<220> FEATURE:
<223> OTHER INFORMATION: Synthetic construct

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile His Trp Val Arg Gln Ala Pro Gly Gln Gly Leu Glu Trp Met
                35                  40                  45

Gly Val Ile Asn Pro Glu Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys

-continued

```
                     85                  90                  95

Ala Arg Tyr Asp Tyr Tyr Thr Gly Thr Gly Ala Tyr Trp Gly Gln Gly
                100                 105                 110

Thr Leu Val Thr Val Ser Ser
            115

<210> SEQ ID NO 106
<211> LENGTH: 119
<212> TYPE: PRT
<213> ORGANISM: Artificial
<220> FEATURE:
<223> OTHER INFORMATION: Synthetic construct

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile His Trp Val Arg Gln Ala Pro Gly Gln Gly Leu Glu Trp Met
            35                  40                  45

Gly Val Ile Asn Pro Asn Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Ala Tyr Trp Gly Gln Gly
                100                 105                 110

Thr Leu Val Thr Val Ser Ser
            115

<210> SEQ ID NO 107
<211> LENGTH: 119
<212> TYPE: PRT
<213> ORGANISM: Artificial
<220> FEATURE:
<223> OTHER INFORMATION: Synthetic construct

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Leu Gly Trp Val Arg Gln Ala Pro Gly Gln Gly Leu Glu Trp Met
            35                  40                  45

Gly Val Ile Asn Pro Glu Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr His Thr Gly Thr Gly Ala Tyr Trp Gly Gln Gly
                100                 105                 110

Thr Leu Val Thr Val Ser Ser
            115

<210> SEQ ID NO 108
<211> LENGTH: 119
```

```
<212> TYPE: PRT
<213> ORGANISM: Artificial
<220> FEATURE:
<223> OTHER INFORMATION: Synthetic construct

<400> SEQUENCE: 108

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Ala Tyr Trp Gly Gln Gly
            100                 105                 110

Thr Leu Val Thr Val Ser Ser
        115

<210> SEQ ID NO 109
<211> LENGTH: 119
<212> TYPE: PRT
<213> ORGANISM: Artificial
<220> FEATURE:
<223> OTHER INFORMATION: Synthetic construct

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Met Ser Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Artificial
<220> FEATURE:
<223> OTHER INFORMATION: Synthetic construct

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
```

```
                    20                  25                  30
His Met Ser Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
50                      55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Ala Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Artificial
<220> FEATURE:
<223> OTHER INFORMATION: Synthetic construct

<400> SEQUENCE: 111

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile Ser Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
50                      55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 112
<211> LENGTH: 119
<212> TYPE: PRT
<213> ORGANISM: Artificial
<220> FEATURE:
<223> OTHER INFORMATION: Synthetic construct

<400> SEQUENCE: 112

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile Ser Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
50                      55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Artificial
<220> FEATURE:
<223> OTHER INFORMATION: Synthetic construct

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile Ser Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Ala Tyr Trp Gly Gln Gly
            100                 105                 110

Thr Leu Val Thr Val Ser Ser
        115

<210> SEQ ID NO 114
<211> LENGTH: 119
<212> TYPE: PRT
<213> ORGANISM: Artificial
<220> FEATURE:
<223> OTHER INFORMATION: Synthetic construct

<400> SEQUENCE: 114

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 115
```

```
<211> LENGTH: 119
<212> TYPE: PRT
<213> ORGANISM: Artificial
<220> FEATURE:
<223> OTHER INFORMATION: Synthetic construct

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Asn Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 116
<211> LENGTH: 119
<212> TYPE: PRT
<213> ORGANISM: Artificial
<220> FEATURE:
<223> OTHER INFORMATION: Synthetic construct

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Val Tyr Trp Gly Gln Gly
            100                 105                 110

Thr Leu Val Thr Val Ser Ser
        115

<210> SEQ ID NO 117
<211> LENGTH: 119
<212> TYPE: PRT
<213> ORGANISM: Artificial
<220> FEATURE:
<223> OTHER INFORMATION: Synthetic construct

<400> SEQUENCE: 117

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Glu Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115
```

<210> SEQ ID NO 118
<211> LENGTH: 119
<212> TYPE: PRT
<213> ORGANISM: Artificial
<220> FEATURE:
<223> OTHER INFORMATION: Synthetic construct

<400> SEQUENCE: 118

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115
```

<210> SEQ ID NO 119
<211> LENGTH: 119
<212> TYPE: PRT
<213> ORGANISM: Artificial
<220> FEATURE:
<223> OTHER INFORMATION: Synthetic construct

<400> SEQUENCE: 119

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Met Ser Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Tyr Asp Tyr Tyr Thr Gly Thr Gly Ala Tyr Trp Gly Gln Gly
            100                 105                 110

Thr Leu Val Thr Val Ser Ser
        115

<210> SEQ ID NO 120
<211> LENGTH: 119
<212> TYPE: PRT
<213> ORGANISM: Artificial
<220> FEATURE:
<223> OTHER INFORMATION: Synthetic construct

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 121
<211> LENGTH: 119
<212> TYPE: PRT
<213> ORGANISM: Artificial
<220> FEATURE:
<223> OTHER INFORMATION: Synthetic construct

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Met Ser Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115
```

```
<210> SEQ ID NO 122
<211> LENGTH: 16
<212> TYPE: PRT
<213> ORGANISM: Artificial
<220> FEATURE:
<223> OTHER INFORMATION: Synthetic construct

<400> SEQUENCE: 122

Arg Ser Ser Gln Ser Leu Val His Ser Arg Gly Asn Thr Tyr Leu His
1               5                   10                  15

<210> SEQ ID NO 123
<211> LENGTH: 16
<212> TYPE: PRT
<213> ORGANISM: Artificial
<220> FEATURE:
<223> OTHER INFORMATION: Synthetic construct

<400> SEQUENCE: 123

Arg Ser Ser Gln Ser Leu Val His Ser His Gly Asn Thr Tyr Leu His
1               5                   10                  15

<210> SEQ ID NO 124
<211> LENGTH: 16
<212> TYPE: PRT
<213> ORGANISM: Artificial
<220> FEATURE:
<223> OTHER INFORMATION: Synthetic construct

<400> SEQUENCE: 124

Arg Ser Ser Gln Ser Leu Val His Ser Asn Gly Asn Thr Tyr Leu His
1               5                   10                  15

<210> SEQ ID NO 125
<211> LENGTH: 16
<212> TYPE: PRT
<213> ORGANISM: Artificial
<220> FEATURE:
<223> OTHER INFORMATION: Synthetic construct

<400> SEQUENCE: 125

Arg Ser Ser Gln Ser Leu Val His Ser Tyr Gly Asn Thr Tyr Leu His
1               5                   10                  15

<210> SEQ ID NO 126
<211> LENGTH: 16
<212> TYPE: PRT
<213> ORGANISM: Artificial
<220> FEATURE:
<223> OTHER INFORMATION: Synthetic construct

<400> SEQUENCE: 126

Arg Ser Ser Gln Ser Val Val His Ser Arg Gly Asn Thr Tyr Leu His
1               5                   10                  15

<210> SEQ ID NO 127
<211> LENGTH: 16
<212> TYPE: PRT
<213> ORGANISM: Artificial
<220> FEATURE:
<223> OTHER INFORMATION: Synthetic construct

<400> SEQUENCE: 127

Val Ser Ser Gln Ser Leu Val His Ser Arg Gly Asn Thr Tyr Leu His
1               5                   10                  15

<210> SEQ ID NO 128
```

```
<211> LENGTH: 16
<212> TYPE: PRT
<213> ORGANISM: Artificial
<220> FEATURE:
<223> OTHER INFORMATION: Synthetic construct

<400> SEQUENCE: 128

Arg Ser Ser Ala Ser Leu Val His Ser Arg Gly Asn Thr Tyr Leu His
1               5                   10                  15

<210> SEQ ID NO 129
<211> LENGTH: 16
<212> TYPE: PRT
<213> ORGANISM: Artificial
<220> FEATURE:
<223> OTHER INFORMATION: Synthetic construct

<400> SEQUENCE: 129

Arg Ser Ser Gln Ser Leu Lys His Ser Arg Gly Asn Thr Tyr Leu His
1               5                   10                  15

<210> SEQ ID NO 130
<211> LENGTH: 16
<212> TYPE: PRT
<213> ORGANISM: Artificial
<220> FEATURE:
<223> OTHER INFORMATION: Synthetic construct

<400> SEQUENCE: 130

Arg Ser Ser Gln Ser Leu Arg His Ser Arg Gly Asn Thr Tyr Leu His
1               5                   10                  15

<210> SEQ ID NO 131
<211> LENGTH: 16
<212> TYPE: PRT
<213> ORGANISM: Artificial
<220> FEATURE:
<223> OTHER INFORMATION: Synthetic construct

<400> SEQUENCE: 131

Arg Ser Ser Arg Ser Leu Val His Ser Arg Gly Asn Thr Tyr Leu His
1               5                   10                  15

<210> SEQ ID NO 132
<211> LENGTH: 16
<212> TYPE: PRT
<213> ORGANISM: Artificial
<220> FEATURE:
<223> OTHER INFORMATION: Synthetic construct

<400> SEQUENCE: 132

Arg Ser His Gln Ser Leu Val His Ser Arg Gly Asn Thr Tyr Leu His
1               5                   10                  15

<210> SEQ ID NO 133
<211> LENGTH: 16
<212> TYPE: PRT
<213> ORGANISM: Artificial
<220> FEATURE:
<223> OTHER INFORMATION: Synthetic construct

<400> SEQUENCE: 133

Arg Ser Ser Gln Ser Leu Val His Ser Arg Gly Asn Thr Phe Leu His
1               5                   10                  15

<210> SEQ ID NO 134
<211> LENGTH: 16
```

```
<212> TYPE: PRT
<213> ORGANISM: Artificial
<220> FEATURE:
<223> OTHER INFORMATION: Synthetic construct

<400> SEQUENCE: 134

Arg Ser Ser Gln Ser Leu Val His Asn Arg Gly Asn Thr Tyr Leu His
1               5                   10                  15

<210> SEQ ID NO 135
<211> LENGTH: 16
<212> TYPE: PRT
<213> ORGANISM: Artificial
<220> FEATURE:
<223> OTHER INFORMATION: Synthetic construct

<400> SEQUENCE: 135

Arg Ser Ser Gln Ser Leu Val His Ser Arg Gly Arg Thr Tyr Leu His
1               5                   10                  15

<210> SEQ ID NO 136
<211> LENGTH: 16
<212> TYPE: PRT
<213> ORGANISM: Artificial
<220> FEATURE:
<223> OTHER INFORMATION: Synthetic construct

<400> SEQUENCE: 136

Arg Ser Ser Gln Ser Leu Val His Arg Arg Gly Asn Thr Tyr Leu His
1               5                   10                  15

<210> SEQ ID NO 137
<211> LENGTH: 16
<212> TYPE: PRT
<213> ORGANISM: Artificial
<220> FEATURE:
<223> OTHER INFORMATION: Synthetic construct

<400> SEQUENCE: 137

Arg Ser Ser Gln Ser Leu Val His Ser Arg Gly Asn Thr Tyr Thr His
1               5                   10                  15

<210> SEQ ID NO 138
<211> LENGTH: 16
<212> TYPE: PRT
<213> ORGANISM: Artificial
<220> FEATURE:
<223> OTHER INFORMATION: Synthetic construct

<400> SEQUENCE: 138

Arg Ser Ser Gln Ser Leu Val His Ser Arg Gly Asn Thr Tyr Ser His
1               5                   10                  15

<210> SEQ ID NO 139
<211> LENGTH: 16
<212> TYPE: PRT
<213> ORGANISM: Artificial
<220> FEATURE:
<223> OTHER INFORMATION: Synthetic construct

<400> SEQUENCE: 139

Arg Ser Ser Gln Ser Leu Val His Ser Arg Gly Asn Thr Tyr His His
1               5                   10                  15

<210> SEQ ID NO 140
<211> LENGTH: 16
<212> TYPE: PRT
```

```
<213> ORGANISM: Artificial
<220> FEATURE:
<223> OTHER INFORMATION: Synthetic construct

<400> SEQUENCE: 140

Arg Ser Ser Gln Ser Leu Val His Ala Arg Gly Asn Thr Tyr Leu His
1               5                   10                  15

<210> SEQ ID NO 141
<211> LENGTH: 16
<212> TYPE: PRT
<213> ORGANISM: Artificial
<220> FEATURE:
<223> OTHER INFORMATION: Synthetic construct

<400> SEQUENCE: 141

Arg Ser Ser Gln Ser Leu Val His Ser Arg Gly Asn Thr Trp Leu His
1               5                   10                  15

<210> SEQ ID NO 142
<211> LENGTH: 16
<212> TYPE: PRT
<213> ORGANISM: Artificial
<220> FEATURE:
<223> OTHER INFORMATION: Synthetic construct

<400> SEQUENCE: 142

Arg Ser Ser Gln Ser Leu Val His Ser Arg Gly Asn Val Tyr Leu His
1               5                   10                  15

<210> SEQ ID NO 143
<211> LENGTH: 16
<212> TYPE: PRT
<213> ORGANISM: Artificial
<220> FEATURE:
<223> OTHER INFORMATION: Synthetic construct

<400> SEQUENCE: 143

Arg Ser Ser Gln Ser Leu Val His Ser Arg Gly Lys Thr Tyr Leu His
1               5                   10                  15

<210> SEQ ID NO 144
<211> LENGTH: 16
<212> TYPE: PRT
<213> ORGANISM: Artificial
<220> FEATURE:
<223> OTHER INFORMATION: Synthetic construct

<400> SEQUENCE: 144

Arg Ser Ser Gln Ser Leu Val His Leu Arg Gly Asn Thr Tyr Leu His
1               5                   10                  15

<210> SEQ ID NO 145
<211> LENGTH: 16
<212> TYPE: PRT
<213> ORGANISM: Artificial
<220> FEATURE:
<223> OTHER INFORMATION: Synthetic construct

<400> SEQUENCE: 145

Arg Ser Ser Lys Ser Leu Val His Ser Arg Gly Asn Thr Phe Leu His
1               5                   10                  15

<210> SEQ ID NO 146
<211> LENGTH: 16
<212> TYPE: PRT
<213> ORGANISM: Artificial
```

```
<220> FEATURE:
<223> OTHER INFORMATION: Synthetic construct

<400> SEQUENCE: 146

Arg Ser Ser Gln Ser Leu Arg His Ser Arg Gly Asn Thr Phe Leu His
1               5                   10                  15

<210> SEQ ID NO 147
<211> LENGTH: 16
<212> TYPE: PRT
<213> ORGANISM: Artificial
<220> FEATURE:
<223> OTHER INFORMATION: Synthetic construct

<400> SEQUENCE: 147

Arg Ser Ser Gln Ser Leu Lys His Ser Arg Gly Asn Thr Phe Leu His
1               5                   10                  15

<210> SEQ ID NO 148
<211> LENGTH: 16
<212> TYPE: PRT
<213> ORGANISM: Artificial
<220> FEATURE:
<223> OTHER INFORMATION: Synthetic construct

<400> SEQUENCE: 148

Arg Ser Ser Arg Ser Leu Val His Ser Arg Gly Asn Thr Phe Leu His
1               5                   10                  15

<210> SEQ ID NO 149
<211> LENGTH: 16
<212> TYPE: PRT
<213> ORGANISM: Artificial
<220> FEATURE:
<223> OTHER INFORMATION: Synthetic construct

<400> SEQUENCE: 149

Arg Ser Ser Gln Ser Leu Lys His Ser His Gly Asn Thr Tyr Leu His
1               5                   10                  15

<210> SEQ ID NO 150
<211> LENGTH: 7
<212> TYPE: PRT
<213> ORGANISM: Artificial
<220> FEATURE:
<223> OTHER INFORMATION: Synthetic construct

<400> SEQUENCE: 150

Lys Val Ser Asn Arg Phe Ser
1               5

<210> SEQ ID NO 151
<211> LENGTH: 7
<212> TYPE: PRT
<213> ORGANISM: Artificial
<220> FEATURE:
<223> OTHER INFORMATION: Synthetic construct

<400> SEQUENCE: 151

Ile Val Ser Asn Arg Phe Ser
1               5

<210> SEQ ID NO 152
<211> LENGTH: 7
<212> TYPE: PRT
<213> ORGANISM: Artificial
<220> FEATURE:
```

<223> OTHER INFORMATION: Synthetic construct

<400> SEQUENCE: 152

Lys Val Ser Asn Arg Phe His
1               5

<210> SEQ ID NO 153
<211> LENGTH: 7
<212> TYPE: PRT
<213> ORGANISM: Artificial
<220> FEATURE:
<223> OTHER INFORMATION: Synthetic construct

<400> SEQUENCE: 153

Lys Val Ala Asn Arg Phe Ser
1               5

<210> SEQ ID NO 154
<211> LENGTH: 7
<212> TYPE: PRT
<213> ORGANISM: Artificial
<220> FEATURE:
<223> OTHER INFORMATION: Synthetic construct

<400> SEQUENCE: 154

Lys Val Ser Val Arg Phe Ser
1               5

<210> SEQ ID NO 155
<211> LENGTH: 7
<212> TYPE: PRT
<213> ORGANISM: Artificial
<220> FEATURE:
<223> OTHER INFORMATION: Synthetic construct

<400> SEQUENCE: 155

Lys Val Ser Asn Asn Phe Ser
1               5

<210> SEQ ID NO 156
<211> LENGTH: 7
<212> TYPE: PRT
<213> ORGANISM: Artificial
<220> FEATURE:
<223> OTHER INFORMATION: Synthetic construct

<400> SEQUENCE: 156

Lys Val Asp Asn Arg Phe Ser
1               5

<210> SEQ ID NO 157
<211> LENGTH: 7
<212> TYPE: PRT
<213> ORGANISM: Artificial
<220> FEATURE:
<223> OTHER INFORMATION: Synthetic construct

<400> SEQUENCE: 157

Lys Val Thr Asn Arg Phe Ser
1               5

<210> SEQ ID NO 158
<211> LENGTH: 7
<212> TYPE: PRT
<213> ORGANISM: Artificial
<220> FEATURE:
<223> OTHER INFORMATION: Synthetic construct

```
<400> SEQUENCE: 158

Lys Val Ser Asn Ile Phe Ser
1               5

<210> SEQ ID NO 159
<211> LENGTH: 7
<212> TYPE: PRT
<213> ORGANISM: Artificial
<220> FEATURE:
<223> OTHER INFORMATION: Synthetic construct

<400> SEQUENCE: 159

Lys Val Ser Thr Arg Phe Ser
1               5

<210> SEQ ID NO 160
<211> LENGTH: 7
<212> TYPE: PRT
<213> ORGANISM: Artificial
<220> FEATURE:
<223> OTHER INFORMATION: Synthetic construct

<400> SEQUENCE: 160

Lys Val Arg Asn Arg Phe Ser
1               5

<210> SEQ ID NO 161
<211> LENGTH: 7
<212> TYPE: PRT
<213> ORGANISM: Artificial
<220> FEATURE:
<223> OTHER INFORMATION: Synthetic construct

<400> SEQUENCE: 161

Lys Val Pro Asn Arg Phe Ser
1               5

<210> SEQ ID NO 162
<211> LENGTH: 7
<212> TYPE: PRT
<213> ORGANISM: Artificial
<220> FEATURE:
<223> OTHER INFORMATION: Synthetic construct

<400> SEQUENCE: 162

Lys Val Ser Asn Arg Phe Val
1               5

<210> SEQ ID NO 163
<211> LENGTH: 7
<212> TYPE: PRT
<213> ORGANISM: Artificial
<220> FEATURE:
<223> OTHER INFORMATION: Synthetic construct

<400> SEQUENCE: 163

Lys Val Ser Asn Arg Ile Ser
1               5

<210> SEQ ID NO 164
<211> LENGTH: 7
<212> TYPE: PRT
<213> ORGANISM: Artificial
<220> FEATURE:
<223> OTHER INFORMATION: Synthetic construct
```

```
<400> SEQUENCE: 164

Lys Val Ser Asn Arg Phe Thr
1               5

<210> SEQ ID NO 165
<211> LENGTH: 7
<212> TYPE: PRT
<213> ORGANISM: Artificial
<220> FEATURE:
<223> OTHER INFORMATION: Synthetic construct

<400> SEQUENCE: 165

Lys Val Ser Asn Arg Asn Ser
1               5

<210> SEQ ID NO 166
<211> LENGTH: 7
<212> TYPE: PRT
<213> ORGANISM: Artificial
<220> FEATURE:
<223> OTHER INFORMATION: Synthetic construct

<400> SEQUENCE: 166

Lys Val His Asn Arg Phe Ser
1               5

<210> SEQ ID NO 167
<211> LENGTH: 7
<212> TYPE: PRT
<213> ORGANISM: Artificial
<220> FEATURE:
<223> OTHER INFORMATION: Synthetic construct

<400> SEQUENCE: 167

Lys Val Ser Asn Arg Phe Ile
1               5

<210> SEQ ID NO 168
<211> LENGTH: 9
<212> TYPE: PRT
<213> ORGANISM: Artificial
<220> FEATURE:
<223> OTHER INFORMATION: Synthetic construct

<400> SEQUENCE: 168

Ser Gln Ser Thr His Leu Pro Phe Thr
1               5

<210> SEQ ID NO 169
<211> LENGTH: 9
<212> TYPE: PRT
<213> ORGANISM: Artificial
<220> FEATURE:
<223> OTHER INFORMATION: Synthetic construct

<400> SEQUENCE: 169

Ser Gln Ser Thr His Tyr Pro Phe Thr
1               5

<210> SEQ ID NO 170
<211> LENGTH: 9
<212> TYPE: PRT
<213> ORGANISM: Artificial
<220> FEATURE:
<223> OTHER INFORMATION: Synthetic construct

<400> SEQUENCE: 170
```

Ser Gln Ser Thr His Ile Pro Phe Thr
1               5

<210> SEQ ID NO 171
<211> LENGTH: 9
<212> TYPE: PRT
<213> ORGANISM: Artificial
<220> FEATURE:
<223> OTHER INFORMATION: Synthetic construct

<400> SEQUENCE: 171

Ser Gln Ser Leu His Val Pro Phe Thr
1               5

<210> SEQ ID NO 172
<211> LENGTH: 9
<212> TYPE: PRT
<213> ORGANISM: Artificial
<220> FEATURE:
<223> OTHER INFORMATION: Synthetic construct

<400> SEQUENCE: 172

Ser Gln Ser Thr His Glu Pro Phe Thr
1               5

<210> SEQ ID NO 173
<211> LENGTH: 9
<212> TYPE: PRT
<213> ORGANISM: Artificial
<220> FEATURE:
<223> OTHER INFORMATION: Synthetic construct

<400> SEQUENCE: 173

Asn Gln Ser Thr His Val Pro Phe Thr
1               5

<210> SEQ ID NO 174
<211> LENGTH: 9
<212> TYPE: PRT
<213> ORGANISM: Artificial
<220> FEATURE:
<223> OTHER INFORMATION: Synthetic construct

<400> SEQUENCE: 174

Ser Gln Thr Thr His Val Pro Phe Thr
1               5

<210> SEQ ID NO 175
<211> LENGTH: 9
<212> TYPE: PRT
<213> ORGANISM: Artificial
<220> FEATURE:
<223> OTHER INFORMATION: Synthetic construct

<400> SEQUENCE: 175

Ser Gln Ser Met His Val Pro Phe Thr
1               5

<210> SEQ ID NO 176
<211> LENGTH: 9
<212> TYPE: PRT
<213> ORGANISM: Artificial
<220> FEATURE:
<223> OTHER INFORMATION: Synthetic construct

<400> SEQUENCE: 176

Ser Gln Thr Thr His Leu Pro Phe Thr
1               5

<210> SEQ ID NO 177
<211> LENGTH: 9
<212> TYPE: PRT
<213> ORGANISM: Artificial
<220> FEATURE:
<223> OTHER INFORMATION: Synthetic construct

<400> SEQUENCE: 177

Ser Gln Ser Thr Ser Leu Pro Phe Thr
1               5

<210> SEQ ID NO 178
<211> LENGTH: 112
<212> TYPE: PRT
<213> ORGANISM: Artificial
<220> FEATURE:
<223> OTHER INFORMATION: Synthetic construct

<400> SEQUENCE: 178

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 179
<211> LENGTH: 112
<212> TYPE: PRT
<213> ORGANISM: Artificial
<220> FEATURE:
<223> OTHER INFORMATION: Synthetic construct

<400> SEQUENCE: 179

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

```
<210> SEQ ID NO 180
<211> LENGTH: 112
<212> TYPE: PRT
<213> ORGANISM: Artificial
<220> FEATURE:
<223> OTHER INFORMATION: Synthetic construct

<400> SEQUENCE: 180

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

His Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 181
<211> LENGTH: 112
<212> TYPE: PRT
<213> ORGANISM: Artificial
<220> FEATURE:
<223> OTHER INFORMATION: Synthetic construct

<400> SEQUENCE: 181

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 182
<211> LENGTH: 112
<212> TYPE: PRT
<213> ORGANISM: Artificial
<220> FEATURE:
<223> OTHER INFORMATION: Synthetic construct

<400> SEQUENCE: 182

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 183
<211> LENGTH: 112
<212> TYPE: PRT
<213> ORGANISM: Artificial
<220> FEATURE:
<223> OTHER INFORMATION: Synthetic construct

<400> SEQUENCE: 183

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
             20                  25                  30

Tyr Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 184
<211> LENGTH: 112
<212> TYPE: PRT
<213> ORGANISM: Artificial
<220> FEATURE:
<223> OTHER INFORMATION: Synthetic construct

<400> SEQUENCE: 184

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 185
<211> LENGTH: 112
<212> TYPE: PRT
```

```
<213> ORGANISM: Artificial
<220> FEATURE:
<223> OTHER INFORMATION: Synthetic construct

<400> SEQUENCE: 185

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 186
<211> LENGTH: 112
<212> TYPE: PRT
<213> ORGANISM: Artificial
<220> FEATURE:
<223> OTHER INFORMATION: Synthetic construct

<400> SEQUENCE: 186

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 187
<211> LENGTH: 112
<212> TYPE: PRT
<213> ORGANISM: Artificial
<220> FEATURE:
<223> OTHER INFORMATION: Synthetic construct

<400> SEQUENCE: 187

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

His Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 188
<211> LENGTH: 112
<212> TYPE: PRT
<213> ORGANISM: Artificial
<220> FEATURE:
<223> OTHER INFORMATION: Synthetic construct

<400> SEQUENCE: 188

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
                20                  25                  30

His Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 189
<211> LENGTH: 112
<212> TYPE: PRT
<213> ORGANISM: Artificial
<220> FEATURE:
<223> OTHER INFORMATION: Synthetic construct

<400> SEQUENCE: 189

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 190
<211> LENGTH: 112
<212> TYPE: PRT
<213> ORGANISM: Artificial
<220> FEATURE:
<223> OTHER INFORMATION: Synthetic construct
```

```
<400> SEQUENCE: 190

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 191
<211> LENGTH: 112
<212> TYPE: PRT
<213> ORGANISM: Artificial
<220> FEATURE:
<223> OTHER INFORMATION: Synthetic construct

<400> SEQUENCE: 191

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 192
<211> LENGTH: 112
<212> TYPE: PRT
<213> ORGANISM: Artificial
<220> FEATURE:
<223> OTHER INFORMATION: Synthetic construct

<400> SEQUENCE: 192

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 193
<211> LENGTH: 112
<212> TYPE: PRT
<213> ORGANISM: Artificial
<220> FEATURE:
<223> OTHER INFORMATION: Synthetic construct

<400> SEQUENCE: 193

Asp Ile Val Met Thr Gln Thr Pro Leu Ser Leu Ser Val Thr Pro Gly
1               5                   10                  15

Gln Pro Ala Ser Ile Ser Cys Val Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 194
<211> LENGTH: 112
<212> TYPE: PRT
<213> ORGANISM: Artificial
<220> FEATURE:
<223> OTHER INFORMATION: Synthetic construct

<400> SEQUENCE: 194

Asp Ile Val Met Thr Gln Thr Pro Leu Ser Leu Ser Val Thr Pro Gly
1               5                   10                  15

Gln Pro Ala Ser Ile Ser Cys Arg Ser Ser Ala Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 195
<211> LENGTH: 112
<212> TYPE: PRT
<213> ORGANISM: Artificial
<220> FEATURE:
<223> OTHER INFORMATION: Synthetic construct

<400> SEQUENCE: 195

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110
```

<210> SEQ ID NO 196
<211> LENGTH: 112
<212> TYPE: PRT
<213> ORGANISM: Artificial
<220> FEATURE:
<223> OTHER INFORMATION: Synthetic construct

<400> SEQUENCE: 196

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Arg His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110
```

<210> SEQ ID NO 197
<211> LENGTH: 112
<212> TYPE: PRT
<213> ORGANISM: Artificial
<220> FEATURE:
<223> OTHER INFORMATION: Synthetic construct

<400> SEQUENCE: 197

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
                85                  90                  95
```

Thr His Tyr Pro Phe Thr Phe Gly Gln Gly Thr Lys Leu Glu Ile Lys
            100                 105                 110

<210> SEQ ID NO 198
<211> LENGTH: 112
<212> TYPE: PRT
<213> ORGANISM: Artificial
<220> FEATURE:
<223> OTHER INFORMATION: Synthetic construct

<400> SEQUENCE: 198

Asp Ile Val Met Thr Gln Thr Pro Leu Ser Leu Ser Val Thr Pro Gly
1               5                   10                  15

Gln Pro Ala Ser Ile Ser Cys Arg Ser His Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 199
<211> LENGTH: 112
<212> TYPE: PRT
<213> ORGANISM: Artificial
<220> FEATURE:
<223> OTHER INFORMATION: Synthetic construct

<400> SEQUENCE: 199

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Phe Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 200
<211> LENGTH: 112
<212> TYPE: PRT
<213> ORGANISM: Artificial
<220> FEATURE:
<223> OTHER INFORMATION: Synthetic construct

<400> SEQUENCE: 200

Asp Ile Val Met Thr Gln Thr Pro Leu Ser Leu Ser Val Thr Pro Gly
1               5                   10                  15

-continued

```
Gln Pro Ala Ser Ile Ser Cys Arg Ser Ser Gln Ser Leu Val His Asn
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
                100                 105                 110

<210> SEQ ID NO 201
<211> LENGTH: 112
<212> TYPE: PRT
<213> ORGANISM: Artificial
<220> FEATURE:
<223> OTHER INFORMATION: Synthetic construct

<400> SEQUENCE: 201

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Arg Gly Arg Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
                100                 105                 110

<210> SEQ ID NO 202
<211> LENGTH: 112
<212> TYPE: PRT
<213> ORGANISM: Artificial
<220> FEATURE:
<223> OTHER INFORMATION: Synthetic construct

<400> SEQUENCE: 202

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Arg
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
                100                 105                 110
```

<210> SEQ ID NO 203
<211> LENGTH: 112
<212> TYPE: PRT
<213> ORGANISM: Artificial
<220> FEATURE:
<223> OTHER INFORMATION: Synthetic construct

<400> SEQUENCE: 203

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Thr His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 204
<211> LENGTH: 112
<212> TYPE: PRT
<213> ORGANISM: Artificial
<220> FEATURE:
<223> OTHER INFORMATION: Synthetic construct

<400> SEQUENCE: 204

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Ser His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 205
<211> LENGTH: 112
<212> TYPE: PRT
<213> ORGANISM: Artificial
<220> FEATURE:
<223> OTHER INFORMATION: Synthetic construct

<400> SEQUENCE: 205

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

```
Arg Gly Asn Thr Tyr His His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 206
<211> LENGTH: 112
<212> TYPE: PRT
<213> ORGANISM: Artificial
<220> FEATURE:
<223> OTHER INFORMATION: Synthetic construct

<400> SEQUENCE: 206

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ala
            20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 207
<211> LENGTH: 112
<212> TYPE: PRT
<213> ORGANISM: Artificial
<220> FEATURE:
<223> OTHER INFORMATION: Synthetic construct

<400> SEQUENCE: 207

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Trp Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 208
```

```
<211> LENGTH: 112
<212> TYPE: PRT
<213> ORGANISM: Artificial
<220> FEATURE:
<223> OTHER INFORMATION: Synthetic construct

<400> SEQUENCE: 208

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Val Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 209
<211> LENGTH: 112
<212> TYPE: PRT
<213> ORGANISM: Artificial
<220> FEATURE:
<223> OTHER INFORMATION: Synthetic construct

<400> SEQUENCE: 209

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 210
<211> LENGTH: 112
<212> TYPE: PRT
<213> ORGANISM: Artificial
<220> FEATURE:
<223> OTHER INFORMATION: Synthetic construct

<400> SEQUENCE: 210

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Leu
            20                  25                  30

Arg Gly Asn Thr Tyr Leu His Trp Tyr Leu Gln Lys Pro Gly Gln Ser
        35                  40                  45
```

-continued

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 211
<211> LENGTH: 112
<212> TYPE: PRT
<213> ORGANISM: Artificial
<220> FEATURE:
<223> OTHER INFORMATION: Synthetic construct

<400> SEQUENCE: 211

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Ile Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 212
<211> LENGTH: 112
<212> TYPE: PRT
<213> ORGANISM: Artificial
<220> FEATURE:
<223> OTHER INFORMATION: Synthetic construct

<400> SEQUENCE: 212

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 213
<211> LENGTH: 112
<212> TYPE: PRT
<213> ORGANISM: Artificial

```
<220> FEATURE:
<223> OTHER INFORMATION: Synthetic construct

<400> SEQUENCE: 213

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 214
<211> LENGTH: 112
<212> TYPE: PRT
<213> ORGANISM: Artificial
<220> FEATURE:
<223> OTHER INFORMATION: Synthetic construct

<400> SEQUENCE: 214

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 215
<211> LENGTH: 112
<212> TYPE: PRT
<213> ORGANISM: Artificial
<220> FEATURE:
<223> OTHER INFORMATION: Synthetic construct

<400> SEQUENCE: 215

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Arg His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110
```

<210> SEQ ID NO 216
<211> LENGTH: 112
<212> TYPE: PRT
<213> ORGANISM: Artificial
<220> FEATURE:
<223> OTHER INFORMATION: Synthetic construct

<400> SEQUENCE: 216

```
Asp Ile Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Lys His Ser
             20                  25                  30

Arg Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110
```

<210> SEQ ID NO 217
<211> LENGTH: 112
<212> TYPE: PRT
<213> ORGANISM: Artificial
<220> FEATURE:
<223> OTHER INFORMATION: Synthetic construct

<400> SEQUENCE: 217

```
Asp Ile Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Arg His Ser
             20                  25                  30

Arg Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe His Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110
```

<210> SEQ ID NO 218
<211> LENGTH: 112
<212> TYPE: PRT
<213> ORGANISM: Artificial
<220> FEATURE:
<223> OTHER INFORMATION: Synthetic construct

<400> SEQUENCE: 218

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ala Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 219
<211> LENGTH: 112
<212> TYPE: PRT
<213> ORGANISM: Artificial
<220> FEATURE:
<223> OTHER INFORMATION: Synthetic construct

<400> SEQUENCE: 219

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Phe Leu His Trp Tyr Leu Gln Lys Pro Gly Gln Ser
        35                  40                  45

Pro Gln Leu Leu Ile Tyr Lys Val Ser Val Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 220
<211> LENGTH: 112
<212> TYPE: PRT
<213> ORGANISM: Artificial
<220> FEATURE:
<223> OTHER INFORMATION: Synthetic construct

<400> SEQUENCE: 220

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Asn Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 221
<211> LENGTH: 112
<212> TYPE: PRT
<213> ORGANISM: Artificial
<220> FEATURE:
<223> OTHER INFORMATION: Synthetic construct

<400> SEQUENCE: 221

Asp Ile Val Met Thr Gln Thr Pro Leu Ser Leu Ser Val Thr Pro Gly
1               5                   10                  15

Gln Pro Ala Ser Ile Ser Cys Arg Ser Gln Ser Leu Val His Ser
            20                  25                  30

Arg Gly Asn Thr Phe Leu His Trp Tyr Leu Gln Lys Pro Gly Gln Ser
            35                  40                  45

Pro Gln Leu Leu Ile Tyr Lys Val Asp Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 222
<211> LENGTH: 112
<212> TYPE: PRT
<213> ORGANISM: Artificial
<220> FEATURE:
<223> OTHER INFORMATION: Synthetic construct

<400> SEQUENCE: 222

Asp Ile Val Met Thr Gln Thr Pro Leu Ser Leu Ser Val Thr Pro Gly
1               5                   10                  15

Gln Pro Ala Ser Ile Ser Cys Arg Ser Arg Ser Leu Val His Ser
            20                  25                  30

Arg Gly Asn Thr Phe Leu His Trp Tyr Leu Gln Lys Pro Gly Gln Ser
            35                  40                  45

Pro Gln Leu Leu Ile Tyr Lys Val Thr Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Tyr Pro Phe Thr Phe Gly Gln Gly Thr Lys Leu Glu Ile Lys
            100                 105                 110

<210> SEQ ID NO 223
<211> LENGTH: 112
<212> TYPE: PRT
<213> ORGANISM: Artificial
<220> FEATURE:
<223> OTHER INFORMATION: Synthetic construct

<400> SEQUENCE: 223

Asp Ile Val Met Thr Gln Thr Pro Leu Ser Leu Ser Val Thr Pro Gly
```

```
                1               5                   10                  15
Gln Pro Ala Ser Ile Ser Cys Arg Ser Ser Gln Ser Leu Arg His Ser
                20                  25                  30

Arg Gly Asn Thr Tyr Leu His Trp Tyr Leu Gln Lys Pro Gly Gln Ser
                35                  40                  45

Pro Gln Leu Leu Ile Tyr Lys Val Ser Asn Ile Phe Ser Gly Val Pro
                50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
                100                 105                 110

<210> SEQ ID NO 224
<211> LENGTH: 112
<212> TYPE: PRT
<213> ORGANISM: Artificial
<220> FEATURE:
<223> OTHER INFORMATION: Synthetic construct

<400> SEQUENCE: 224

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
                20                  25                  30

Arg Gly Asn Thr Phe Leu His Trp Tyr Leu Gln Lys Pro Gly Gln Ser
                35                  40                  45

Pro Gln Leu Leu Ile Tyr Lys Val Ser Thr Arg Phe Ser Gly Val Pro
                50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
                100                 105                 110

<210> SEQ ID NO 225
<211> LENGTH: 112
<212> TYPE: PRT
<213> ORGANISM: Artificial
<220> FEATURE:
<223> OTHER INFORMATION: Synthetic construct

<400> SEQUENCE: 225

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Arg His Ser
                20                  25                  30

Arg Gly Asn Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
                50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95
```

```
Thr His Tyr Pro Phe Thr Phe Gly Gln Gly Thr Lys Leu Glu Ile Lys
            100                 105                 110
```

<210> SEQ ID NO 226
<211> LENGTH: 112
<212> TYPE: PRT
<213> ORGANISM: Artificial
<220> FEATURE:
<223> OTHER INFORMATION: Synthetic construct

<400> SEQUENCE: 226

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Phe Leu His Trp Tyr Leu Gln Lys Pro Gly Gln Ser
        35                  40                  45

Pro Gln Leu Leu Ile Tyr Lys Val Arg Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110
```

<210> SEQ ID NO 227
<211> LENGTH: 112
<212> TYPE: PRT
<213> ORGANISM: Artificial
<220> FEATURE:
<223> OTHER INFORMATION: Synthetic construct

<400> SEQUENCE: 227

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Arg His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Pro Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110
```

<210> SEQ ID NO 228
<211> LENGTH: 112
<212> TYPE: PRT
<213> ORGANISM: Artificial
<220> FEATURE:
<223> OTHER INFORMATION: Synthetic construct

<400> SEQUENCE: 228

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30
```

```
                    20                  25                  30

Arg Gly Asn Thr Phe Leu His Trp Tyr Leu Gln Lys Pro Gly Gln Ser
            35                  40                  45

Pro Gln Leu Leu Ile Tyr Lys Val Ser Asn Arg Phe Val Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 229
<211> LENGTH: 112
<212> TYPE: PRT
<213> ORGANISM: Artificial
<220> FEATURE:
<223> OTHER INFORMATION: Synthetic construct

<400> SEQUENCE: 229

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Arg His Ser
            20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Ile Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110

<210> SEQ ID NO 230
<211> LENGTH: 112
<212> TYPE: PRT
<213> ORGANISM: Artificial
<220> FEATURE:
<223> OTHER INFORMATION: Synthetic construct

<400> SEQUENCE: 230

Asp Ile Val Met Thr Gln Thr Pro Leu Ser Leu Ser Val Thr Pro Gly
 1               5                  10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Thr Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
            100                 105                 110
```

<210> SEQ ID NO 231
<211> LENGTH: 112
<212> TYPE: PRT
<213> ORGANISM: Artificial
<220> FEATURE:
<223> OTHER INFORMATION: Synthetic construct

<400> SEQUENCE: 231

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Arg His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Asn Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 232
<211> LENGTH: 112
<212> TYPE: PRT
<213> ORGANISM: Artificial
<220> FEATURE:
<223> OTHER INFORMATION: Synthetic construct

<400> SEQUENCE: 232

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val His Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 233
<211> LENGTH: 112
<212> TYPE: PRT
<213> ORGANISM: Artificial
<220> FEATURE:
<223> OTHER INFORMATION: Synthetic construct

<400> SEQUENCE: 233

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Tyr Leu His Trp Tyr Leu Gln Lys Pro Gly Gln Ser

```
                35                  40                  45
Pro Gln Leu Leu Ile Tyr Lys Val Ser Thr Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
                100                 105                 110

<210> SEQ ID NO 234
<211> LENGTH: 112
<212> TYPE: PRT
<213> ORGANISM: Artificial
<220> FEATURE:
<223> OTHER INFORMATION: Synthetic construct

<400> SEQUENCE: 234

Asp Ile Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Val His Ser
                 20                  25                  30

Arg Gly Asn Thr Phe Leu His Trp Tyr Leu Gln Lys Pro Gly Gln Ser
                35                  40                  45

Pro Gln Leu Leu Ile Tyr Lys Val Ser Asn Arg Phe Ile Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
                100                 105                 110

<210> SEQ ID NO 235
<211> LENGTH: 112
<212> TYPE: PRT
<213> ORGANISM: Artificial
<220> FEATURE:
<223> OTHER INFORMATION: Synthetic construct

<400> SEQUENCE: 235

Asp Ile Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Lys His Ser
                 20                  25                  30

His Gly Asn Thr Tyr Leu His Trp Tyr Leu Gln Lys Pro Gly Gln Ser
                35                  40                  45

Pro Gln Leu Leu Ile Tyr Lys Val Ser Asn Arg Phe Ile Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Tyr Pro Phe Thr Phe Gly Gln Gly Thr Lys Leu Glu Ile Lys
                100                 105                 110

<210> SEQ ID NO 236
<211> LENGTH: 112
```

```
<212> TYPE: PRT
<213> ORGANISM: Artificial
<220> FEATURE:
<223> OTHER INFORMATION: Synthetic construct

<400> SEQUENCE: 236

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 237
<211> LENGTH: 112
<212> TYPE: PRT
<213> ORGANISM: Artificial
<220> FEATURE:
<223> OTHER INFORMATION: Synthetic construct

<400> SEQUENCE: 237

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 238
<211> LENGTH: 112
<212> TYPE: PRT
<213> ORGANISM: Artificial
<220> FEATURE:
<223> OTHER INFORMATION: Synthetic construct

<400> SEQUENCE: 238

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Tyr Pro Phe Thr Phe Gly Gln Gly Thr Lys Leu Glu Ile Lys
                100                 105                 110

<210> SEQ ID NO 239
<211> LENGTH: 112
<212> TYPE: PRT
<213> ORGANISM: Artificial
<220> FEATURE:
<223> OTHER INFORMATION: Synthetic construct

<400> SEQUENCE: 239

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Lys His Ser
                20                  25                  30

Arg Gly Asn Thr Phe Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Tyr Pro Phe Thr Phe Gly Gln Gly Thr Lys Leu Glu Ile Lys
                100                 105                 110

<210> SEQ ID NO 240
<211> LENGTH: 112
<212> TYPE: PRT
<213> ORGANISM: Artificial
<220> FEATURE:
<223> OTHER INFORMATION: Synthetic construct

<400> SEQUENCE: 240

Asp Ile Val Met Thr Gln Thr Pro Leu Ser Leu Ser Val Thr Pro Gly
 1               5                  10                  15

Gln Pro Ala Ser Ile Ser Cys Arg Ser Ser Arg Ser Leu Val His Ser
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Tyr Pro Phe Thr Phe Gly Gln Gly Thr Lys Leu Glu Ile Lys
                100                 105                 110

<210> SEQ ID NO 241
<211> LENGTH: 112
<212> TYPE: PRT
<213> ORGANISM: Artificial
<220> FEATURE:
```

-continued

<223> OTHER INFORMATION: Synthetic construct

<400> SEQUENCE: 241

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 242
<211> LENGTH: 112
<212> TYPE: PRT
<213> ORGANISM: Artificial
<220> FEATURE:
<223> OTHER INFORMATION: Synthetic construct

<400> SEQUENCE: 242

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

<210> SEQ ID NO 243
<211> LENGTH: 112
<212> TYPE: PRT
<213> ORGANISM: Artificial
<220> FEATURE:
<223> OTHER INFORMATION: Synthetic construct

<400> SEQUENCE: 243

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Ser Gln Ser
                    85                  90                  95
Thr His Tyr Pro Phe Thr Phe Gly Gln Gly Thr Lys Leu Glu Ile Lys
                    100                 105                 110
```

```
<210> SEQ ID NO 244
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is G or H
<220> FEATURE:
<221> NAME/KEY: MISC_FEATURE
<222> LOCATION: (3)..(3)
<223> OTHER INFORMATION: X is S, H, or P
<220> FEATURE:
<221> NAME/KEY: MISC_FEATURE
<222> LOCATION: (5)..(5)
<223> OTHER INFORMATION: X is T, G, R, N, or P
<220> FEATURE:
<221> NAME/KEY: MISC_FEATURE
<222> LOCATION: (6)..(6)
<223> OTHER INFORMATION: X is D or W
<220> FEATURE:
<221> NAME/KEY: MISC_FEATURE
<222> LOCATION: (7)..(7)
<223> OTHER INFORMATION: X is Y or F
<220> FEATURE:
<221> NAME/KEY: MISC_FEATURE
<222> LOCATION: (8)..(8)
<223> OTHER INFORMATION: X is N or H
<220> FEATURE:
<221> NAME/KEY: MISC_FEATURE
<222> LOCATION: (9)..(9)
<223> OTHER INFORMATION: X is M, I, L or T
<220> FEATURE:
<221> NAME/KEY: MISC_FEATURE
<222> LOCATION: (10)..(10)
<223> OTHER INFORMATION: X is N, S, G, or H

<400> SEQUENCE: 244

Xaa Tyr Xaa Phe Xaa Xaa Xaa Xaa Xaa Xaa
1               5                   10

<210> SEQ ID NO 245
<211> LENGTH: 16
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X is N, M, A or E

<400> SEQUENCE: 245

Val Ile Asn Pro Xaa Tyr Gly Thr Thr Asp Tyr Asn Gln Arg Phe Lys
1               5                   10                  15

<210> SEQ ID NO 246
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
```

```
<222> LOCATION: (3)..(3)
<223> OTHER INFORMATION: X is  Y or P
<220> FEATURE:
<221> NAME/KEY: MISC_FEATURE
<222> LOCATION: (4)..(4)
<223> OTHER INFORMATION: X is  A, S, F, L. H, Y or W
<220> FEATURE:
<221> NAME/KEY: MISC_FEATURE
<222> LOCATION: (5)..(5)
<223> OTHER INFORMATION: X is  T or P
<220> FEATURE:
<221> NAME/KEY: MISC_FEATURE
<222> LOCATION: (6)..(6)
<223> OTHER INFORMATION: X is G or S
<220> FEATURE:
<221> NAME/KEY: MISC_FEATURE
<222> LOCATION: (9)..(9)
<223> OTHER INFORMATION: X is P, A, V, G, L or T

<400> SEQUENCE: 246

Tyr Asp Xaa Xaa Xaa Xaa Thr Gly Xaa Tyr
1               5                   10

<210> SEQ ID NO 247
<211> LENGTH: 16
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is R or V
<220> FEATURE:
<221> NAME/KEY: MISC_FEATURE
<222> LOCATION: (3)..(3)
<223> OTHER INFORMATION: X is S or H
<220> FEATURE:
<221> NAME/KEY: MISC_FEATURE
<222> LOCATION: (4)..(4)
<223> OTHER INFORMATION: X is Q, K, A or R
<220> FEATURE:
<221> NAME/KEY: MISC_FEATURE
<222> LOCATION: (6)..(6)
<223> OTHER INFORMATION: X is L or V
<220> FEATURE:
<221> NAME/KEY: MISC_FEATURE
<222> LOCATION: (7)..(7)
<223> OTHER INFORMATION: X is V, K or R
<220> FEATURE:
<221> NAME/KEY: MISC_FEATURE
<222> LOCATION: (9)..(9)
<223> OTHER INFORMATION: X is S, N, A, R or L
<220> FEATURE:
<221> NAME/KEY: MISC_FEATURE
<222> LOCATION: (10)..(10)
<223> OTHER INFORMATION: X is R, H, N or Y
<220> FEATURE:
<221> NAME/KEY: MISC_FEATURE
<222> LOCATION: (12)..(12)
<223> OTHER INFORMATION: X is N, R or K
<220> FEATURE:
<221> NAME/KEY: MISC_FEATURE
<222> LOCATION: (13)..(13)
<223> OTHER INFORMATION: X is T or V
<220> FEATURE:
<221> NAME/KEY: MISC_FEATURE
<222> LOCATION: (14)..(14)
<223> OTHER INFORMATION: X is Y, F or W
<220> FEATURE:
<221> NAME/KEY: MISC_FEATURE
<222> LOCATION: (15)..(15)
<223> OTHER INFORMATION: X is L, T, S, H or F

<400> SEQUENCE: 247

Xaa Ser Xaa Xaa Ser Xaa Xaa His Xaa Xaa Gly Xaa Xaa Xaa Xaa His
```

<210> SEQ ID NO 248
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is K or I
<220> FEATURE:
<221> NAME/KEY: MISC_FEATURE
<222> LOCATION: (3)..(3)
<223> OTHER INFORMATION: X is T, D, S, A, R, P or H
<220> FEATURE:
<221> NAME/KEY: MISC_FEATURE
<222> LOCATION: (4)..(4)
<223> OTHER INFORMATION: X is N, V or T
<220> FEATURE:
<221> NAME/KEY: MISC_FEATURE
<222> LOCATION: (5)..(5)
<223> OTHER INFORMATION: X is R, N or I
<220> FEATURE:
<221> NAME/KEY: MISC_FEATURE
<222> LOCATION: (6)..(6)
<223> OTHER INFORMATION: X is F, N or I
<220> FEATURE:
<221> NAME/KEY: MISC_FEATURE
<222> LOCATION: (7)..(7)
<223> OTHER INFORMATION: X is S, H, V, T or I

<400> SEQUENCE: 248

Xaa Val Xaa Xaa Xaa Xaa Xaa
1               5

<210> SEQ ID NO 249
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X is S or N
<220> FEATURE:
<221> NAME/KEY: MISC_FEATURE
<222> LOCATION: (3)..(3)
<223> OTHER INFORMATION: X is S or T
<220> FEATURE:
<221> NAME/KEY: MISC_FEATURE
<222> LOCATION: (4)..(4)
<223> OTHER INFORMATION: X is T, M or L
<220> FEATURE:
<221> NAME/KEY: MISC_FEATURE
<222> LOCATION: (5)..(5)
<223> OTHER INFORMATION: X is H or S
<220> FEATURE:
<221> NAME/KEY: MISC_FEATURE
<222> LOCATION: (6)..(6)
<223> OTHER INFORMATION: X is L, Y, I, V or E

<400> SEQUENCE: 249

Xaa Gln Xaa Xaa Xaa Xaa Pro Phe Thr
1               5

<210> SEQ ID NO 250
<211> LENGTH: 468
<212> TYPE: DNA
<213> ORGANISM: Homo sapiens

<400> SEQUENCE: 250

```
atgactcctg ggaagacctc attggtgtca ctgctactgc tgctgagcct ggaggccata    60
gtgaaggcag gaatcacaat cccacgaaat ccaggatgcc caaattctga ggacaagaac   120
ttcccccgga ctgtgatggt caacctgaac atccataacc ggaataccaa taccaatccc   180
aaaaggtcct cagattacta caaccgatcc acctcacctt ggaatctcca ccgcaatgag   240
gaccctgaga gatatccctc tgtgatctgg gaggcaaagt gccgccactt gggctgcatc   300
aacgctgatg ggaacgtgga ctaccacatg aactctgtcc ccatccagca agagatcctg   360
gtcctgcgca gggagcctcc acactgcccc aactccttcc ggctggagaa gatactggtg   420
tccgtgggct gcacctgtgt cacccgatt gtccaccatg tggcctaa             468
```

<210> SEQ ID NO 251
<211> LENGTH: 462
<212> TYPE: DNA
<213> ORGANISM: Oryctolagus cuniculus

<400> SEQUENCE: 251

```
atgtcgcttg ggaggattc atctgtgtca ctgctgctgc tgctgtgttt ggtggctact    60
gtgaagaatg gaatagcaat gccgcgaaat ccaggatgtc caaatgctga ggacaagaac   120
ttcccccaga atgtaaaagt cagcctgaac atccttaaca agagtgtaaa ttcccgaagg   180
ccttcagact actacaatcg atctacttca ccttggactc tccaccgcaa cgaggatcgt   240
gagagatatc cctctgtgat ctgggaggcc aagtgccgcc acttgggctg tgtcaatgct   300
gaagggaatg aggaccacca catgaactct gtcccaatcc agcaagagat cctggtccta   360
cgcagggagt cccagcactg cccacactca ttcggctgg agaagatgct ggtggctgta   420
ggatgcacct gtgtaacccc catcatccat cacatggcct aa                   462
```

<210> SEQ ID NO 252
<211> LENGTH: 477
<212> TYPE: DNA
<213> ORGANISM: Rattus rattus

<400> SEQUENCE: 252

```
atgagtcccc ggagaattcc atccatgtgc ctgatgctgt tgctgctact gaacctggag    60
gctacagtga aggcagcggt actcatccct caaagttcag tgtgtccaaa cgccgaggcc   120 ataactttc tccagaacgt gaaggtcaac ctgaaagtcc tcaactccct tagctcaaaa   180
gcgagctcca aaggccctc agactacctc aaccgttcca cttcaccctg gactctgagc   240
cgcaatgagg accctgatag atatccttct gtgatctggg aggcacagtg ccgccaccag   300
cgctgtgtca acgctgaggg gaagttggac caccacatga attctgttct catccagcaa   360
gagatcctgg tcctgaagag ggagcctgag aagtgcccct tcactttccg ggtggagaag   420
atgctggtgg gcgtgggctg cacctgcgtt cctctattg tccgccatgc gtcctaa     477
```

<210> SEQ ID NO 253
<211> LENGTH: 468
<212> TYPE: DNA
<213> ORGANISM: Macaca fascicularis

<400> SEQUENCE: 253

```
atgactcctg ggaagacctc attggtgcta ctgctgctgc tgctgagcct ggaggccata    60
gtgaaggcag gaatagcaat cccacgaaat tcaggatgcc caaattctga ggacaagaac   120
ttcccccgga ctgtgatggt caacctgaac atccataacc ggaataccag taccaatccc   180
```

```
aaaaggtcct cagattacta caaccgatcc acctcacctt ggaatctcca ccgcaatgag    240
gaccctgaga gatatccctc tgtgatctgg gaggcaaaat gccgccactt aggctgcgtc    300
aaggctgatg ggaacgtaga ctaccacatg aactctgtcc ccatccagca agagatcctg    360
gtcctgcgca gggagcctcg gcactgcccc aactccttcc ggctggagaa gatactggtg    420
tccgtgggct gcacctgtgt cacccccatt gtccaccatg tagcctaa                 468
```

<210> SEQ ID NO 254
<211> LENGTH: 477
<212> TYPE: DNA
<213> ORGANISM: Mus sp.

<400> SEQUENCE: 254

```
atgagtccag ggagagcttc atctgtgtct ctgatgctgt tgctgctgct gagcctggcg     60
gctacagtga aggcagcagc gatcatccct caaagctcag cgtgtccaaa cactgaggcc    120
aaggacttcc tccagaatgt gaaggtcaac ctcaaagtct ttaactccct tggcgcaaaa    180
gtgagctcca gaaggccctc agactacctc aaccgttcca cgtcaccctg gactctccac    240
cgcaatgaag accctgatag atatccctct gtgatctggg aagctcagtg ccgccaccag    300
cgctgtgtca atgcggaggg aaagctggac caccacatga attctgttct catccagcaa    360
gagatcctgg tcctgaagag ggagcctgag agctgcccct tcactttcag ggtcgagaag    420
atgctggtgg gtgtgggctg cacctgcgtg gcctcgattg tccgccaggc agcctaa      477
```

<210> SEQ ID NO 255
<211> LENGTH: 107
<212> TYPE: PRT
<213> ORGANISM: Homo sapiens
<400> SEQUENCE: 255

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 256
<211> LENGTH: 105
<212> TYPE: PRT
<213> ORGANISM: Homo sapiens
<400> SEQUENCE: 256

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45
```

```
Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 257
<211> LENGTH: 330
<212> TYPE: PRT
<213> ORGANISM: Homo sapiens

<400> SEQUENCE: 257

Ala Ser Phe Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Glu Trp Glu Thr Trp Arg Arg
        275                 280                 285

Leu Tyr Trp Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
                305                 310                 315                 320
Gln Lys Ser Leu Ser Leu Ser Pro Gly Lys
                325                 330

<210> SEQ ID NO 258
<211> LENGTH: 325
<212> TYPE: PRT
<213> ORGANISM: Homo sapiens

<400> SEQUENCE: 258

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 259
<211> LENGTH: 377
```

<212> TYPE: PRT
<213> ORGANISM: Homo sapiens

<400> SEQUENCE: 259

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 260

```
<211> LENGTH: 326
<212> TYPE: PRT
<213> ORGANISM: Homo sapiens

<400> SEQUENCE: 260

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 261
<211> LENGTH: 10
<212> TYPE: PRT
<213> ORGANISM: Artificial
<220> FEATURE:
<223> OTHER INFORMATION: Synthetic construct

<400> SEQUENCE: 261
```

-continued

Tyr Asp Ala Phe Thr Gly Thr Gly Ala Tyr
1               5                   10

<210> SEQ ID NO 262
<211> LENGTH: 25
<212> TYPE: PRT
<213> ORGANISM: Artificial
<220> FEATURE:
<223> OTHER INFORMATION: Synthetic construct

<400> SEQUENCE: 262

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 263
<211> LENGTH: 14
<212> TYPE: PRT
<213> ORGANISM: Artificial
<220> FEATURE:
<223> OTHER INFORMATION: Synthetic construct

<400> SEQUENCE: 263

Trp Val Arg Gln Ala Pro Gly Gln Gly Leu Glu Trp Met Gly
1               5                   10

<210> SEQ ID NO 264
<211> LENGTH: 32
<212> TYPE: PRT
<213> ORGANISM: Artificial
<220> FEATURE:
<223> OTHER INFORMATION: Synthetic construct

<400> SEQUENCE: 264

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 265
<211> LENGTH: 11
<212> TYPE: PRT
<213> ORGANISM: Artificial
<220> FEATURE:
<223> OTHER INFORMATION: Synthetic construct

<400> SEQUENCE: 265

Trp Gly Gln Gly Thr Leu Val Thr Val Ser Ser
1               5                   10

<210> SEQ ID NO 266
<211> LENGTH: 23
<212> TYPE: PRT
<213> ORGANISM: Artificial
<220> FEATURE:
<223> OTHER INFORMATION: Synthetic construct

<400> SEQUENCE: 266

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 267

<211> LENGTH: 15
<212> TYPE: PRT
<213> ORGANISM: Artificial
<220> FEATURE:
<223> OTHER INFORMATION: Synthetic construct

<400> SEQUENCE: 267

Trp Tyr Leu Gln Lys Pro Gly Gln Ser Pro Gln Leu Leu Ile Tyr
1               5                   10                  15

<210> SEQ ID NO 268
<211> LENGTH: 32
<212> TYPE: PRT
<213> ORGANISM: Artificial
<220> FEATURE:
<223> OTHER INFORMATION: Synthetic construct

<400> SEQUENCE: 268

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 269
<211> LENGTH: 10
<212> TYPE: PRT
<213> ORGANISM: Artificial
<220> FEATURE:
<223> OTHER INFORMATION: Synthetic construct

<400> SEQUENCE: 269

Phe Gly Gln Gly Thr Lys Leu Glu Ile Lys
1               5                   10

<210> SEQ ID NO 270
<211> LENGTH: 119
<212> TYPE: PRT
<213> ORGANISM: Mus sp.

<400> SEQUENCE: 270

Gln Val Gln Leu Gln Gln Ser Arg Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Val Ile Asn Pro Asn Tyr Gly Thr Thr Asp Tyr Asn Gln Arg Phe
    50                  55                  60

Lys Gly Lys Ala Thr Leu Thr Val Asp Gln Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Val Ile Tyr Asp Tyr Ala Thr Gly Thr Gly Tyr Trp Gly Gln Gly
            100                 105                 110

Ser Pro Leu Thr Val Ser Ser
        115

<210> SEQ ID NO 271
<211> LENGTH: 112
<212> TYPE: PRT
<213> ORGANISM: Mus sp.

<400> SEQUENCE: 271

```
Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110
```

<210> SEQ ID NO 272
<211> LENGTH: 107
<212> TYPE: PRT
<213> ORGANISM: Homo sapiens

<400> SEQUENCE: 272

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 273
<211> LENGTH: 445
<212> TYPE: PRT
<213> ORGANISM: Homo sapiens

<400> SEQUENCE: 273

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 274
<211> LENGTH: 219
<212> TYPE: PRT
<213> ORGANISM: Homo sapiens

<400> SEQUENCE: 274

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
```

-continued

```
                35                  40                  45
Pro Gln Leu Leu Ile Tyr Lys Val Ser Asn Arg Phe Ile Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Leu Pro Phe Thr Phe Gly Gln Gly Thr Lys Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 275
<211> LENGTH: 10
<212> TYPE: PRT
<213> ORGANISM: Homo sapiens

<400> SEQUENCE: 275

Ala Asp Gly Asn Val Asp Tyr His Met Asn
1               5                   10

<210> SEQ ID NO 276
<211> LENGTH: 7
<212> TYPE: PRT
<213> ORGANISM: Homo sapiens

<400> SEQUENCE: 276

Asp Gly Asn Val Asp Tyr His
1               5

<210> SEQ ID NO 277
<211> LENGTH: 107
<212> TYPE: PRT
<213> ORGANISM: Artificial
<220> FEATURE:
<223> OTHER INFORMATION: Synthetic construct

<400> SEQUENCE: 277

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 278
<211> LENGTH: 326
<212> TYPE: PRT
<213> ORGANISM: Artificial
<220> FEATURE:
<223> OTHER INFORMATION: Synthetic construct

<400> SEQUENCE: 278

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly
            325

<210> SEQ ID NO 279
<211> LENGTH: 219
<212> TYPE: PRT
<213> ORGANISM: Artificial
<220> FEATURE:
<223> OTHER INFORMATION: Synthetic construct

<400> SEQUENCE: 279

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 280
<211> LENGTH: 445
<212> TYPE: PRT
<213> ORGANISM: Artificial
<220> FEATURE:
<223> OTHER INFORMATION: Synthetic construct

<400> SEQUENCE: 280

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 281
<211> LENGTH: 720
<212> TYPE: DNA
<213> ORGANISM: Artificial
<220> FEATURE:
<223> OTHER INFORMATION: Synthetic construct

<400> SEQUENCE: 281
```

| | |
|---|---:|
| atggagacag acacactcct gctatgggta ctgctgctct gggttccagg atccaccggt | 60 |
| gatattgtga tgactcagac tccactctcc ctgtccgtca cccctggaca gccggcctcc | 120 |
| atctcctgca gatctagtag gagccttgta cacagtcgtg aaacaccta tttacattgg | 180 |
| tacctgcaga agccaggcca atctccacag ctcctaattt ataaagtttc caaccggttt | 240 |
| attggggtcc cagacagatt cagcggcagt gggtcaggca cagatttcac actgaaaatc | 300 |
| agcagggtgg aggccgaaga tgttggggtt tattactgct ctcaaagtac acatcttcca | 360 |
| ttcacgtttg gccaagggac caagctggag atcaaacgaa ctgtggctgc accatctgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggataa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgctaa | 720 |

<210> SEQ ID NO 282
<211> LENGTH: 1398
<212> TYPE: DNA
<213> ORGANISM: Artificial
<220> FEATURE:
<223> OTHER INFORMATION: Synthetic construct

<400> SEQUENCE: 282

| | |
|---|---:|
| atggagacag acacactcct gctatgggta ctgctgctct gggttccagg atccaccggt | 60 |
| caggtgcagc tggtgcagtc tggggctgag gtgaagaagc ctgggtcctc agtgaaggtt | 120 |
| tcctgcaagg catctggtta ctcattcact gactaccata ttcattgggt gcgacaggcc | 180 |
| cctggacaag ggcttgagtg gatgggagta attaatccta tgtatggtac tactgactac | 240 |
| aatcagaggt tcaagggcag agtcaccatt accgcggacg aatccacgag cacagcctac | 300 |
| atggagctga gcagcctgag atctgaggac acggccgtgt attactgtgc gagatatgat | 360 |
| tactttactg gacgggtgt gtactggggc caaggaaccc tggtcaccgt ctcctcagcc | 420 |
| tccaccaagg gcccatcggt cttccccta gcgccctgct ccaggagcac ctccgagagc | 480 |
| acagccgccc tgggctgcct ggtcaaggac tacttccccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac gaagacctac | 660 |
| acctgcaacg tagatcacaa gcccagcaac accaaggtgg acaagagagt tgagtccaaa | 720 |
| tatggtcccc catgcccacc ctgcccagca cctgagttcc tggggggacc atcagtcttc | 780 |
| ctgttccccc caaaacccaa ggacactctc atgatctccc ggacccctga ggtcacgtgc | 840 |
| gtggtggtgg acgtgagcca ggaagacccc gaggtccagt tcaactggta cgtggatggc | 900 |
| gtggaggtgc ataatgccaa gacaaagccg cgggaggagc agttcaacag cacgtaccgt | 960 |
| gtggtcagcg tcctcaccgt cctgcaccag gactggctga acggcaagga gtacaagtgc | 1020 |
| aaggtctcca acaaaggcct cccgtcctcc atcgagaaaa ccatctccaa agccaaaggg | 1080 |
| cagccccgag agccacaggt gtacaccctg cccccatccc aggaggagat gaccaagaac | 1140 |
| caggtcagcc tgacctgcct ggtcaaaggc ttctacccca gcgacatcgc cgtggagtgg | 1200 |
| gaaagcaatg ggcagccgga gaacaactac aagaccacgc ctcccgtgct ggactccgac | 1260 |
| ggctccttct tcctctacag caggctaacc gtggacaaga gcaggtggca ggaggggaat | 1320 |

```
gtcttctcat gctccgtgat gcatgaggct ctgcacaacc actacacaca gaagagcctc    1380
tccctgtctc tgggttga                                                   1398

<210> SEQ ID NO 283
<211> LENGTH: 660
<212> TYPE: DNA
<213> ORGANISM: Artificial
<220> FEATURE:
<223> OTHER INFORMATION: Synthetic construct

<400> SEQUENCE: 283
gatattgtga tgactcagac tccactctcc ctgtccgtca cccctggaca gccggcctcc      60
atctcctgca gatctagtag gagccttgta cacagtcgtg aaacaccta tttacattgg     120 tacctgcaga agccaggcca atctccacag ctcctaattt ataaagtttc caaccggttt    180
attggggtcc cagacagatt cagcggcagt gggtcaggca cagatttcac actgaaaatc    240
agcagggtgg aggccgaaga tgttggggtt tattactgct ctcaaagtac acatcttcca    300
ttcacgtttg gccaagggac caagctggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg  agagtgctaa    660

<210> SEQ ID NO 284
<211> LENGTH: 1338
<212> TYPE: DNA
<213> ORGANISM: Artificial
<220> FEATURE:
<223> OTHER INFORMATION: Synthetic construct

<400> SEQUENCE: 284
caggtgcagc tggtgcagtc tggggctgag gtgaagaagc ctgggtcctc agtgaaggtt      60
tcctgcaagg catctggtta ctcattcact gactaccata ttcattgggt gcgacaggcc    120
cctggacaag gccttgagtg gatgggagta attaatccta tgtatggtac tactgactac    180
aatcagaggt tcaagggcag agtcaccatt accgcggacg aatccacgag cacagcctac    240
atggagctga gcagcctgag atctgaggac acggccgtgt attactgtgc gagatatgat    300
tactttactg gacgggtgt gtactgggc caaggaaccc tggtcaccgt ctcctcagcc     360
tccaccaagg gcccatcggt cttcccgcta gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc ctgcccagca cctgagttcc tggggggacc atcagtcttc    720
ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaagggg   1020
```

```
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gaaagcaatg ggcagccgga gaacaactac aagaccacgc ctcccgtgct ggactccgac    1200
ggctccttct tcctctacag caggctaacc gtggacaaga gcaggtggca ggagggggaat   1260 gtcttctcat gctccgtgat gcatgaggct ctgcacaacc actacacaca gaagagcctc    1320
tccctgtctc tgggttga                                                   1338
```